(12) United States Patent
Scadden et al.

(10) Patent No.: US 8,642,569 B2
(45) Date of Patent: Feb. 4, 2014

(54) METHODS FOR EXPANSION OF HEMATOPOIETIC STEM AND PROGENITOR CELLS

(75) Inventors: David Scadden, Weston, MA (US); Jonas Larsson, Lund (SE)

(73) Assignee: The General Hospital Corporation, Boston, MA (US)

( * ) Notice: Subject to any disclaimer, the term of this patent is extended or adjusted under 35 U.S.C. 154(b) by 46 days.

(21) Appl. No.: 13/145,706

(22) PCT Filed: Jan. 21, 2010

(86) PCT No.: PCT/US2010/021638
§ 371 (c)(1),
(2), (4) Date: Aug. 31, 2011

(87) PCT Pub. No.: WO2010/085555
PCT Pub. Date: Jul. 29, 2010

(65) Prior Publication Data
US 2011/0305675 A1    Dec. 15, 2011

Related U.S. Application Data

(60) Provisional application No. 61/145,989, filed on Jan. 21, 2009.

(51) Int. Cl.
*C12N 15/113* (2010.01)
(52) U.S. Cl.
USPC ........................................................ 514/44 A
(58) Field of Classification Search
None
See application file for complete search history.

(56) References Cited

U.S. PATENT DOCUMENTS

| | | | |
|---|---|---|---|
| 2007/0004040 A1* | 1/2007 | Brashears et al. | 435/455 |
| 2008/0081791 A1 | 4/2008 | Huang et al. | |
| 2008/0305085 A1* | 12/2008 | Scadden et al. | 424/93.7 |

FOREIGN PATENT DOCUMENTS

| | | |
|---|---|---|
| WO | 2004048576 A1 | 6/2004 |
| WO | 2004065563 A2 | 8/2004 |
| WO | 2008021475 A2 | 2/2008 |
| WO | 2008070082 A2 | 6/2008 |
| WO | 2009155041 A2 | 12/2009 |
| WO | 2010017551 A2 | 2/2010 |

OTHER PUBLICATIONS

Ali, et al, "Forward RNAi screens in primary human hematopoietic stem/progenitor cells", Blood, vol. 113, No. 16, pp. 3690-3695, 2009.
Devroe, et al, "Human Mob Proteins Regulate the NDR1 and NDR2 Serine Threonine Kinases", The Journal of Biological Chemistry, vol. 279, No. 23, pp. 24444-24451, 2004.
Berns et al., Nature, 428:431-437 (2004). "A large-scale RNAi screen in human cells identifies new components of the p53 pathway."
Kolfschoten et al., Cell, 121:849-858 (2005). "A genetic screen identifies PITX1 as a suppressor of RAS activity and tumorigenicity."
Moffat et al., Cell, 124:1283-1298 (2006). "A lentiviral RNAi library for human and mouse genes applied to an arrayed viral high-content screen."
Paddison et al., Nature, 428:427-431 (2004). "A resource for large-scale RNA-interference-based screens in mammals."
Sorrentino, Nat Rev Immunol, 4:878-888 (2004). "Clinical strategies for expansion of haematopoietic stem cells."

* cited by examiner

*Primary Examiner* — Tracy Vivlemore
(74) *Attorney, Agent, or Firm* — David S. Resnick; Nixon Peabody LLP

(57) ABSTRACT

Described herein are methods and compositions for expanding hematopoietic stem and progenitor cells (HSPC) ex vivo and in vivo, and methods and compositions for transplanting HSPCs and treatment of anemia in a human subject. HSPCs are expanded in the presence of an inhibitor of serine threonine kinase 38 (STK38), wherein said inhibitor is preferably an RNAi agent.

12 Claims, 10 Drawing Sheets

SEQUENCE LISTING

<160> NUMBER OF SEQ ID NOS: 37

<210> SEQ ID NO 1
<211> LENGTH: 21

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ggtgcgctcc tggacgtagc c                                              21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gaagaacaca gcggtaggaa t                                              21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
agagccagat tgtgccaact a                                              21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
cctgcttcga tttcaccctt t                                              21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
cccaactttg atgtttctat t                                              21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gcacttagac agcagacaca a                                              21

<210> SEQ ID NO 7
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 7
ccttcgttcc ttgggatcaa t                                              21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
cgtgaatgtc tactgtttaa a                                              21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
cagcaagggc catgtgaaac t                                              21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gctcggaagg aaacagagtt t                                              21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gcagaaacag tattagccat a                                              21

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
cccaccaata tgtcatagta a                                              21

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
```

```
                              oligonucleotide

<400> SEQUENCE: 13
cccaccaagt atttccttta t                                              21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
cagagacatc aaaccagaca a                                              21

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
catgtgaaac tttctgactt t                                              21

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
ctacgtcaag gagaggtcta a                                              21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
tattccatcc ggaagcagta c                                              21

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
gcgatgttac tagcagcaga a                                              21

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
```

-continued

<400> SEQUENCE: 19
ggatgaatac tgccatttgt ctcg                                           24

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
aggccgaagg aatagaaga                                                 19

<210> SEQ ID NO 21
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
cagcaagggc catgtga                                                   17

<210> SEQ ID NO 22
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
gcaagggcca tgtga                                                     15

<210> SEQ ID NO 23
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gggccatgtg aaact                                                     15

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
agcaagggcc atgtgaaac                                                 19

<210> SEQ ID NO 25
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25

```
aagggccatg tgaaac                                                   16

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
agcaagggcc atgtgaaact                                               20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
cagcaagggc catgtgaaac                                               20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
cagcaagggc catgtgaaac                                               20

<210> SEQ ID NO 29
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
caggaagggc catctga                                                  17

<210> SEQ ID NO 30
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
gcatgggcca tctga                                                    15

<210> SEQ ID NO 31
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
gggccatctg aaact                                                    15
```

```
<210> SEQ ID NO 32
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
agcatgggcc atgtgaaag                                                    19

<210> SEQ ID NO 33
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
aagggccatg tgatac                                                       16

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
agcaacggcc atgtgaaact                                                   20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
cagcatgggc catgtgaaac                                                   20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
cagcatgggc catgtgaaac                                                   20

<210> SEQ ID NO 37
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(21)
<223> OTHER INFORMATION: a, c, t, g, unknown or other
```

```
<400> SEQUENCE: 37
aannnnnnnn nnnnnnnnnn ntt                                          23
```

METHODS FOR EXPANSION OF HEMATOPOIETIC STEM AND PROGENITOR CELLS

CROSS REFERENCE TO RELATED APPLICATION

This application is a 35 U.S.C. §371 National Phase Entry Application of International Application No. PCT/US2010/21638 filed Jan. 21, 2010, which designates the United States, and which claims the benefit under 35 U.S.C. §119(e) of the U.S. provisional application No. 61/145,989 filed Jan. 21, 2009, the contents of which are incorporated herein by reference in its entirety.

GOVERNMENT SUPPORT

This invention was made with Government support under Grant No.: R01 HL65909-12 awarded by the National Institutes of Health. The Government has certain rights in the invention.

BACKGROUND OF THE INVENTION

Hematopoietic stem and progenitor cells (HSPC) self-renew and differentiate to form all blood cells throughout animal life. The hematopoietic system is composed of many different cell types at various stages of maturity. HSCs give rise to all the blood cell types including myeloid (monocytes and macrophages, neutrophils, basophils, eosinophils, erythrocytes, megakaryocytes/platelets, dendritic cells), and lymphoid lineages (T-cells, B-cells, NK-cells).

As stem cells, they are defined by their ability to form multiple cell types (multipotency) and their ability to self-renew. It is known that a small number of HSCs can expand to generate a very large number of progeny HSCs. This phenomenon is used in bone marrow transplant when a small number of HSCs reconstitute the hematopoietic system. The ability to self-renew and differentiate to form all blood cells provides a constant supply of blood cells throughout animal life. The supply is needed for replacing old, worn out or dead blood cells in the body.

The intricate balance between the two characteristic self-renewal and differentiation stem cell states is required for maintaining hematopoietic homeostasis and for responding to tissue injury. Stem cell population size is tightly regulated and thought to be dictated by rates of proliferation, relative frequency of differentiative versus self-renewal outcomes and apoptosis. Disruption of any of these processes could lead to stem cell exhaustion or increased risk of leukemogenesis (1-5). However, the molecular events specifying stem cell population size are still poorly understood. Identifying the genes and pathways that regulate self-renewal and differentiation in HSCs can provide ways to regulate stem cell fate and the development of conditions that would enable amplification of transplantable HSCs.

SUMMARY OF THE INVENTION

Embodiments of the present invention are based on the discovery that small hairpin RNAs or short hairpin RNAs (shRNA) that target six proteins, when transduced into an isolated cell population of primary HSPCs, increased the colony forming capacity and the long-term culture forming capacity of the HSPCs. The transduced isolated cell population of primary HSPCs scored two- to five-fold higher in a standard methylcellulose colony forming cell assay (CFC) and over 100 fold higher in a standard long term culture initiating cell assay (LTC-IC). The target six proteins are exostoses 1 (EXT1), phospholipase C zeta 1 (PLCZ1); serine threonine kinase 38 (STK38); protein tyrosine phosphatase, non-receptor type 9 (PTPN9); egl nine homolog 3 (EGLN3); mutL homolog 1 (MLH1); and ATP-binding cassette, subfamily C (CFTR/MRP), member 12 (ABCC12). Accordingly, inhibiting the protein activity and/or the protein expression of EXT1, STK38, PTPN9, EGLN3, MLH1, and/or ABCC12 can lead to increased expansion of HSCs.

In one embodiment of each of the therapeutic methods described herein, the subject is first diagnosed with anemia or with a need for increased or replacement HSPCs and numbers. In one embodiment of each of the therapeutic methods described herein, the subject has a need for increased blood cells.

Accordingly, in one embodiment, provided herein is a method for expanding ex vivo a population of hematopoietic stem progenitor cells (HSPCs), the method comprising contacting an isolated cell population comprising an HSPC with an RNAi agent which comprises at least 15 contiguous nucleotides differing by no more than 3 nucleotides from SEQ ID NO: 9.

In one embodiment, described herein is a method for promoting hematopoietic stem progenitor cell (HSPC) self renewal ex vivo, the method comprising contacting an isolated cell population comprising an HSPC with an RNAi agent which comprises at least 15 contiguous nucleotides differing by no more than 3 nucleotides from SEQ ID NO: 9.

In one embodiment, described herein is a method for promoting hematopoietic stem progenitor cell (HSPC) expansion in a subject, comprising administering a therapeutically effective amount of a pharmaceutical composition comprising at least one RNAi agent and a pharmaceutically acceptable carrier, wherein the RNAi agent which comprises at least 15 contiguous nucleotides differing by no more than 3 nucleotides from SEQ ID NO: 9.

In one embodiment, described herein is a method of treating anemia in a subject in need thereof, the method comprising administering a therapeutically effective amount of a pharmaceutical composition comprising at least one RNAi agent and a pharmaceutically acceptable carrier, wherein the RNAi agent which comprises at least 15 contiguous nucleotides differing by no more than 3 nucleotides from SEQ ID NO: 9.

In one embodiment, described herein is a method for transplanting a population of hematopoietic stem progenitor cells (HSPCs), the method comprising: (a) contacting an isolated cell population comprising an HSPC with a RNAi agent which comprises at least 15 contiguous nucleotides differing by no more than 3 nucleotides from SEQ ID NO: 9; (b) culturing ex vivo the HSPC from step (a); and (c) implanting the cultured HSPC from step (b) into a subject. In one embodiment, the HSPC of step (b) is cultured for at least 20 days in ex vivo before step (c).

In one embodiment, described herein is a use of an RNAi agent for transplanting a population of hematopoietic stem progenitor cells (HSPCs), the use comprising: (a) contacting an isolated cell population comprising an HSPC with a RNAi agent which comprises at least 15 contiguous nucleotides differing by no more than 3 nucleotides from SEQ ID NO: 9; (b) culturing ex vivo the HSPC from step (a); and (c) implanting the cultured HSPCs from step (b) into a subject. In one embodiment, the HSPC in step (b) is cultured for at least 20 days.

In one embodiment, described herein is for a method for expanding ex vivo a population of hematopoietic stem progenitor cells (HSPCs), the method comprising contacting an isolated cell population comprising an HSPC with an agent that inhibits serine threonine kinase 38 (STK38).

In one embodiment, described herein is a method for promoting hematopoietic stem progenitor cell (HSPC) self renewal ex vivo, the method comprising contacting an isolated cell population comprising an HSPC with an agent that inhibits serine threonine kinase 38 (STK38).

In one embodiment, described herein is a method for promoting hematopoietic stem progenitor cell (HSPC) expansion in a subject, comprising administering a therapeutically effective amount of a pharmaceutical composition comprising an agent that inhibits serine threonine kinase 38 (STK38).

In one embodiment, described herein is a method of treating anemia in a subject in need thereof, the method comprising administering a therapeutically effective amount of a pharmaceutical composition comprising an agent that inhibits serine threonine kinase 38 (STK38).

In another embodiment, described herein is a method for transplanting a population of hematopoietic stem progenitor cells (HSPCs), the method comprising: (a) contacting an isolated cell population comprising an HSPC with an agent which inhibits serine threonine kinase 38 (STK38); (b) culturing ex vivo the HSPC from step (a); and (c) implanting the cultured HSPC from step (b) into a subject.

In another embodiment, described herein is a use of an agent which inhibits serine threonine kinase 38 (STK38) for transplanting a population of hematopoietic stem progenitor cells (HSPCs), the use comprising: (a) contacting an isolated cell population comprising an HSPC with an agent which inhibits serine threonine kinase 38 (STK38); (b) culturing ex vivo the HSPC from step (a); and (c) implanting the cultured HSPC from step (b) into a subject. In one embodiment, the isolated cell population comprising an HSPC from step (b) is cultured for at least 20 days.

In one embodiment, the agent inhibits the activity of STK38. In one embodiment, the agent that inhibits the protein activity of STK38 is a small molecule, nucleic acid, nucleic acid analogue, protein, antibody, peptide, aptamer or variants or fragments thereof. In some embodiments, the agent that inhibits the protein activity of STK38 is a small molecule, for example but not limited to a small molecule reversible inhibitor, an inhibiting antibody or functional fragments thereof or an irreversible small molecule inhibitor of STK38 protein activity.

In one embodiment, the agent is an RNAi agent that inhibits gene expression of STK38. In one embodiment, the RNAi agent comprises a double-stranded ribonucleic acid (dsRNA) wherein the dsRNA comprises a sense strand and an antisense strand, wherein the antisense strand comprising a region of complementarity to and have at least 15 contiguous nucleotides differing by no more than 3 nucleotides from SEQ ID NO: 9. In one embodiment, the RNAi agent comprises SEQ ID NO: 9. In one embodiment, the antisense strand comprises a region of complementarity to SEQ ID NO: 9. In one embodiment, the sense strand comprises SEQ ID NO: 9.

In one embodiment, the isolated cell population comprising an HSPC contacted with the agent or RNAi agent exhibits at least a 2 fold increase in colony formation capacity when compared to an isolated cell population comprising an HSPC that is not contacted with the agent or RNAi agent. The isolated cell population comprising an HSPC that is not contacted with the agent or RNAi agent function as a control.

In one embodiment, the isolated cell population comprising an HSPC contacted with the agent or RNAi agent exhibits at least 5 fold increase in long-term culture colony formation capacity when compared to an isolated cell population comprising an HSPC that is not contacted with the agent or RNAi agent. The isolated cell population comprising an HSPC that is not contacted with the agent or RNAi agent functions as a control or reference.

In one embodiment, described herein is a method for expanding ex vivo a population of hematopoietic stem progenitor cells (HSPCs), the method comprising contacting an isolated cell population comprising an HSPC with an agent which inhibits the function or expression of a protein selected from the group consisting of exostoses 1 (EXT1), phospholipase C zeta 1 (PLCZ1), protein tyrosine phosphatase, non-receptor type 9 (PTPN9), egl nine homolog 3 (EGLN3), mutL homolog 1 (MLH1) and ATP-binding cassette sub-family C(CFTR/MRP), member 12 (ABCC12).

In another embodiment, described herein is a method for promoting hematopoietic stem progenitor cell (HSPC) expansion in a subject, comprising administering a therapeutically effective amount of a pharmaceutical composition comprising an agent which inhibits the function or expression of a protein selected from the group consisting of exostoses 1 (EXT1), phospholipase C zeta 1 (PLCZ1), protein tyrosine phosphatase, non-receptor type 9 (PTPN9), egl nine homolog 3 (EGLN3), mutL homolog 1 (MLH1) and ATP-binding cassette sub-family C(CFTR/MRP), member 12 (ABCC12).

In one embodiment, described herein is a method for transplanting a population of hematopoietic stem progenitor cells (HSPCs), the method comprising: (a) contacting an isolated cell population comprising an HSPC with at least one an agent which inhibits a protein selected from the group consisting of exostoses 1 (EXT1), phospholipase C zeta 1 (PLCZ1), protein tyrosine phosphatase, non-receptor type 9 (PTPN9), egl nine homolog 3 (EGLN3), mutL homolog 1 (MLH1) and ATP-binding cassette sub-family C(CFTR/MRP), member 12 (ABCC12); (b) culturing ex vivo the isolated cell population comprising an HSPC from step (a); and (c) transplanting the cultured HSPC from step (b) into a subject. In one embodiment, the isolated cell population comprising an HSPC in step (b) is cultured for at least 20 days.

In one embodiment, the agent inhibits the activity of a protein selected from the group consisting of EXT1, PTPN9, EGLN3, MLH1, and ABCC12. In one embodiment, the agent inhibits the activity of EXT1, PTPN9, EGLN3, MLH1 or ABCC12. In one embodiment, the agent that inhibits the protein activity of EXT1, PTPN9, EGLN3, MLH1, and ABCC12 is a small molecule, nucleic acid, nucleic acid analogue, protein, antibody, peptide, aptamer or variants or fragments thereof. In some embodiments, the agent that inhibits the protein activity of EXT1, PTPN9, EGLN3, MLH1, or ABCC12 is a small molecule, for example but not limited to a small molecule reversible or irreversible inhibitor of EXT1, PTPN9, EGLN3, MLH1, and ABCC12 protein.

In one embodiment, the agent is an RNAi agent that inhibits the gene expression of EXT1, PTPN9, EGLN3, MLH1 or ABCC12. In one embodiment, the RNAi agent comprises a double-stranded ribonucleic acid (dsRNA) wherein the dsRNA comprises a sense strand and an antisense strand, wherein the antisense strand comprising a region of complementary to and have at least 15 contiguous nucleotides that differ by no more than 3 nucleotides from a sequence selected from the group consisting of SEQ ID NOS: 2, 5, 8, 16, 17, and 18. In one embodiment, the antisense strand comprises a region of complementary to a sequence selected from the group consisting of SEQ ID NOS: 2, 5, 8, 16, 17, and 18. In one embodiment, the sense strand comprises a sequence selected from the group consisting of SEQ ID NOS: 2, 5, 8, 16, 17, and 18. In some embodiments, the RNAi agent is a shRNA that comprises a sequence selected from the group consisting of SEQ ID NOS: 2, 5, 8, 16, 17, and 18.

In one embodiment, described herein is a method for expanding ex vivo a population of hematopoietic stem progenitor cells (HSPCs), the method comprising contacting an isolated cell population comprising an HSPC with at least one RNAi agent which comprises at least 15 contiguous nucleotides differing by no more than 3 nucleotides from a sequence selected from the group consisting of SEQ ID NOS: 2, 5, 8, 16, 17, and 18.

In another embodiment, described herein is a method for promoting hematopoietic stem progenitor cell (HSPC) expansion in a subject, comprising administering a therapeutically effective amount of a pharmaceutical composition comprising at least one RNAi agent and a pharmaceutically acceptable carrier, wherein the RNAi agent comprises at least 15 contiguous nucleotides differing by no more than 3 nucleotides from a sequence selected from the group consisting of SEQ ID NOS: 2, 5, 8, 16, 17, and 18.

In one embodiment, described herein is a method for transplanting a population of hematopoietic stem progenitor cells (HSPCs), the method comprising: (a) contacting an isolated cell population comprising an HSPC with at least one an RNAi agent which comprises at least 15 contiguous nucleotides differing by no more than 3 nucleotides from a sequence selected from the group consisting of SEQ ID NOS: 2, 5, 8, 16, 17, and 18; (b) culturing ex vivo the isolated cell population comprising an HSPC from step (a); and (c) implanting the cultured HSPC from step (b) into a subject. In one embodiment, the isolated cell population comprising an HSPC in step (b) is cultured for at least 20 days.

In one embodiment, the at least one RNAi agent comprises a double-stranded ribonucleic acid (dsRNA) wherein the dsRNA comprises a sense strand and an antisense strand, wherein the antisense strand comprising a region of sequence complementarity to and have at least 15 contiguous nucleotides that differ by no more than 3 nucleotides from a sequence selected from the group consisting of SEQ ID NOS: 2, 5, 8, 16, 17, and 18. In one embodiment, the antisense strand comprises a region of complementarity to a sequence selected from the group consisting of SEQ ID NOS: 2, 5, 8, 16, 17, and 18. In one embodiment, the sense strand comprises a sequence selected from the group consisting of SEQ ID NOS: 2, 5, 8, 16, 17, and 18. In some embodiments, the RNAi agent is a shRNA that comprises a sequence selected from the group consisting of SEQ ID NOS: 2, 5, 8, 16, 17, and 18. In one embodiment, the sense strand comprises SEQ ID NO: 2. In one embodiment, the sense strand comprises SEQ ID NO: 5. In one embodiment, the sense strand comprises SEQ ID NO: 8. In one embodiment, the sense strand comprises SEQ ID NO: 16. In one embodiment, the sense strand comprises SEQ ID NO: 17. In one embodiment, the sense strand comprises SEQ ID NO: 18.

In one embodiment, the isolated cell population comprising an HSPC is cryopreserved before being contacted with the agent or RNAi agent.

In one embodiment, the isolated cell population comprising an HSPC is cryopreserved after contacting with the agent or RNAi agent and expanding in culture.

In one embodiment, described herein is a pharmaceutical composition comprising an isolated cell population comprising an HSPC and a pharmaceutically-acceptable carrier, wherein the HSPC has been contacted with at least one RNAi agent which comprises at least 15 contiguous nucleotides differing by no more than 3 nucleotides from a sequence selected from the group consisting of SEQ ID NOS: 2, 5, 8, 9, 16, 17, and 18, and/or contacted with at least one agent which inhibits a protein selected from the group consisting of EXT1, PLCZ1, PTPN9, EGLN3, MLH1 and ABCC12.

In one embodiment, described herein is a method of treating anemia in a host in need thereof, the method comprising administering a pharmaceutical composition comprising an isolated cell population comprising an HSPC disclosed herein and a pharmaceutically-acceptable carrier.

DETAILED DESCRIPTION OF THE INVENTION

Figure 1:
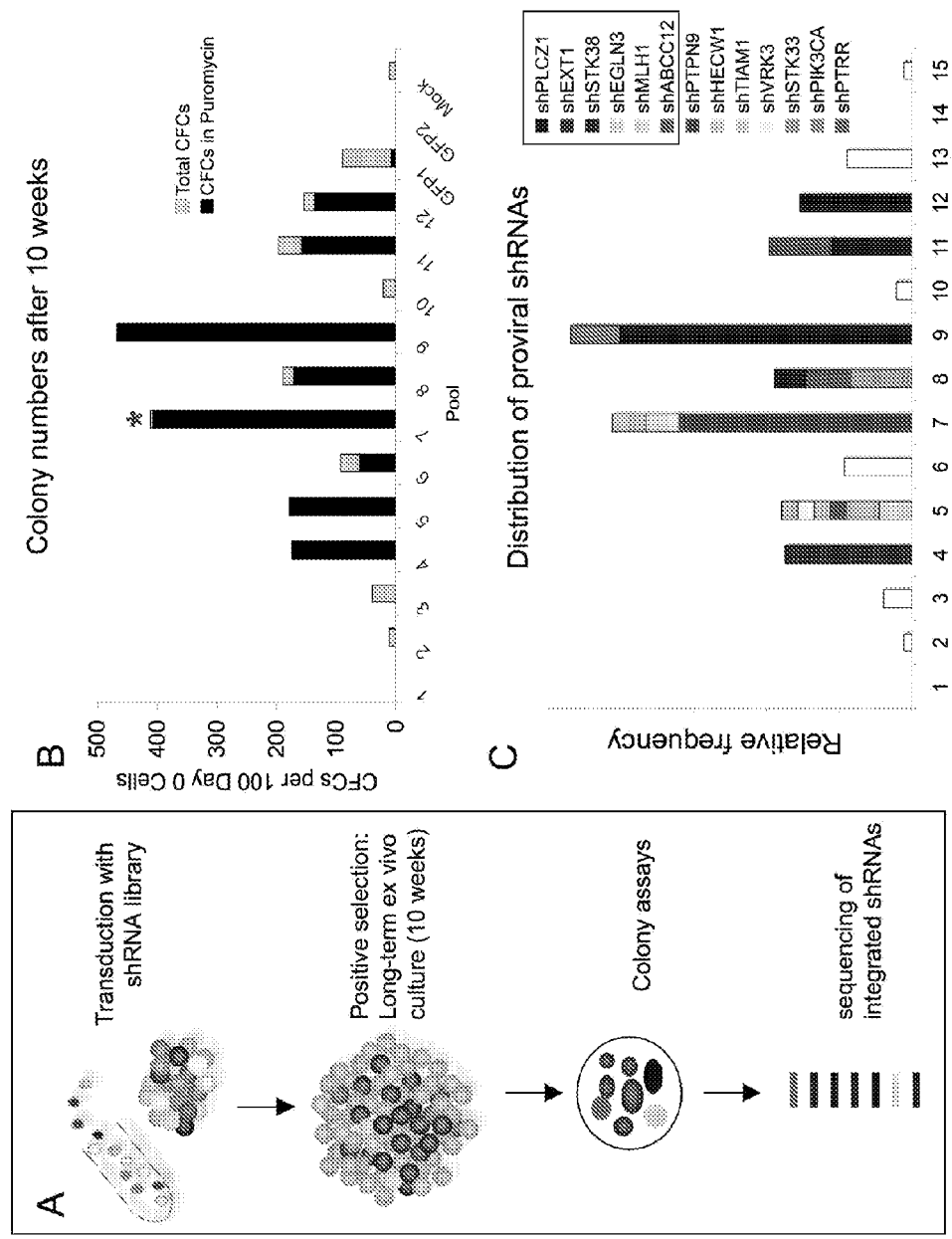
FIG. 1A shows the overall design of an RNAi screening strategy in human CB CD34 cells.
FIG. 1B shows the colony forming cell (CFC) levels after 10 weeks culture for 12 pools of library-transduced cells, independently assayed CFC levels. Control pools were transduced with shRNA against GFP in two pools, and one pool was left un-transduced (mock). Pool 7 showed high levels of BFU-E growth indicated by an asterix.
FIG. 1C shows the distribution of proviral shRNAs among the screening pools that showed increased CFC levels. The graph shows relative abundance of shRNAs in each screening pool as an overlay on the colony numbers shown in FIG. 1B.

Unless otherwise explained, all technical and scientific terms used herein have the same meaning as commonly understood by one of ordinary skill in the art to which this disclosure belongs. Definitions of common terms in molecular biology may be found in Benjamin Lewin, Genes IX, published by Jones & Bartlett Publishing, 2007 (ISBN-13: 9780763740634); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8). Further, unless otherwise required by context, singular terms shall include pluralities and plural terms shall include the singular.

Unless otherwise stated, the present invention was performed using standard procedures known to one skilled in the art, for example, in Maniatis et al., Molecular Cloning: A Laboratory Manual, Cold Spring Harbor Laboratory Press, Cold Spring Harbor, N.Y., USA (1982); Sambrook et al., Molecular Cloning: A Laboratory Manual (2 ed.), Cold Spring Harbor Laboratory Press, Cold Spring Harbor, N.Y., USA (1989); Davis et al., Basic Methods in Molecular Biology, Elsevier Science Publishing, Inc., New York, USA (1986); Current Protocols in Molecular Biology (CPMB) (Fred M. Ausubel, et al. ed., John Wiley and Sons, Inc.), Current Protocols in Immunology (CPI) (John E. Coligan, et. al., ed. John Wiley and Sons, Inc.), Current Protocols in Cell Biology (CPCB) (Juan S. Bonifacino et. al. ed., John Wiley and Sons, Inc.), Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998), Methods in Molecular biology, Vol. 180, Transgenesis Techniques by Alan R. Clark editor, second edition, 2002, Humana Press, and Methods in Molecular Biology, Vo. 203, 2003, Transgenic Mouse, edited by Marten H. Hofker and Jan van Deursen, which are all herein incorporated by reference in their entireties.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used in connection with percentages will mean ±1%.

All patents and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The present invention relates to methods and compositions for the expansion and self renewal of hematopoietic stem progenitor cells (HSPC) ex vivo and in vivo, and uses thereof for.

Embodiments of the present invention are based on the discovery that small hairpin RNAs or short hairpin RNAs (shRNA) that target six proteins, when transduced into isolated primary HSPCs, increased the colony forming capacity and the long term culture forming capacity of the HSPCs. The transduced isolated primary HSPCs scored two- to five-fold higher in a standard methylcellulose colony forming cell assay (CFC) and over 100 fold higher in a standard long term culture initiating cell assay (LTC-IC). The target six proteins are exostoses 1 (EXT1), phospholipase C zeta 1 (PLCZ1); serine threonine kinase 38 (STK38); protein tyrosine phosphatase, non-receptor type 9 (PTPN9); egl nine homolog 3 (EGLN3); mutL homolog 1 (MLH1); and ATP-binding cassette, sub-family C(CFTR/MRP), member 12 (ABCC12). Accordingly, inhibiting the protein activity and/or the protein expression of EXT1, STK38, PTPN9, EGLN3, MLH1, and/or ABCC12 lead to increased expansion of HSCs.

Accordingly, in one embodiment, provided herein is a method for expanding ex vivo a population of hematopoietic stem progenitor cells (HSPCs), the method comprising contacting an isolated cell population comprising an HSPC with an RNAi agent which comprises at least 15 contiguous nucleotides differing by no more than 3 nucleotides from SEQ ID NO: 9.

In one embodiment, described herein is a method for promoting hematopoietic stem progenitor cell (HSPC) self renewal ex vivo, the method comprising contacting an isolated cell population comprising an HSPC with an RNAi agent which comprises at least 15 contiguous nucleotides differing by no more than 3 nucleotides from SEQ ID NO: 9.

In one embodiment, described herein is a method for promoting hematopoietic stem progenitor cell (HSPC) expansion in a subject, comprising administering a therapeutically effective amount of a pharmaceutical composition comprising at least one RNAi agent and a pharmaceutically acceptable carrier, wherein the RNAi agent which comprises at least 15 contiguous nucleotides differing by no more than 3 nucleotides from SEQ ID NO: 9.

In one embodiment, described herein is a method of treating anemia in a subject in need thereof, the method comprising administering a therapeutically effective amount of a pharmaceutical composition comprising at least one RNAi agent and a pharmaceutically acceptable carrier, wherein the RNAi agent which comprises at least 15 contiguous nucleotides differing by no more than 3 nucleotides from SEQ ID NO: 9.

In one embodiment, described herein is a method for transplanting a population of hematopoietic stem progenitor cells (HSPCs), the method comprising: (a) contacting an isolated cell population comprising an HSPC with a RNAi agent which comprises at least 15 contiguous nucleotides differing by no more than 3 nucleotides from SEQ ID NO: 9; (b) culturing ex vivo the HSPC from step (a); and (c) implanting the cultured HSPC from step (b) into a subject. In one embodiment, the HSPC in step (b) is cultured for at least 20 days before step (c).

In one embodiment, described herein is a use of a RNAi agent for transplanting a population of hematopoietic stem progenitor cells (HSPCs), the use comprising: (a) contacting an isolated cell population comprising an HSPC with a RNAi agent which comprises at least 15 contiguous nucleotides differing by no more than 3 nucleotides from SEQ ID NO: 9; (b) culturing ex vivo the HSPC from step (a); and (c) implanting the cultured HSPCs from step (b) into a subject. In one embodiment, the HSPC in step (b) is cultured for at least 20 days before step (c).

In one embodiment, described herein is a method for expanding ex vivo a population of hematopoietic stem progenitor cells (HSPCs), the method comprising contacting an isolated cell population comprising an HSPC with an agent which inhibits serine threonine kinase 38 (STK38).

In one embodiment, described herein is a method for promoting hematopoietic stem progenitor cell (HSPC) self renewal ex vivo, the method comprising contacting an isolated cell population comprising an HSPC with an agent which inhibits serine threonine kinase 38 (STK38).

In one embodiment, described herein is a method for promoting hematopoietic stem progenitor cell (HSPC) expansion in a subject, comprising administering a therapeutically effective amount of a pharmaceutical composition comprising an agent that inhibits serine threonine kinase 38 (STK38).

In one embodiment, described herein is a method of treating anemia in a subject in need thereof, the method comprising administering a therapeutically effective amount of a pharmaceutical composition comprising an agent that inhibits serine threonine kinase 38 (STK38).

In another embodiment, described herein is a method for transplanting a population of hematopoietic stem progenitor cells (HSPCs), the method comprising: (a) contacting an isolated cell population comprising an HSPC with an agent which inhibits serine threonine kinase 38 (STK38); (b) culturing ex vivo the HSPC from step (a); and (c) implanting the cultured HSPC from step (b) into a subject. In one embodiment, the HSPC in step (b) is cultured for at least 20 days before step (c).

In another embodiment, described herein is a use of an agent which inhibits serine threonine kinase 38 (STK38) for transplanting a population of hematopoietic stem progenitor cells (HSPCs), the use comprising: (a) contacting an isolated cell population comprising an HSPC with an agent which inhibits serine threonine kinase 38 (STK38); (b) culturing ex vivo the HSPC from step (a); and (c) implanting the cultured HSPC from step (b) into a subject. In one embodiment, the isolated cell population comprising an HSPC from step (b) is cultured for at least 20 days before step (c).

In one embodiment, the agent inhibits the activity of STK38. In one embodiment, the agent that inhibits the protein activity of STK38 is a small molecule, nucleic acid, nucleic acid analogue, protein, antibody, peptide, aptamer or variants or fragments thereof. In some embodiments, the agent that inhibits the protein activity of STK38 is a small molecule, for example but not limited to a small molecule reversible, an inhibiting antibody or functional fragments thereof or irreversible inhibitor of STK38 protein.

Anemia generally means a red cell mass corresponding to less than about $4.0 \times 10^{12}$ red cells/L in adult females and less than about $4.5 \times 10^{12}$ red cells/L in adult males (a hemoglobin level of less than about 12.0 g/dL in adult females and less than about 13.5 g/dL in adult males). Anemia may occur as a result of bleeding (including internal), hemolysis, kidney disease, leukemia, multiple myeloma, bone marrow failure, erythropoietin deficiency, or deficiencies in iron, folate, vitamin B12, or vitamin B6.

It is also contemplated that the methods and compositions described herein can be used in any situations in which a bone marrow transplantation or a blood transfusion is needed in a subject; such as in cancer treatment after chemotherapy. These situations constitute occasions when there is a need for increased or replacement HSPCs and numbers, or an increase in blood cells in a subject.

The RBCs count is also a part of the complete blood count test (CBC) routinely ordered by physicians. A sample of peripheral blood can be collected and mixed with anticoagulant. For RBC counting by the manual visual method, a small, fixed volume of blood is diluted, applied to a hemacytometer and counted under a microscope. Alternatively, RBCs are counted with automated cell counters that are commercially available.

In one embodiment, a host needing treatment for anemia can be any animal that has RBCs (erythrocytes), and the RBCs are differentiated from hematopoietic stem progenitor cells. In one embodiment, the subject is a mammal, such as a dog, cat, horse, and monkey, preferably a human.

In one embodiment, the agent is an RNAi agent that inhibits gene expression of STK38. The RNAi agent silences the gene expression of STK38.

For example, the RNAi agent can comprise CAGCAAGGGCCATGTGAAACT (SEQ ID NO. 9), CAGCAAGGGCCATGTGA (SEQ ID NO. 21), GCAAGGGCCATGTGA (SEQ ID NO. 22), GGGCCATGTGAAACT (SEQ ID NO. 23), AGCAAGGGCCATGTGAAAC (SEQ ID NO. 24), AAGGGCCATGTGAAAC (SEQ ID NO. 25), AGCAAGGGCCATGTGAAACT (SEQ ID NO. 26), CAGCAAGGGCCATGTGAAAC(SEQ ID NO. 27), CAGCAAGGGCCATGTGAAAC (SEQ ID NO. 28), CAGGAAGGGCCATCTGA (SEQ ID NO. 29), GCATGGGCCATCTGA (SEQ ID NO. 30), GGGCCATCTGAAACT (SEQ ID NO. 31), AGCATGGGCCATGTGAAAG (SEQ ID NO. 32), AAGGGCCATGTGATAC (SEQ ID NO. 33), AGCAACGGCCATGTGAAACT (SEQ ID NO. 34), CAGCATGGGCCATGTGAAAC (SEQ ID NO. 35), CAGCATGGGCCATGTGAAAC (SEQ ID NO. 36), and the like. Depending on whether the RNAi agent is a deoxyribonucleic acid (DNA) or a ribonucleic acid (RNA), the RNAi agent can have thymidine (T) or uridine (U) nucleotide bases respectively.

In one embodiment, the RNAi agent comprises a double-stranded ribonucleic acid (dsRNA) wherein the dsRNA comprises a sense strand and an antisense strand, wherein the antisense strand comprising a region of complementarity to and have at least 15 contiguous nucleotides differing by no more than 3 nucleotides from SEQ ID NO: 9. In one embodiment, the RNAi agent comprises SEQ ID NO: 9. In one embodiment, the antisense strand comprises a region of complementarity to SEQ ID NO: 9. In one embodiment, the sense strand comprises SEQ ID NO: 9.

Changes in gene expression of STK38 can be assessed by analyzing the amount of the protein, for example, by western blot analyses; or by studying the mRNA of the gene by, for example, quantitative RT-PCR (qRT-PCR). Such methods are well known in the art, e.g. as disclosed in "Current Protocols of Molecular Biology" and also disclosed herein using the primers SED ID No 19 and 20. Antibodies for STK38 can be obtained from commercial sources such as SIGMA-ALDRICH®, R&D SYSTEMS® and ABCAM®.

In all embodiments, the cell population comprising an HSPC contacted with the agent or RNAi agent exhibits at least a 2 fold increase in colony formation capacity when compared to an isolated cell population comprising an HSPC that is not contacted with the agent or RNAi agent. The isolated cell population comprising an HSPC that is not contacted with the agent or RNAi agent functions as a control or reference. In some embodiments, the colony formation capacity is increased by at least 3 fold, at least 4 fold, at least 5 fold, at least 5 fold, at least 6 fold, at least 7 fold, at least 8 fold, at least 9 fold, or at least 10 fold, when compared to a control isolated cell population comprising an HSPC. The colony formation capacity can be determined in culture by a standard methylcellulose colony forming cell assay (CFC) that is well known in the art and is described herein. The control isolated cell population comprising an HSPC that is used for the comparison is an HSPC that is contacted with only the buffer or vehicle in which the agent or RNAi agent is solubilized/suspended/dissolved in. For example, if the agent or RNAi agent is dissolved in phosphate buffered saline (PBS), then the vehicle is PBS. In this example, the control isolated cell population comprising an HSPC is contacted with PBS and the HSPC to be expanded by the method described herein is contacted with a PBS solution containing the agent or RNAi agent. For comparison purposes, the method of contacting and contact time for both groups of HSPCs, HSPCs contacted with and HSPCs not contacted with an agent or RNAi agent, are kept the same.

In one embodiment, promoting of HSPCs self renewal ex vivo is to increase the self renewal capability of the isolated HSPCs ex vivo. An increase in the self renewal capability of the isolated HSPCs ex vivo can be determined by a long-term culture colony initiating cell assay (LTC-IC) assay.

In one embodiment, the RNAi agent when contacted and/or transduced into an isolated cell population comprising an HSPC produces HSPCs that exhibit at least a 5 fold increase in long-term culture colony formation capacity when compared to an isolated cell population comprising an HSPC that is not contacted with the agent or RNAi agent.

In one embodiment of the methods disclosed herein, the isolated cell population comprising an HSPC exhibits at least a 5 fold increase in long-term culture colony formation capacity when compared to an isolated cell population comprising an HSPC that is not contacted with the agent or RNAi agent. In some embodiments, the increase in long-term culture colony formation capacity is at least 6 fold, at least 7 fold, at least 8 fold, at least 9 fold, at least 10 fold, at least 11 fold, at least 12 fold, at least 13 fold, or more fold, when compared to a control isolated cell population comprising an HSPC. The long-term culture colony formation capacity can determined in culture by a standard LTC-IC assay by limited dilution assay (LDA) that is well known is the art and is described herein. The control isolated cell population comprising an HSPC that is used for the comparison is an HSPC that is contacted with only the buffer or vehicle in which the agent or RNAi agent is solubilized/suspended/dissolved in. For example, if the RNAi agent is dissolved in 0.1 M Tris-HCL EDTA pH 8.0 buffer (1×TE), then the buffer is 1×TE. In this example, the control isolated cell population comprising an HSC is contacted with 1×TE and the HSC to be expanded by the method described herein is contacted with a 1×TE solution containing the RNAi agent. For comparison purposes, the method of contacting and the contact time for both groups of HSPCs, HSPCs contacted with and HSPCs not contacted with an agent or RNAi agent, are kept the same.

In one embodiment, described herein is a method for expanding ex vivo a population of hematopoietic stem progenitor cells (HSPCs), the method comprising contacting an isolated cell population comprising an HSPC with an agent which inhibits a protein selected from the group consisting of exostoses 1 (EXT1), phospholipase C zeta 1 (PLCZ1), protein tyrosine phosphatase, non-receptor type 9 (PTPN9), egl nine homolog 3 (EGLN3), mutL homolog 1 (MLH1) and ATP-binding cassette sub-family C(CFTR/MRP), member 12 (ABCC12).

In another embodiment, described herein is a method for expanding ex vivo a population of hematopoietic stem progenitor cells (HSPCs), the method comprising contacting an isolated cell population comprising an HSPC with an agent which inhibits a protein selected from the group consisting essentially of exostoses 1 (EXT1), phospholipase C zeta 1 (PLCZ1), protein tyrosine phosphatase, non-receptor type 9 (PTPN9), egl nine homolog 3 (EGLN3), mutL homolog 1 (MLH1) and ATP-binding cassette sub-family C(CFTR/MRP), member 12 (ABCC12).

In one embodiment, described herein is a method for promoting hematopoietic stem progenitor cell (HSPC) expansion in a subject, comprising administering a therapeutically effective amount of a pharmaceutical composition comprising an agent which inhibits a protein selected from the group consisting of exostoses 1 (EXT1), phospholipase C zeta 1 (PLCZ1), protein tyrosine phosphatase, non-receptor type 9 (PTPN9), egl nine homolog 3 (EGLN3), mutL homolog 1 (MLH1) and ATP-binding cassette sub-family C(CFTR/MRP), member 12 (ABCC12).

In another embodiment, described herein is a method for promoting hematopoietic stem progenitor cell (HSPC) expansion in a subject, comprising administering a therapeutically effective amount of a pharmaceutical composition comprising an agent which inhibits a protein selected from the group consisting essentially of exostoses 1 (EXT1), phospholipase C zeta 1 (PLCZ1), protein tyrosine phosphatase, non-receptor type 9 (PTPN9), egl nine homolog 3 (EGLN3), mutL homolog 1 (MLH1) and ATP-binding cassette sub-family C (CFTR/MRP), member 12 (ABCC12).

In one embodiment, described herein is a method for transplanting a population of hematopoietic stem progenitor cells (HSPCs), the method comprising: (a) contacting an isolated cell population comprising an HSPC with at least one an agent which inhibits a protein selected from the group consisting of exostoses 1 (EXT1), phospholipase C zeta 1 (PLCZ1), protein tyrosine phosphatase, non-receptor type 9 (PTPN9), egl nine homolog 3 (EGLN3), mutL homolog 1 (MLH1) and ATP-binding cassette sub-family C(CFTR/MRP), member 12 (ABCC12); (b) culturing ex vivo the isolated cell population comprising an HSPC from step (a); and (c) transplanting the cultured HSPC from step (b) into a subject.

In another embodiment, described herein is a method for transplanting a population of hematopoietic stem progenitor cells (HSPCs), the method comprising: (a) contacting an isolated cell population comprising an HSPC with at least one an agent which inhibits a protein selected from the group consisting essentially of exostoses 1 (EXT1), phospholipase C zeta 1 (PLCZ1), protein tyrosine phosphatase, non-receptor type 9 (PTPN9), egl nine homolog 3 (EGLN3), mutL homolog 1 (MLH1) and ATP-binding cassette sub-family C (CFTR/MRP), member 12 (ABCC12); (b) culturing ex vivo the isolated cell population comprising an HSPC from step (a); and (c) transplanting the cultured HSPC from step (b) into a subject.

In one embodiment, the isolated cell population comprising an HSPC in step (b) is cultured for at least 20 days.

In one embodiment, the isolated cell population comprising an HSPC exhibits at least a 5 fold increase in long-term culture colony formation capacity when compared to an isolated cell population comprising an HSPC that is not contacted with the agent.

In one embodiment, the agent inhibits the activity of a protein or the function of a protein selected from the group consisting of EXT1, PTPN9, EGLN3, MLH1, and ABCC12. In another embodiment, the agent inhibits the activity of a protein selected from the group consisting essentially of EXT1, PTPN9, EGLN3, MLH1, and ABCC12. In one embodiment, the agent inhibits the activity of EXT1, PTPN9, EGLN3, MLH1 or ABCC12. In one embodiment, the agent that inhibits the protein activity of EXT1, PTPN9, EGLN3, MLH1, and ABCC12 is a small molecule, nucleic acid, nucleic acid analogue, protein, antibody, peptide, aptamer or variants or fragments thereof. In some embodiments, the agent that inhibits the protein activity of EXT1, PTPN9, EGLN3, MLH1, and ABCC12 is a small molecule, for example but not limited to a small molecule reversible or irreversible inhibitor of EXT1, PTPN9, EGLN3, MLH1, and ABCC12 protein. At a minimum, when the activity or functions of these proteins are inhibited, the HSPCs exhibit at least a 2 fold increase in their CFC capability and/or at least a 5 fold increase in their LTC-IC capability.

In some embodiments, combinations of agents that inhibit the activity of a protein selected from the group consisting of EXT1, PTPN9, EGLN3, MLH1, and ABCC12 can be contacted with the HSPC in the methods disclosed herein.

In some embodiments, the pharmaceutical composition comprises combinations of agents that inhibit the activity or function of a protein selected from the group consisting of EXT1, PTPN9, EGLN3, MLH1, and ABCC12.

In one embodiment, the agent is an RNAi agent that inhibits the gene expression of EXT1, PTPN9, EGLN3, MLH1 or ABCC12.

In some embodiments, combinations of agents that inhibit the gene expression of EXT1, PTPN9, EGLN3, MLH1, and ABCC12 can be contacted with the HSPC in the methods disclosed herein.

In some embodiments, the pharmaceutical composition comprises combinations of agents that inhibit the gene expression of EXT1, PTPN9, EGLN3, MLH1, and ABCC12.

It is also contemplated that various combinations of agents that inhibit the gene expression of and/or inhibit the activity of EXT1, PTPN9, EGLN3, MLH1, and ABCC12, and an RNAi agent comprising SEQ. ID. NO. 9 can be contacted with the HSPC in the methods disclosed herein.

It is also contemplated that the pharmaceutical composition can comprise various combinations of agents that inhibit the gene expression of and/or inhibit the activity of EXT1, PTPN9, EGLN3, MLH1, and ABCC12, and an RNAi agent comprising SEQ. ID. NO. 9.

In one embodiment, the RNAi agent comprises a double-stranded ribonucleic acid (dsRNA) wherein the dsRNA comprises a sense strand and an antisense strand, wherein the antisense strand comprising a region of complementarity to and have at least 15 contiguous nucleotides that differ by no more than 3 nucleotides from a sequence selected from the group consisting of SEQ ID NOS: 2, 5, 8, 16, 17, and 18. In one embodiment, the antisense strand comprises a region of complementarity to a sequence selected from the group consisting of SEQ ID NOS: 2, 5, 8, 16, 17, and 18. In one embodiment, the sense strand comprises a sequence selected from the group consisting of SEQ ID NOS: 2, 5, 8, 16, 17, and 18. In some embodiments, the RNAi agent is an shRNA that comprises a sequence selected from the group consisting of SEQ ID NOS: 2, 5, 8, 16, 17, and 18.

In one embodiment, described herein is a method for expanding ex vivo a population of hematopoietic stem progenitor cells (HSPCs), the method comprising contacting an isolated cell population comprising an HSPC with at least one RNAi agent which comprises at least 15 contiguous nucleotides differing by no more than 3 nucleotides from a sequence selected from the group consisting of SEQ ID NOS: 2, 5, 8, 16, 17, and 18.

In another embodiment, described herein is a method for promoting hematopoietic stem progenitor cell (HSPC) expansion in a subject, comprising administering a therapeutically effective amount of a pharmaceutical composition comprising at least one RNAi agent and a pharmaceutically acceptable carrier, wherein the RNAi agent comprises at least 15 contiguous nucleotides differing by no more than 3 nucleotides from a sequence selected from the group consisting of SEQ ID NOS: 2, 5, 8, 16, 17, and 18.

In one embodiment, described herein is a method for transplanting a population of hematopoietic stem progenitor cells (HSPCs), the method comprising: (a) contacting an isolated cell population comprising an HSPC with at least one RNAi agent which comprises at least 15 contiguous nucleotides differing by no more than 3 nucleotides from a sequence selected from the group consisting of SEQ ID NOS: 2, 5, 8, 16, 17, and 18; (b) culturing ex vivo the isolated cell population comprising an HSPC from step (a); and (c) implanting the cultured HSPC from step (b) into a subject.

In one embodiment, the isolated cell population comprising an HSPC in step (b) is expanded for at least 20 days.

In one embodiment, the at least one RNAi agent comprises a double-stranded ribonucleic acid (dsRNA) wherein the dsRNA comprises a sense strand and an antisense strand, wherein the antisense strand comprising a region of sequence complementarity to and have at least 15 contiguous nucleotides that differ by no more than 3 nucleotides from a sequence selected from the group consisting of SEQ ID NOS: 2, 5, 8, 16, 17, and 18. In one embodiment, the antisense strand comprises a region of complementarity to a sequence selected from the group consisting of SEQ ID NOS: 2, 5, 8, 16, 17, and 18. In one embodiment, the sense strand comprises a sequence selected from the group consisting of SEQ ID NOS: 2, 5, 8, 16, 17, and 18. In some embodiments, the RNAi agent is an shRNA that comprises a sequence selected from the group consisting of SEQ ID NOS: 2, 5, 8, 16, 17, and 18. In one embodiment, the sense strand comprises is SEQ ID NO: 2. In one embodiment, the sense strand comprises is SEQ ID NO: 5. In one embodiment, the sense strand comprises is SEQ ID NO: 8. In one embodiment, sense strand comprises SEQ ID NO: 16. In one embodiment, the sequence is SEQ ID NO: 17. In one embodiment, the sequence is SEQ ID NO: 18.

In one embodiment, the RNAi agent inhibits gene expression of EXT1 and the RNAi agent comprises SEQ ID NO: 2.

In one embodiment, the RNAi agent inhibits gene expression of EXT1 and the RNAi agent comprises SEQ ID NO: 5.

In one embodiment, the RNAi agent inhibits gene expression of PTPN9 and the RNAi agent comprises SEQ ID NO: 8.

In one embodiment, the RNAi agent inhibits gene expression of EGLN3 and the RNAi agent comprises SEQ ID NO: 16.

In one embodiment, the RNAi agent inhibits gene expression of MLH1 and the RNAi agent comprises SEQ ID NO: 17.

In one embodiment, the RNAi agent inhibits gene expression of ABCC12 and the RNAi agent comprises SEQ ID NO: 18.

In one embodiment, described herein is a nucleic acid molecule, comprising a sequence that is or greater in identity, i.e. at least about 80% identical, to any one of the group consisting of SEQ ID NOS: 2-18.

In one embodiment, described herein is a nucleic acid molecule, comprising a sequence that is 85% or greater in identity, i.e. at least about 85% identical, to any one of the group consisting of SEQ ID NOS: 2-18.

In one embodiment, described herein is a nucleic acid molecule, comprising a sequence that is 90% or greater in identity, i.e. at least about 90% identical, to any one of the group consisting of SEQ ID NOS: 2-18.

In one embodiment, described herein is a nucleic acid molecule, comprising a sequence that is 95% or greater in identity, i.e. at least about 95% identical, to any one of the group consisting of SEQ ID NOS: 2-18.

In one embodiment, described herein is a nucleic acid molecule, comprising a sequence that is 99% or greater in identity, i.e. at least about 99% identical, to any one of the group consisting of SEQ ID NOS: 2-18.

In one embodiment, described herein is a nucleic acid molecule, comprising a sequence that is identical to any one of the group consisting of SEQ ID NOS: 2-18.

In one embodiment, the nucleic acid molecule is a sequence from any one of the group consisting of SEQ ID NOS: 2-7.

In one embodiment, the nucleic acid molecule is a sequence from any one of the group consisting of SEQ ID NOS: 9-15.

In one embodiment, the nucleic acid molecule has the sequence of SEQ ID NO: 9.

In some embodiments of the methods disclosed herein, the RNAi agent is a short interfering RNA (siRNA), double-stranded RNA (dsRNA), micro-RNA, short hairpin RNA (shRNA), short interfering oligonucleotide, short interfering nucleic acid, or precursors or derivatives thereof. In some embodiments, the RNAi agent is a vector. In some embodiments, the RNAi agent is an expression vector. In other embodiments, the RNAi agent is a viral vector, such as a lentivirus or adenovirus.

Changes in gene expression of a protein can be assessed by studying the protein, for example, by western blot analyses; or by studying the mRNA of the gene by quantitative RT-PCR (qRT-PCR). Such methods are well known in the art, e.g. as described in "Current Protocols of Molecular Biology" and also described herein. Antibodies for the any of proteins described herein can be obtained from commercial sources such as SIGMA-ALDRICH®, R&D SYSTEMS® and ABCAM®. One skilled in the art would be able to access the publicly available mRNA sequence of EXT1, STK38, PTPN9, EGLN3, MLH1, and ABCC12 on GENBANK™ and design PCR primers for qRT-PCR.

In some embodiments, the methods are such that the isolated cell population comprising an HSPC can be contacted with more than one agent or RNAi agent or combinations thereof. In one embodiment, the isolated cell population comprising an HSPC is contacted with two agents and/or two RNAi agents. In one embodiment, the isolated cell population comprising an HSPC is contacted with three agents and/or RNAi agents. In some embodiments, the pharmaceutical composition can comprise more that one agent or RNAi agent or combinations thereof. In one embodiment, the pharmaceutical composition comprises two agents and/or two RNAi agents. In one embodiment, the pharmaceutical composition comprises three agents and/or RNAi agents. A variety of combinations of agents and RNAi agents and combinations of the numbers of agents and RNAi agents are contemplated. The agents and the RNAi agents can all target the same protein or different proteins. For example, the combinations can be: an agent inhibiting EXT1 activity and an RNAi agent comprising SEQ ID NO: 9; an RNAi agent comprising SEQ. ID. NO: 2, and an RNAi agent comprising SEQ. ID. NO: 9; an RNAi agent comprising SEQ. ID. NO: 2, an RNAi agent comprising SEQ. ID. NO: 9, and an RNAi agent comprising SEQ. ID. NO: 18; an inhibiting antibody to EXT1 activity, an RNAi agent comprising SEQ. ID. NO: 9, and an RNAi agent comprising SEQ. ID. NO: 16; an inhibiting antibody to EXT1 activity, an RNAi agent comprising SEQ. ID. NO: 9, and an agent inhibiting PLCZ1 activity; an RNAi agent comprising SEQ. ID. NO: 2, an RNAi agent comprising SEQ. ID. NO: 5, an RNAi agent comprising SEQ. ID. NO: 9; an inhibiting antibody to STK38 activity; an inhibiting antibody to EXT1 activity and an RNAi agent comprising SEQ. ID. NO: 9.

In one embodiment, the RNAi agent when contacted and/or transduced into an isolated cell population comprising an HSPC produces HSPCs that exhibit at least a 2 fold increase in colony formation capacity when compared to an isolated cell population comprising an HSPC that is not contacted with the agent or RNAi agent.

In all embodiments of the methods disclosed herein, the isolated cell population comprising an HSPC contacted with the agent or RNAi agent exhibits at least a 2 fold increase in colony formation capacity when compared to an isolated cell population comprising an HSPC that is not contacted with the agent or RNAi agent. The isolated cell population comprising an HSPC that is not contacted with the agent or RNAi agent functions as a control. In some embodiments, the colony formation capacity is increased by at least 3 fold, at least 4 fold, at least 5 fold, at least 5 fold, at least 6 fold, at least 7 fold, at least 8 fold, at least 9 fold, or at least 10 fold, when compared to a control isolated cell population comprising an HSPC. The colony formation capacity can be determined in culture by a standard methylcellulose colony forming cell assay (CFC) that is well known is the art and is described herein. The control isolated cell population comprising an HSPC that is used for the comparison is an HSPC that is contacted with only the buffer or vehicle in which the agent or RNAi agent is solubilized/suspended/dissolved in, for example, if the agent or RNAi agent is dissolved in phosphate buffer saline (PBS), then the vehicle is PBS. In this example, the control isolated cell population comprising an HSPC is contacted with PBS and the HSPC to be expanded by the method described herein is contacted with a PBS solution containing the agent or RNAi agent. For example, if the RNAi agent is dissolved in 0.1 M Tris-HCL EDTA pH 8.0 buffer (1×TE), then the buffer is 1×TE. In this example, the control isolated cell population comprising an HSPC is contacted with 1×TE and the HSC to be expanded by the method described herein is contacted with a 1×TE solution containing the RNAi agent. For comparison purposes, the contact time for both groups of HSPCs, contacted with and not contacted with an agent or RNAi agent, are the kept the same.

In some embodiments of the methods disclosed herein, the isolated cell population comprising an HSPC contacted with the agent or RNAi agent exhibits at least a 2 fold increase in the percent of CFU-erythroid (CFU-E) and burst-forming units erythroid (BFU-E) formed when compared to a control isolated cell population comprising an HSPC. In some embodiments, the increase in percent of CFU-erythroid (CFU-E) and burst-forming units erythroid (BFU-E) formed is at least 3 fold, at least 4 fold, at least 5 fold, at least 5 fold, at least 6 fold, at least 7 fold, at least 8 fold, at least 9 fold, or at least 10 fold, when compared to a control isolated cell population comprising an HSPC. The increase in percent of CFU-erythroid (CFU-E) and burst-forming units erythroid (BFU-E) formed in culture can be determined by visual assessment of the morphology of the colonies formed. The morphologies of the various colonies derived from HSPCs are well known in the art, e.g. CFU-granulocyte-macrophage (CFU-GM), CFU-erythroid (CFU-E), and burst-forming units erythroid (BFU-E). The morphologies are also described herein. One skilled in the art would be able to identify the types of colony, count the total number of colonies and count the numbers of CFU-E and BFU-E colonies. The percent of CFU-E/BFU-E is calculated by the formula:

$$\text{Percent of } CFU\text{-}E/BFU\text{-}E = \frac{\text{numbers of } CFU\text{-}E \text{ and } BFU\text{-}E}{\text{total number of colonies}}$$

In some embodiments of the methods disclosed herein, the method is such that the isolated cell population comprising an HSPC contacted with the at least one RNAi agent exhibits at least a 5 fold increase in long term culture colony formation capacity when compared to an isolated cell population comprising an HSPC that is not contacted with the RNAi agent. The isolated cell population comprising an HSPC that is not contacted with the agent or RNAi agent functions as a control. In some embodiments, the increase in long-term culture colony formation capacity is at least 6 fold, at least 7 fold, at least 8 fold, at least 9 fold, at least 10 fold, at least 11 fold, at least 12 fold, at least 13 fold, or more fold, when compared to a control isolated cell population comprising an HSPC. The in long-term culture colony formation capacity can determined in culture by a standard LTC-IC assay by limited dilution assay (LDA) that is well known is the art and is described herein.

In the methods disclosed herein, expanding HSPC or expansion of HSPC means increasing or multiplying the number of cells. For example, with a starting number of $1 \times 10^3$ HSPCs, contacting these HSPCs with an agent or an RNAi agent disclosed herein produces a number of HSPCs that is greater than $1 \times 10^3$ HSPCs after a period of several weeks in culture, for example, at least twice the number of original number of cells. This is achieved because the HSPCs that have been contacted with an agent inhibitor or an RNAi agent disclosed herein have increased colony formation cell (CFC) capacity. A single HSPC with increased CFC capacity undergoes multiple cell divisions and thereby multiplies the cell number.

In some embodiments of the methods described herein, the isolated cell population comprising an HSPC is contacted with the RNAi agent by simply mixing the RNAi agent with the HSPC in solution; usually the RNAi agent is added into the culture medium of the HSPC. The culture medium with the RNAi agent is then added to the HSPCs. For example, siRNA, dsRNA, micro-RNA, shRNA, short interfering oligonucleotide, short interfering nucleic acid, precursors or derivatives thereof, a vector, an expression vector, a lentivirus or adenovirus is added to the culture medium of a culture dish containing the HSPCs. In other embodiments, the RNAi agent is mixed with other carriers, such as polymers, PEG, fusion PTD-DRBD protein, and added to the HSPCs. For example, where the RNAi agent is an expression vector, it can be mixed with transfection reagents such as LIPOFECTAMINE®. Such transfection reagents help the RNAi agent enter the cells.

In one embodiment, the expression vector can be a virus such as an adenovirus, an adeno-associated virus, or lentivirus, for example, MDH.xdna murine retroviral vector. Viral vectors provide an additional advantage of ease of transducing the HSPCs by viral infection. In another embodiment, the expression vector is a non-viral vector. Such vectors can be transfected into HSPCs using known transfection methods known in the art, such as cationic lipid transfection as disclosed herein.

In vitro transfection of isolated cell population comprising an HSPC can be accomplished by any transfection methods known in the art, for example, calcium phosphate-mediated, DEAE-Dextran-mediated, calcium alginate microbeads, cationic lipid-mediated, scrape-loading, and ballistic bombardment with nucleic acid gold particles. In one embodiment, isolation and culturing of progenitor cells is performed using the methods well known in to those skilled in the art, e.g. as described in U.S. Pat. Nos. 5,199,942, 5,474,687, 5,589,368, 5,612,211, 5,905,041, 6,355,237, and 7,345,025, which are hereby incorporated by reference in their entirety. The identity of the isolated HSPCs can be confirmed by transglutaminase expression in culture as described in WO2000/006766, which is also hereby incorporated by reference in its entirety. After in vitro transfection, the transfected HSPCs can be expanded in culture according to methods described in U.S. Pat. Nos. 5,744,361, 5,905,041, and 6,326,198, which are hereby incorporated by reference in their entirety. In some embodiments of the methods disclosed herein, the expanded HSPCs can then be transplanted into the subject. Transplantations of HSPCs are described in U.S. Pat. Nos. 5,817,773, 5,858,782, and U.S. patent application Ser. No. 10/730,334 which are incorporated herein by reference in their entirety.

In one embodiment of any of the methods disclosed herein, the method comprises stimulating the ex vivo expansion of the isolated cell population comprising HSPCs before contacting with the agent or RNAi agent. Stimulation of ex vivo expansion of an isolated cell population comprising HSPCs can be achieved with, for example, angiopoietin-like 5, IGFBP2, insulin-like growth factor-binding protein 2, and prostaglandin D2 (Zhang C C, et al., Nat. Med. 2006, 12:240-5; Zhang C C, et al., Blood. 2008, 111:3415-23; Huynh H, et al., Stem Cells. 2008, 26:1628-35; North T E, et al., Nature. 2007, 447:1007-11). Methods of expanding stem cells in vitro are known in the art, e.g. as described in U.S. Pat. Nos. 5,728,581; 5,908,784 and U.S. Patent Application 2004/0018620; 2005/072147; and 2009/0148420. These references are incorporated herein by reference in their entirety.

In one embodiment, after the HSPCs have contacted the agent or RNAi agent disclosed herein, the HSPCs are grown in culture for a period of at least 1 week, at least 2 weeks, at least 3 weeks, at least 4 weeks, at least 5 weeks, at least 6 weeks, at least 7 weeks, at least 8 weeks, at least 9 weeks, at least 10 weeks, at least 11 weeks, at least 12 weeks, or even more weeks. Routine change of culture media is exercised. In some embodiments, at any time during the culture periods post contacting with the agent or RNAi agent disclosed herein, the expanded HSPCs can be harvested and cryopreserved for storage purposes. In some embodiments, at any time during the culture periods post contacting with the agent or RNAi agent disclosed herein, the expanded HSPCs can be harvested and used, e.g. in clinical research or medical treatment such as implanting into a subject. Preferably, the expanded HSPCs are harvested after no less than two weeks in culture after contacting with the agent or RNAi agent disclosed herein.

The methods disclosed herein are applicable to any situations wherein a greater amount of HSPC is desired, in clinical research, for drug discovery or for engraftment in human hematopoietic stem cell transplantation to rescue patients after cytoablative therapies. For example, in bone marrow transplant, it is known that the higher the amount of HSPCs implanted into a recipient, the greater percentage of engraftment of the donor HSPCs in the recipient. While there are methods for increasing mobilization of HSPCs cells into circulation from the bone marrow, the methods disclosed herein can be used in conjunction with the mobilization methods to increase the amount of circulating HSPCs and the HSPCs in the bone marrow of the donor prior to harvesting. In addition, the methods disclosed herein can be used to increase the amount of HSPCs after the cells are harvested from a donor but before to cells are transplanted into the recipient. The HSPCs harvested from a donor are initially cultured ex vivo and expanded in culture by the methods disclosed herein. When the number of HSPCs has reached a desired amount, the cultured HSPCs can be harvested and implanted into the recipient.

In one embodiment, the HSPCs are isolated from a subject, contacted with an agent or RNAi agent disclosed herein, cultured to expand in numbers, harvested and transplanted back into the same subject, i.e. an autologous cell transplant. In another embodiment, the HSPCs are isolated from a donor who is an HLA-type match with a recipient subject wherein the donor and recipient are two separate individuals. This is allogeneic transplantation. Donor-recipient antigen type-matching is well known in the art. The HLA-types include HLA-A, HLA-B, HLA-C, and HLA-D. These represent the minimum number of cell surface antigen matching required for transplantation.

In one embodiment, the isolated cell population comprising an HSPC is cryopreserved before being contacted with the agent or RNAi agent. The HSPC is initially harvested from a donor and cryopreserved. Preferably HLA type and blood group information of the donor are recorded and cataloged with the frozen HSPCs. It is contemplated that a "bank" of HSPCs can be produced, wherein all samples of HSPCs are cataloged by HLA type and blood group. When HSPCs of a certain HLA type and blood group is needed, the frozen HSPCs can be thawed and expanded ex vivo by the methods disclosed herein. The expanded HSPCs are then collected and used, e.g. for implanting into a subject.

In another embodiment, the isolated cell population comprising an HPSC is contacted with the agent or RNAi agent disclosed herein, grown in culture for a period of time, and then the cultured and expanded ex vivo HPSCs are cryopreserved for future use, e.g. implantation into the same donor, the same intended recipient or another recipient. Preferably HLA type and blood group information of the donor are recorded and cataloged with these frozen expanded HSPCs. It is contemplated that a "bank" of expanded HSPCs can be produced, wherein all samples of HSPCs are cataloged by HLA type and blood group.

In one embodiment, described herein is a pharmaceutical composition comprising an isolated cell population comprising an HSPC and a pharmaceutically-acceptable carrier, wherein the HSPC has been contacted with at least one RNAi agent which comprises at least 15 contiguous nucleotides differing by no more than 3 nucleotides from a sequence selected from the group consisting of SEQ ID NOS: 2, 5, 8, 9, 16, 17, and 18, and/or contacted with at least one agent which inhibits a protein selected from the group consisting of EXT1, PLCZ1, PTPN9, EGLN3, MLH1 and ABCC12.

In one embodiment, described herein is a pharmaceutical composition comprising an HSPC and a pharmaceutically-acceptable carrier, wherein the HSPC has been contacted with at least one RNAi agent which comprises at least 15 contiguous nucleotides differing by no more than 3 nucleotides from a sequence selected from the group consisting essentially of SEQ ID NOS: 2, 5, 8, 9, 16, 17, and 18, and/or contacted with at least one agent which inhibits a protein selected from the group consisting of EXT1, PLCZ1, PTPN9, EGLN3, MLH1 and ABCC12.

In one embodiment, the HSPC comprising the pharmaceutical composition is grown in culture for a period of at least 1 week, at least 2 weeks, at least 3 weeks, at least 4 weeks, at least 5 weeks, at least 6 weeks, at least 7 weeks, at least 8 weeks, at least 9 weeks, at least 10 weeks, at least 11 weeks, at least 12 weeks, or even more weeks after contacting with the agent or RNAi agent disclosed herein. Routine change of culture media is exercised. In some embodiments, at any time during the culture periods post contacting with the agent or RNAi agent disclosed herein, the expanded HSPCs can be harvested and cryopreserved for storage purposes. In some embodiments, at any time during the culture periods post contacting with the agent or RNAi agent disclosed herein, the expanded HSPCs can be harvested and used, e.g. in clinical research or medical treatment such as implanting into a subject. Preferably, the expanded HSPCs are harvested after no less than two weeks in culture following contacting with the agent or RNAi agent disclosed herein.

In one embodiment, the HSPC comprising the pharmaceutical composition is a mammalian HSPC.

In one embodiment, the HSPC comprising the pharmaceutical composition has been previously cryopreserved. In one embodiment, the HSPC is cryopreserved prior to contacting with the agent or RNAi agent disclosed herein. In one embodiment, the HSPC was cryopreserved after contacting with the agent or RNAi agent disclosed herein.

In one embodiment, described herein is a method of treating anemia in a host in need thereof, the method comprising administering a pharmaceutical composition comprising an isolated cell population comprising an HSPC disclosed herein and a pharmaceutically-acceptable carrier.

In one embodiment, the method disclosed herein includes monitoring the RBC count of a subject before and after the administration of the agent for treatment of anemia. The RBC count performed before treatment provide the data for a physician to make a diagnosis of anemia and the RBC count also serves as a reference number with which post-treatment RBC counts can be compared. Routine RBC count of samples of peripheral blood should be performed at 1, 2, 3 months or on an ongoing basis, e.g. every two months, following treatment or according to a physician's decision in order to monitor the efficacy of the treatment.

In one embodiment, the method disclosed herein comprises treating anemia in conjunction with other known treatments such as with erythropoietin (EPO) and peptide mimetics of EPO. EPO is a hormone produced by the kidney that promotes the formation of red blood cells in the bone marrow. The kidney cells that make EPO are specialized and are sensitive to low oxygen levels in the blood. These cells release EPO when the oxygen level is low in the kidney. EPO then stimulates the bone marrow to produce more red cells and thereby increase the oxygen-carrying capacity of the blood. EPO is the prime regulator of red blood cell production. Its major functions are to promote the differentiation and development of red blood cells and to initiate the production of hemoglobin, the molecule within red cells that transports oxygen.

Serine/threonine kinase 38 (STK38), GeneID: 11329, GENBANK™ Accession No.: NM_007271.2 (mRNA) and NP_009202.1 (protein) catalyzes the transfer of the gamma-phosphoryl group from ATP to serine/threonine residues on protein substrates. Synonyms of STK38 include NDR, NDR1, NDR1 protein kinase, and nuclear Dbf2-related kinase 1. The NDR subfamily is part of a larger superfamily that includes the catalytic domains of other protein STKs, protein tyrosine kinases, RIO kinases, aminoglycoside phosphotransferase, choline kinase, and phosphoinositide 3-kinase. NDR kinase contains an N-terminal regulatory (NTR) domain and an insert within the catalytic domain that contains an auto-inhibitory sequence. Like many other AGC kinases, NDR kinase requires phosphorylation at two sites, the activation loop (A-loop) and the hydrophobic motif (HM), for activity. Higher eukaryotes contain two NDR isoforms, NDR1 and NDR2. Both isoforms play a role in proper centrosome duplication. NDR1 is highly expressed in thymus, muscle, lung and spleen. It is not an essential protein because mice deficient of NDR1 remain viable and fertile. However, these mice develop T-cell lymphomas and appear to be hypersenstive to carcinogenic treatment. NDR1 appears to act as a tumor suppressor. The STK38/NDR1 gene is conserved in chimpanzee, dog, cow, mouse, rat, chicken, zebrafish, *Arabidopsis thaliana*, and rice.

Antibodies that are reactive against the human STK38 can be used to inhibit the enzyme activity and/or analyze the level of gene silencing by an RNAi agent directed to the STK38 gene. Such antibodies are commercially available, e.g. from INVITROGEN™, SIGMA-ALDRICH®, R&D SYSTEMS, and ABCAM®.

RNAi agents targeting the human STK38 are also commercially available, e.g. siRNAs from AMBION®.

Exostoses 1 (EXT1), GeneID: 2131, GENBANK™ Accession No.: NM_000127 (mRNA) and NP_000118 (protein) is an endoplasmic reticulum-resident type II transmembrane glycosyltransferase involved in the chain elongation step of heparan sulfate biosynthesis. Mutations in this gene cause the type I form of multiple exostoses. Biochemical assays for the enzyme activity and testing of inhibitors are known in the art, e.g. as disclosed by Sasaki N et al., J. Biol. Chem. 2008, 283(6):3594-606; and Kraushaar D C et al., J. Biol. Chem. 2009.

Antibodies that are reactive against the human EXT1 can be used to inhibit the enzyme activity and/or analyze the level of gene silencing by an RNAi agent directed to the EXT1 gene. Such antibodies are commercially available, e.g. anti-EXT1 catalog Nos.: #276-290, #626-640, #ab1 from SIGMA-ALDRICH®; catalog Nos.:# N-16 and #V-15 from SANTA CRUZ BIOTECHNOLOGY.

RNAi agents targeting the human EXT1 are also commercially available, e.g., shRNA exostoses (multiple) 1 from SIGMA-ALDRICH®; HuSH 29mer shRNA Constructs against EXT1 from ORIGENE®; and EXT1 shRNA constructs in the form of lentiviral particles and as shRNA plasmids and EXT1 siRNA from SANTA CRUZ BIOTECHNOLOGY.

Phospholipase C zeta 1 (PLCZ1, PLCξ), GeneID: 89869; GENBANK™ Accession No.: NM_033123.2 (mRNA) and NP_149114.2 (protein) is a protein of about 70 kDa, which makes it smaller in size than any of the other known vertebrate isoforms of phosphoinositide-specific PLC. Biochemical assays for the PLCξ enzyme activity and testing of inhibitors are known in the art, e.g. as disclosed by Swann K et al., Seminar Cell Dev. Biol. 2006 17:264-73.

RNAi agents targeting the human PLCZ1 are commercially available, e.g. HuSH 29mer shRNA constructs against PLCZ1 from ORIGENE®; shRNA phospholipase C: zeta 1 from SIGMA-ALDRICH®; and PLC zeta siRNA form SANTA CRUZ BIOTECHNOLOGY.

General small molecule inhibitors against PLCZ1 enzyme include: 1-[6-[[(17b)-3-Methoxyestra-1,3,5(10)-trien-17-yl]amino]hexyl]-1H-pyrrole-2,5-dione; O-(Octahydro-4,7-methano-1H-inden-5-yl)carbonopotassium dithioate; and 1,1,1-Trifluoro-6Z,9Z,12Z,15Z-heneicosateraen-2-one (Tocris Biosciences).

Protein tyrosine phosphatase, non-receptor type 9 (PTPN9), GeneID: 5780, GENBANK™ Accession No.: NM_002833 (mRNA) and NP_002824.1 (protein) is a member of the protein tyrosine phosphatase (PTP) family. PTPs are known to be signaling molecules that regulate a variety of cellular processes including cell growth, differentiation, mitotic cycle, and oncogenic transformation. This PTP contains an N-terminal domain that shares a significant similarity with yeast SEC14, which is a protein that has phosphatidylinositol transfer activity and is required for protein secretion through the Golgi complex in yeast. This PTP was found to be activated by polyphosphoinositide, and is thought to be involved in signaling events regulating phagocytosis. Biochemical assays for the enzyme activity and testing of inhibitors are known in the art, e.g. as disclosed by Qi Y et al., J. Cell Biochem. 2002, 86:79-89 and by Saito K et al., J. Biol. Chem. 2007, 1282:15170-8.

Antibodies that are reactive against PTPN9 can be used to inhibit the enzyme activity and/or analyze the level of gene silencing by an RNAi agent directed to the PTPN9 gene. Antibodies to human PTPN9 include: clone 291835 from R & D SYSTEMS; PTP-MEG2 (catalog #C-16, #G-18 and #H-300) from SANTA CRUZ BIOTECHNOLOGY.

RNAi agents targeting the human PTPN9 are also commercially available, e.g., siRNA and shRNAs. The available siRNA and shRNA to PTPN9 include: HuSH 29mer shRNA constructs against PTPN9 from ORIGENE®, and PTP-MEG2 shRNA against PTPN9 in the form of lentiviral particles and shRNA plasmid, and as siRNA from SANTA CRUZ BIOTECHNOLOGY.

Egl nine homolog 3 (EGLN3), GeneID: 112399, GENBANK™ Accession No.: NM_022073.3 (mRNA) and NP_071356.1 (protein) is an oxidoreducase that may be involved in certain cellular processes such as apoptosis, oxidation reduction, regulation of cell proliferation, and response to hypoxia. Biochemical assays for the EGLN3 enzyme activity and testing of inhibitors are known in the art, e.g. as disclosed by Lee S et al., Cancer Cell. 2005, 8:155-67.

Antibodies that are reactive against EGLN3 can be used to inhibit the enzyme activity and/or analyze the level of gene silencing by an RNAi agent directed to the EGLN3 gene. Antibodies to human EGLN3 include: polyclonal antibodies against EGLN3 from ORIGENE®, SIGMA-ALDRICH®, ABCAM® and PHD3 antibody from Bethyl.

RNAi agents targeting the human EGLN3 are also commercially available, e.g., siRNAs and shRNAs. SiRNA and shRNA to EGLN3 include: HuSH 29mer shRNA constructs against EGLN3 from ORIGENE®; HIF PHD3 shRNA (h) lentiviral particles, shRNA plasmid and HIF PHD3 siRNA from SANTA CRUZ BIOTECHNOLOGY.

MutL homolog 1 (MLH1), GeneID: 4292, GENBANK™ Accession No.: NM_000249.3 (mRNA for MutL protein homolog 1 isoform 1); NM_001167617.1 (mRNA for MutL protein homolog 1 isoform 2); NM_001167618.1 (mRNA for MutL protein homolog 1 isoform 3); NM_001167619.1 (mRNA for MutL protein homolog 1 isoform 4); NP_000240.1 (protein for MutL protein homolog 1 isoform 1); NP_001161089.1 (protein for MutL protein homolog 1 isoform 2); NP_001161090.1 (protein for MutL protein homolog 1 isoform 3); and NP_001161091.1 (protein for MutL protein homolog 1 isoform 4), is a human homolog of the *E. coli* DNA mismatch repair gene mutL. This gene was identified as a locus frequently mutated in hereditary nonpolyposis colon cancer (HNPCC) and is consistent with the characteristic alterations in microsatellite sequences found in HNPCC. Alternative splicing results in multiple transcript variants encoding distinct isoforms.

Biochemical assays for the activity of MLH1 and testing of inhibitors are known in the art, e.g. as disclosed by Datta J et al., Cancer Res. 2009, 69:4277-85; Drost M et al., Hum Mutat. 2009 Dec. 17.

Antibodies that are reactive against MLH1 can be used to inhibit the MLH1 activity and/or analyze the level of gene silencing by an RNAi agent directed to the MLH1 gene. Antibodies to human MLH1 include: anti-MLH1 (C-terminal) antibody and anti-MLH1 (N-terminal) antibody from SIGMA-ALDRICH®; anti-MLH1 (catalog #4C9C7) from Cell Signaling Technology; Mouse anti-human monoclonal (catalog #164C819 and clone 8L781) antibody from LIFESPAN Biosciences.

RNAi agents targeting the human MLH1 are also commercially available, e.g., siRNAs and shRNAs. The available siRNA and shRNA to MLH1 include: HuSH 29mer shRNA constructs against MLH1 ORIGENE®; MLH1 shRNA (h) lentiviral particles, shRNA Plasmid, and MLH1 siRNA from SANTA CRUZ BIOTECHNOLOGY.

ATP-binding cassette, sub-family C(CFTR/MRP), member 12 (ABCC12), GeneID: 94160, GENBANK™ Accession No.: NM_033226.2 (mRNA) and NP_150229 (protein) is a member of the superfamily of ATP-binding cassette (ABC) transporters and the encoded protein contains two ATP-binding domains and 12 transmembrane regions. ABC proteins transport various molecules across extra- and intracellular membranes. ABC genes are divided into seven distinct subfamilies: ABC1, MDR/TAP, MRP, ALD, OABP, GCN20, and White. This gene is a member of the MRP subfamily which is involved in multi-drug resistance. This gene and another subfamily member are arranged head-to-tail on chromosome 16q12.1. Increased expression of this gene is associated with breast cancer.

Biochemical assays for the enzyme activity of ABCC12 and testing of inhibitors are known in the art, e.g. as disclosed by Zhou S F et al., Curr. Med. Chem. 2008, 15:1981-2039; Toyoda Y et al., Xenobiotica. 2008, 38:833-62; and Haimeur A et al., Curr. Drug Metab. 2004, 5:21-53.

Antibodies that are reactive against ABCC12 can be used to inhibit the enzyme activity and/or analyze the level of gene silencing by an RNAi agent directed to the ABCC12 gene. Antibodies to human ABCC12 include: goat anti-MRP9/ABCC12 Antibody from Everest Biotech; ABCC12 Antibody from Novus Biologicals; goat anti-human polyclonal antibody against ABCC12 from LIFESPAN Biosciences; and ABCC12 (catalog #H-190) from SANTA CRUZ BIOTECHNOLOGY.

RNAi agents targeting the human ABCC12 are also commercially available, e.g., siRNAs and shRNAs. The available siRNA and shRNA to ABCC12 include: HuSH 29mer shRNA Constructs against ABCC12 from ORIGENE®; shRNA of ATP-binding cassette: sub-family C(CFTR/MRP): member 12 of ABCC12 from SIGMA-ALDRICH®; ABCC12 shRNA (h) lentiviral particles, ABCC12 shRNA Plasmid and ABCC12 siRNA from SANTA CRUZ BIOTECHNOLOGY.

DEFINITIONS

As used herein, the term "expanding" refers to increasing the number of like cells through cell division (mitosis). The terms "proliferating" and "expanding" are used interchangeably. The terms "proliferation" and "proliferative" have the same meaning as "expansion" and "expanded" respectively. In one aspect, the term "expanding" as applied to HSPCs is exclusive of cell division that results in daughter cells that have a more limited differentiation capacity than the starting cell. It is also possible that after cell division, the two daughter cells are different from each other in terms of cell differentiation state or potentials. For example, an HSPC described herein can undergo cell division and produce two daughter cells, one of which assumed a myeloid lineage differentiation pathway and will proceed to divide to give rise to more myeloid lineage cells. The second daughter cell assumes the role of the starting cell and can proceed to divide to give rise to more daughter cells that are different from each other in terms of cell differentiation state or potentials.

As used herein, the term "hematopoietic stem progenitor cell", "hematopoietic stem and progenitor cell" or "HSPC" refers to hematopoietic stem cells and/or hematopoietic progenitor cells that can differentiate into the hematopoietic lineage and give rise to all blood cell types such as white blood cells and red blood cells; all the blood cell types including myeloid (monocytes and macrophages, neutrophils, basophils, eosinophils, erythrocytes, megakaryocytes/platelets, dendritic cells), and lymphoid lineages (T-cells, B-cells, NK-cells). "Stem cells" are defined by their ability to form multiple cell types (multipotency) and their ability to self-renew. The definition of a hematopoietic stem cell as the term is used herein includes the ability to confer long-term repopulation of the myeloid and lymphoid lineages of an ablated subject. "Hematopoietic progenitor cells" are multipotent cells that are derived from hematopoietic stem cells but are more differentiated than the hematopoietic stem cell they came from and do not have the ability to self renew. "Hematopoietic progenitor cells" can be differentiated to the myeloid or the lymphoid lineage. A population of HSPCs can comprise the two types of cells: (1) hematopoietic stem cells and (2) hematopoietic progenitor cells.

The term "multipotency" refers to a cell's ability to differentiate into some but not all of the cells derived from all three germ layers. Thus, a multipotent cell is a partially differentiated cell. Multipotent cells are well known in the art, and examples of multipotent cells include adult somatic stem cells, such as for example, hematopoietic stem progenitor cells and neural stem cells, hair follicle stem cells, liver stem cells etc. Multipotent means a stem cell may form many types of cells in a given lineage, but not cells of other lineages. For example, a multipotent blood stem cell can form the many different types of blood cells (red, white, platelets, etc. . . . ), but it cannot form neurons; cardiovascular progenitor cell (MICP) differentiation into specific mature cardiac, pacemaker, smooth muscle, and endothelial cell types; pancreas-derived multipotent progenitor (PMP) colonies produce cell types of pancreatic lineage (cells that produces insulin, glucagon, amylase or somatostatin) and neural lineage (cells that are morphologically neuron-like, astrocytes-like or oligodendrocyte-like).

The term "multipotency" refers to a cell with the degree of developmental versatility that is less than totipotent and pluripotent.

The term "totipotency" refers to a cell with the degree of differentiation describing a capacity to make all of the cells in the adult body as well as the extra-embryonic tissues including the placenta. The fertilized egg (zygote) is totipotent as are the early cleaved cells (blastomeres)

The term "pluripotency" or a "pluripotent state" as used herein refers to a cell with the ability to differentiate into all three embryonic germ layers: endoderm (gut tissue), mesoderm (including blood, muscle, and vessels), and ectoderm (such as skin and nerve), and typically has the potential to divide in vitro for a long period of time, e.g., greater than one year or more than 30 passages.

The term "progenitor cell" is used herein to refer to cells that have a cellular phenotype that is more primitive (e.g., is at an earlier step along a developmental pathway or progression than is a fully differentiated cell) relative to a cell which it can give rise to by differentiation. Often, progenitor cells also have significant or very high proliferative potential but not self renewal capability. Progenitor cells can give rise to multiple distinct differentiated cell types or to a single differentiated cell type, depending on the developmental pathway and on the environment in which the cells develop and differentiate, e.g. myeloid lineage progenitor cells can give rise to monocytes, macrophages, neutrophils, basophils, eosinophils, erythrocytes, megakaryocytes/platelets and dendritic cells. Lymphoid lineage progenitor cells give rise to T-cells, B-cells, and NK-cells.

The term "stem cell" refers to a subset of progenitor cells that have the capacity or potential, under particular circumstances, to differentiate to a more specialized or differentiated phenotype, and which retains the capacity, under certain circumstances, to proliferate without substantially differentiating. The term "stem cell" as used herein, refers to an undifferentiated cell which is capable of proliferation and giving rise to more progenitor cells having the ability to generate a large number of mother cells that can in turn give rise to differentiated, or differentiable daughter cells. The daughter cells themselves can be induced to proliferate and produce progeny that subsequently differentiate into one or more mature cell types, while also retaining one or more cells with parental developmental potential. In one embodiment, the term stem cell refers generally to a naturally occurring mother cell whose descendants (progeny) specialize, often in different directions, by differentiation, e.g., by acquiring completely individual characters, as occurs in progressive diversification of embryonic cells and tissues. Cellular differentiation is a complex process typically occurring through many cell divisions. A differentiated cell may derive from a multipotent cell which itself is derived from a multipotent cell, and so on. While each of these multipotent cells may be considered stem cells, the range of cell types each can give rise to may vary considerably. Some differentiated cells also have the capacity to give rise to cells of greater developmental potential. Such capacity may be natural or may be induced artificially upon treatment with various factors. In many biological instances, stem cells are also "multipotent" because they can produce progeny of more than one distinct cell type, but this is not required for "stem-ness." Self-renewal is the other classical part of the stem cell definition, and it is essential as used in this document. An indication of self-renewal is asymmetric division, with one daughter retaining the stem state and the other daughter expressing some distinct other specific function and phenotype. The stem cells disclosed herein continue to undergo mitosis and proliferate after seven weeks in culture.

In the context of cell ontogeny, the term "differentiate", or "differentiating" is a relative term meaning a "differentiated cell" is a cell that has progressed further down the developmental pathway than its precursor cell. The term "differentiated cell" is meant any primary cell that is not, in its native form, pluripotent as that term is defined herein. The term a "differentiated cell" also encompasses cells that are partially differentiated, such as multipotent cells (e.g. hematopoietic stem progenitor cells).

In some embodiments, the term "differentiated cell" also refers to a cell of a more specialized cell type derived from a cell of a less specialized cell type (e.g., from an undifferentiated cell or a stem progenitor cell) where the cell has undergone a cellular differentiation process.

The term "contacting" or "contact" as used herein in connection with contacting an isolated cell population comprising of hematopoietic stem progenitor cells with an agent and/or RNAi agent as disclosed herein, includes subjecting the cell to a culture medium which comprises the agent. Where the hematopoietic stem progenitor cell is in vivo, contacting the HSPC with an agent and/or RNAi agent includes administering the agent and/or RNAi agent in a composition to a subject via an appropriate administration route such that the agent and/or RNAi agent contacts the HSPC in vivo.

As used herein "self renew" in reference to a cell refers to the cell's ability to maintain its own population at an approximately constant level. The cell makes a duplicate copy of one self while also making a progenitor cell that will go on to produce other type of cells. Normally when a single hematopoietic stem progenitor cell undergoes one cell division, two daughter cells are produced. One daughter becomes a progenitor cell that give rise to all the blood cell types while the other daughter cell becomes the hematopoietic stem progenitor cell.

The term "isolated" as used herein signifies that the cells are placed into conditions other than their natural environment. The term "isolated" does not preclude the later use of these cells thereafter in combinations or mixtures with other cells.

As used herein, "an isolated cell population comprising a hematopoietic stem progenitor cell" or "an isolated cell population comprising an HSPC" as used herein refers to a population of HSPCs that is removed from their natural environment, e.g. isolated by the methods disclosed herein. The population of HSPCs can be primary cells that have been removed from their original source, e.g. a tissue such as the bone marrow in an animal, and have not been cultured. The population of HSPCs can be homogenous, i.e. having cells of the same type, e.g. only hematopoietic stem cells or only hematopoietic progenitor cells; or can be heterogeneous, i.e. a mixed population of cells, cells of several types, e.g. hematopoeitic stem cells with myeloid lineage progenitor cells and lymphoid progenitor cells. Both myeloid lineage progenitor and lymphoid progenitor cells develop and produce cells with different roles in the hematopoeitic system. "An isolated cell population comprising an HSPC" is not necessary pure, but rather is enriched for HSPCs, e.g. relative to their environment in whole blood or bone marrow. By "enriched" is meant at least 2 fold higher concentration that a native sample, i.e. whole blood sample or bone marrow sample.

While strictly speaking, a nucleic acid sequence refers to the sequence of the nucleotide bases on the nucleic acid molecule, the terms "nucleic acid sequence" or "nucleic acid molecule" are used interchangeably herein. Thus, unless directed otherwise by context, the term "nucleic acid sequence" or "nucleic acid molecule" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one strand nucleic acid of a denatured double-stranded DNA. Alternatively, it can be a single-stranded nucleic acid not derived from any double-stranded DNA. In one aspect, the nucleic acid sequence is a DNA. In another aspect, the nucleic acid sequence is RNA. Suitable nucleic acid molecules are DNA, including genomic DNA, ribosomal DNA and cDNA. Other suitable nucleic acid molecules are RNA, including mRNA, rRNA and tRNA. The nucleic acid molecule can be naturally occurring, as in genomic DNA, or it may be synthetic, i.e., prepared based upon human action, or may be a combination of the two. The nucleic acid molecule can also have certain modifications such as 2'-deoxy, 2'-deoxy-2'-fluoro, 2'-O-methyl, 2'-O-methoxyethyl (2'-O-MOE), 2'-O-aminopropyl(2'-O-AP), 2'-O-dimethylaminoethyl(2'-O-DMAOE), 2'-O-dimethylaminopropyl (2'-O-DMAP), 2'-O-dimethylaminoethyloxyethyl(2'-O-DMAEOE), or 2'-O—N-methylacetamido(2'-O-NMA), cholesterol addition, phosphorothioate backbone as described in US Patent Application 20070213292; certain ribonucleosides that are linked between the 2'-oxygen and the 4'-carbon atoms with a methylene unit as described in U.S. Pat. No. 6,268,490, wherein both the patent and patent application are incorporated herein by reference in their entirety.

The terms "identical" or percent "identity", in the context of two or more nucleic acids sequences, refers to two or more sequences or subsequences that are the same or have a specified percentage of nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region (e.g., nucleotide sequence comprising the SEQ ID NOS.: 2-18 described herein), when compared and aligned for maximum correspondence over a comparison window or designated region) as measured using a BLAST or BLAST 2.0 sequence comparison algorithms with default parameters described below, or by manual alignment and visual inspection. Such sequences are also said to be "substantially identical." This term also refers to, or can be applied to, the complement of a test sequence. The term also can be used for sequences that have deletions and/or additions, as well as those that have substitutions. The BLAST or BLAST 2.0 sequence comparison/alignment algorithms can account for gaps and the like. Preferably, identity exists over a region that is at least about 15 nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 5 to 600, usually about 50 to about 200, more usually about 100 to about 150 in which a sequence can be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2: 482, 1981, by the homology alignment algorithm of Needleman & Wunsch, J. Mol. Biol. 48: 443, 1970, by the search for similarity method of Pearson & Lipman, Proc. Nat'l. Acad. Sci. USA 85: 2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology, Ausubel et al., eds. 1995 supplement)).

The term "vector" used herein refers to a nucleic acid sequence containing an origin of replication and which is designed for delivery to a host cell or transfer between different host cells. As used herein, a vector can be viral or non-viral. A vector can be a plasmid, cosmid, phagmid, virus, bacteriophage, bacterial artificial chromosome or yeast artificial chromosome. A vector can be a DNA or RNA vector. A vector can be either a self replicating extrachromosomal vector or a vector which integrates into a host genome.

As used herein, the term "expression vector" refers to a vector that has the ability to express heterologous nucleic acid fragments in a cell. An expression vector can comprise additional elements, for example, the expression vector can have two replication systems, thus allowing it to be maintained in two organisms, for example in human cells for expression and in a prokaryotic host for cloning and amplification.

As used herein, the term "viral vector" refers to a nucleic acid vector construct that includes at least one element of viral origin and has the capacity to be packaged into a viral vector particle. The viral vector can contain the sequences disclosed herein or RNAi sequences in place of non-essential viral genes. The vector and/or particle can be utilized for the purpose of transferring nucleic acids into cells either in vitro or in vivo. Numerous forms of viral vectors are known in the art.

The term "replication incompetent" as used herein means the viral vector cannot further replicate and package its genomes. For example, when the cells of a subject are infected with replication incompetent recombinant adeno-associated virus (rAAV) virions, the heterologous (also known as transgene) gene is expressed in the patient's cells, but, the rAAV is replication defective (e.g., lacks accessory genes that encode proteins essential for packaging the virus) and viral particles cannot be formed in the patient's cells.

The term "gene" means the nucleic acid sequence (DNA) which is transcribed to RNA in vitro or in vivo when operably linked to appropriate regulatory sequences. The gene may or may not include regions preceding and following the coding region, e.g. 5' untranslated (5'UTR) or "leader" sequences and 3' UTR or "trailer" sequences, as well as intervening sequences (introns) between individual coding segments (exons). The coding region of a gene can be a nucleotide sequence coding for an amino acid sequence or a functional RNA, such as tRNA, rRNA, catalytic RNA, siRNA, miRNA and antisense RNA. A gene can also be an mRNA or cDNA corresponding to the coding regions (e.g. exons and miRNA) optionally comprising 5'- or 3' untranslated sequences linked thereto. A gene can also be an amplified nucleic acid molecule produced in vitro comprising all or a part of the coding region and/or 5'- or 3'-untranslated sequences linked thereto.

The term "nucleic acid" or "oligonucleotide" or "polynucleotide" used herein can mean at least two nucleotides covalently linked together. As will be appreciated by those in the art, the depiction of a single strand also defines the sequence of the complementary strand. Thus, a nucleic acid also encompasses the complementary strand of a depicted single strand. Of course where context or express language requires that a nucleic acid is single stranded, the nucleic acid does not encompass the complementary strand. As will also be appreciated by those in the art, many variants of a nucleic acid can be used for the same purpose as a given nucleic acid. Thus, a nucleic acid can also encompass substantially identical nucleic acids and complements thereof.

Nucleic acids can be single stranded or double stranded, or can contain portions of both double stranded and single stranded sequence. The nucleic acid can be DNA, both genomic and cDNA, RNA, or a hybrid, where the nucleic acid can contain combinations of deoxyribo- and ribo-nucleotides, and combinations of bases including uracil, adenine, thymine, cytosine, guanine, inosine, xanthine hypoxanthine, isocytosine and isoguanine. Nucleic acids can be obtained, for example, by chemical synthesis methods or by recombinant methods.

A nucleic acid will generally contain phosphodiester bonds; although nucleic acid analogs can be included that can have at least one different linkage, e.g., phosphoramidate, phosphorothioate, phosphorodithioate, or O-methylphosphoroamidite linkages and peptide nucleic acid backbones and linkages. Other analog nucleic acids include those with positive backbones; non-ionic backbones, and non-ribose backbones, including those described in U.S. Pat. Nos. 5,235,033 and 5,034,506, which are incorporated by reference. Nucleic acids containing one or more non-naturally occurring or modified nucleotides are also included within one definition of nucleic acids. The modified nucleotide analog can be located for example at the 5'-end and/or the 3'-end of the nucleic acid molecule. Representative examples of nucleotide analogs can be selected from sugar- or backbone-modified ribonucleotides. It should be noted, however, that also nucleobase-modified ribonucleotides, i.e. ribonucleotides, containing a non naturally occurring nucleobase instead of a naturally occurring nucleobase such as uridines or cytidines modified at the 5-position, e.g. 5-(2-amino)propyl uridine, 5-bromo uridine; adenosines and guanosines modified at the 8-position, e.g. 8-bromo guanosine; deaza nucleotides, e.g. 7 deaza-adenosine; O- and N-alkylated nucleotides, e.g. N6-methyl adenosine are suitable. The 2' OH— group can be replaced by a group selected from H. OR, R. halo, SH, SR, NH2, NHR, NR2 or CN, wherein R is C-C6 alkyl, alkenyl or alkynyl and halo is F, Cl, Br or I. Modifications of the ribose-phosphate backbone can be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs can be made.

The term "subject" as used herein includes, without limitation, a human, mouse, rat, guinea pig, dog, cat, horse, cow, pig, monkey, chimpanzee, baboon, or rhesus. In one embodiment, the subject is a mammal. In another embodiment, the subject is a human.

As used herein, the term "operably linked" indicates to that the regulatory elements in genomic genes or in the nucleic acid constructs are positioned with respect to the genomic gene or other nucleic acid such that the gene or nucleic acid is transcribed to a primary transcript. The regulatory elements include, e.g. promoters for the respective RNA polymerase docking and initiation of transcription.

The term "agent" refers to any entity which is normally not present or not present at the levels being contacted to a cell, tissue or subject. Agent can be selected from a group comprising: chemicals; small molecules; nucleic acid sequences; nucleic acid analogues; proteins; peptides; aptamers; antibodies; or functional fragments thereof. A nucleic acid sequence can be RNA or DNA, and can be single or double stranded, and can be selected from a group comprising: nucleic acid encoding a protein of interest; oligonucleotides; and nucleic acid analogues, for example peptide-nucleic acid (PNA), pseudo-complementary PNA (pc-PNA), locked nucleic acid (LNA), etc. Such nucleic acid sequences include, but are not limited to nucleic acid sequence encoding proteins, for example that act as transcriptional repressors, antisense molecules, ribozymes, small inhibitory nucleic acid sequences, for example but not limited to RNAi, shRNAi, siRNA, micro RNAi (mRNAi), antisense oligonucleotides etc. A protein and/or peptide or fragment thereof can be any protein of interest, for example, but not limited to: mutated proteins, therapeutic proteins, and truncated proteins, wherein the protein is normally absent or expressed at lower levels in the cell. Proteins can also be selected from a group comprising mutated proteins, genetically engineered proteins, peptides, synthetic peptides, recombinant proteins, chimeric proteins, antibodies, midibodies, tribodies, humanized proteins, humanized antibodies, chimeric antibodies, modified proteins and fragments thereof. An agent can be applied to the medium, where it contacts the cell and induces its effects. Alternatively, an agent can be intracellular as a result of introduction of a nucleic acid sequence encoding the agent into the cell and its transcription resulting in the production of the nucleic acid and/or protein environmental stimuli within the cell. In certain embodiments the agent is a small molecule having a chemical moiety. For example, chemical moieties included unsubstituted or substituted alkyl, aromatic, or heterocyclyl moieties including macrolides, leptomycins and related natural products or analogues thereof. Agents can be known to have a desired activity and/or property, or can be selected from a library of diverse compounds.

As used herein, the term "RNAi agent" means any agent capable of mediating RNA interference ("RNAi"). For example the agent may comprise a double-stranded polynucleotide molecule comprising sense and antisense regions, wherein the antisense region comprises complementarity to a target nucleic acid. Alternatively the molecule may also, for example, comprise a single-stranded hairpin polynucleotide having sense and antisense regions, wherein the antisense region comprises complementarity to such a target nucleic acid molecule. The molecule may also comprise a circular single-stranded polynucleotide having one or more loop structures and a stem comprising self-complementary sense and antisense regions, wherein the antisense region comprises complementarity to a target nucleic acid molecule, and wherein the circular polynucleotide can be processed either in vivo or in vitro to generate an active siRNA capable of mediating RNAi. An RNAi agent may also be a vector, e.g. nucleic acid vector such as a DNA vector, an expression vector such as a lentivirus, coding for a molecule capable of mediating sequence specific RNAi, for example coding for short interfering RNA (siRNA), double-stranded RNA (dsRNA), micro-RNA, short hairpin RNA (shRNA), short interfering oligonucleotide, short interfering nucleic acid, and precursors and derivatives thereof.

In molecular biology, complementarity is a property of double-stranded nucleic acids such as DNA and RNA as well as DNA:RNA duplexes. Each strand is complementary to the other in that the base pairs between them are non-covalently connected via two or three hydrogen bonds.

The term "inhibits" as used herein refers to a decrease in the expression, gene silencing or activity or function of a protein, variants or homologues thereof and does not necessarily mean complete inhibition of expression and/or activity. Rather, expression or activity of the protein is inhibited to an extent, and/or for a time, sufficient to produce the desired effect. Agents that inhibit a protein disclosed herein, i.e. STK38, EXT1, PTPN9, EGLN3, MLH1, and ABCC12, are agents that inhibit the protein and/or function by at least 10%. In some embodiments, an inhibitor of the protein is an agent that inhibits the protein or expression of the protein by at least 10%.

As used herein, "gene silencing" or "gene silenced" in reference to an activity of an RNAi molecule, for example a siRNA or shRNA, refers to a decrease in the mRNA level in a cell for a target gene, i.e. STK38, EXT1, PTPN9, EGLN3, MLH1, and ABCC12, by at least about 5%, about 10%, about 20%, about 30%, about 40%, about 50%, about 60%, about 70%, about 80%, about 90%, about 95%, about 99%, up to and including about 100% of the mRNA level found in the cell without the presence of the RNAi agents, e.g. shRNA or RNA interference molecules. In one preferred embodiment, the mRNA levels are decreased by at least about 70%, and preferably about 80%, about 90%, about 95%, about 99%, or even about 100%.

As used herein, the term "RNAi" refers to any type of interfering RNA, including but not limited to, siRNAi, shRNAi, endogenous microRNA and artificial microRNA. For instance, it includes sequences previously identified as siRNA, regardless of the mechanism of down-stream processing of the RNA (i.e. although siRNAs are believed to have a specific method of in vivo processing resulting in the cleavage of mRNA, such sequences can be incorporated into the vectors in the context of the flanking sequences described herein).

As used herein an "siRNA" refers to a nucleic acid that forms a double stranded RNA, which double stranded RNA has the ability to reduce or inhibit expression of a gene or target gene when the siRNA is present or expressed in the same cell as the target gene, for example STK38, EXT1, PTPN9, EGLN3, MLH1, and ABCC12. The double stranded RNA siRNA can be formed by the complementary strands. In one embodiment, a siRNA refers to a nucleic acid that can form a double stranded siRNA. The sequence of the siRNA can correspond to the full length target gene, or a subsequence thereof. Typically, the siRNA is at least about 15-50 nucleotides in length (e.g., each complementary sequence of the double stranded siRNA is about 15-50 nucleotides in length, and the double stranded siRNA is about 15-50 base pairs in length, preferably about 19-30 base pairs, preferably about 20-25 base pairs in length, e.g., 20, 21, 22, 23, 24, 25, 26, 27, 28, 29, or 30 nucleotides in length). It is preferred that an siRNA be less than 30 nucleotide, as longer dsRNA tend to induce an apoptotic stress response in higher eukaryotic cells.

As used herein "shRNA" or "small hairpin RNA" (also called stem loop) is a type of siRNA. In one embodiment, these shRNAs are composed of a short, e.g. about 15 to about 25 nucleotide, antisense strand, followed by a nucleotide loop of about 5 to about 9 nucleotides, and the analogous and complementary sense strand. Alternatively, the sense strand can precede the nucleotide loop structure and the antisense strand can follow.

The terms "microRNA" or "miRNA" are used interchangeably herein refer to endogenous ds RNAs, some of which are known to regulate the expression of protein-coding genes at the posttranscriptional level. Endogenous microRNAs are small RNAs naturally present in the genome which are capable of modulating the productive utilization of mRNA. The term artificial microRNA includes any type of RNA sequence, other than endogenous microRNA, which is capable of modulating the productive utilization of mRNA. MicroRNA sequences have been described in publications such as Lim, et al., Genes & Development, 17, p. 991-1008 (2003), Lim et al Science 299, 1540 (2003), Lee and Ambros Science, 294, 862 (2001), Lau et al., Science 294, 858-861 (2001), Lagos-Quintana et al, Current Biology, 12, 735-739 (2002), Lagos Quintana et al, Science 294, 853-857 (2001), and Lagos-Quintana et al, RNA, 9, 175-179 (2003), which are incorporated by reference. Multiple microRNAs can also be incorporated into a precursor molecule. Furthermore, miRNA-like stem-loops can be expressed in cells as a vehicle to deliver artificial miRNAs and short interfering RNAs (siRNAs) for the purpose of modulating the expression of endogenous genes through the miRNA and or RNAi pathways.

As used herein, "double stranded RNA" or "dsRNA" refers to RNA molecules that are comprised of two strands. Double-stranded molecules include those comprised of a single RNA molecule that doubles back on itself to form a two-stranded structure. For example, the stem loop structure of the progenitor molecules from which the single-stranded miRNA is derived, called the pre-miRNA (Bartel et al. 2004. Cell 116: 281-297), comprises a dsRNA molecule.

The term "effective amount" as used herein refers to the amount of therapeutic agent of pharmaceutical composition sufficient to increase the number of HSPCs and/or blood cells in the bone marrow and/or in circulation by at least about 10% compared to before administration the composition.

As used herein, the term "administering" refers to the placement of the agents that inhibit STK38, EXT1, PTPN9, EGLN3, MLH1, and ABCC12 as disclosed herein into a subject by a method or route which results in at least partial localization of the agents at a desired site. The agent can be administered by any appropriate route which results in an desired effect in the subject, e.g. increase the number of circulating red blood cells.

As used herein, the term "pharmaceutical composition" refers to an active agent in combination with a pharmaceutically acceptable carrier of chemicals and compounds commonly used in the pharmaceutical industry. The term "pharmaceutically acceptable carrier" excludes tissue culture medium.

In one embodiment, the term "pharmaceutically acceptable" means approved by a regulatory agency of the Federal or a state government or listed in the U.S. Pharmacopeia or other generally recognized pharmacopeia for use in animals, and more particularly in humans. Specifically, it refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations, and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in Remington's Pharmaceutical Sciences, 18th Ed., Gennaro, ed. (Mack Publishing Co., 1990). The formulation should suit the mode of administration.

As used herein, the term "comprising" or "comprises" is used in reference to methods, and respective component(s) thereof, that are essential to the subject matter or composition, yet open to the inclusion of unspecified elements, whether essential or not. The use of "comprising" indicates inclusion rather than limitation.

As used herein the term "consisting essentially of" or "consists essentially of" refers to those elements required for a given embodiment. The term permits the presence of elements that do not materially affect the basic and novel or functional characteristic(s) of that embodiment.

The term "consisting of" refers to methods, and respective components thereof as described herein, which are exclusive of any element not recited in that description of the embodiment.

RNAi Agents

Protein expression from the genes for STK38, EXT1, PTPN9, EGLN3, MLH1, and ABCC12 can be reduced by inhibition of the expression of polypeptide (e.g., transcription, translation, post-translational processing) or by "gene silencing" methods commonly known by persons of ordinary skill in the art. Exemplary gene silencing methods include RNA interference and inhibition with antisense oligonucleotides (antisense mechanism).

RNA interference (RNAi) is an evolutionarily conserved process whereby the expression or introduction of a nucleotide sequence that is identical or highly similar to a target gene or mRNA results in the sequence specific degradation or specific post-transcriptional gene silencing (PTGS) of messenger RNA (mRNA) transcribed from that targeted gene (see for example Coburn, G. and Cullen, B. (2002) J. Virology 76:9225). In nature, RNAi is initiated by the dsRNA-specific endonuclease Dicer, which promotes processive cleavage of long dsRNA into double-stranded fragments termed siRNAs. siRNAs are incorporated into a protein complex (termed "RNA induced silencing complex," or "RISC") that recognizes and cleaves target mRNAs. RNAi can also be initiated by introducing nucleic acid molecules, e.g., synthetic siRNAs or RNA interfering agents, to inhibit or silence the expression of target genes. As used herein, "inhibition of target gene expression" includes any decrease in expression or protein activity or level of the mRNA or protein encoded by the target gene as compared to a situation wherein no RNA interference has been induced. The decrease will be of at least and preferably at least 10%, 20%, 30%, 40%, 50%, 60%, 70%, 80%, 90%, 95% or 99% or more as compared to the expression of a target gene or the activity or level of the protein encoded by a target gene which has not been targeted by an RNA interfering agent.

As used herein, the term "RNAi agent" refers to any agent capable of mediating RNA interference ("RNAi"). In some embodiments, RNAi agent is a single-stranded or double-stranded oligonucleotide. RNAi-mediating molecules, include but are not limited to, siRNA, dsRNA, stRNA, shRNA, microRNA and modified versions thereof, where the RNAi agent silences the gene expression of STK38, EXT1, PTPN9, EGLN3, MLH1 and ABCC12 gene. An oligonucleotide based RNAi agent can be chemically synthesized, can be produced by in vitro transcription, or can be produced within a host cell.

In some embodiments, the RNAi agent is an anti-sense oligonucleic acid, or a nucleic acid analogue, for example, DNA, RNA, peptide-nucleic acid (PNA), pseudo-complementary PNA (pc-PNA), aptamers or locked nucleic acid (LNA) and the like.

In some embodiments, single-stranded RNA (ssRNA), a form of RNA endogenously found in eukaryotic cells can be used to form an RNAi molecule. Cellular ssRNA molecules include messenger RNAs (and the progenitor pre-messenger RNAs), small nuclear RNAs, small nucleolar RNAs, transfer RNAs and ribosomal RNAs.

In some embodiments, the double-stranded RNAi agent comprises a sense strand and an antisense strand, wherein the antisense strand has a region of complementarity which is complementary to at least a part of a target sequence, and the duplex region is 14-30 nucleotides in length. Similarly, the region of complementarity to the target sequence is between 14 and 30, more generally between 18 and 25, yet more generally between 19 and 24, and most generally between 19 and 21 nucleotides in length. The phrase "antisense strand" as used herein, refers to an oligonucleotide that is substantially or 100% complementary to a target sequence of interest. The phrase "antisense strand" includes the antisense region of both oligonucleotides that are formed from two separate strands, as well as unimolecular oligonucleotides that are capable of forming hairpin or dumbbell type structures. The phrase "sense strand" refers to an oligonucleotide that has the same nucleotide sequence, in whole or in part, as a target sequence such as a messenger RNA or a sequence of DNA.

"Substantial complementarity" refers to polynucleotide strands exhibiting 85% or greater complementarity, excluding regions of the polynucleotide strands, such as overhangs, that are selected so as to be noncomplementary. Specific binding requires a sufficient degree of complementarity to avoid non-specific binding of the oligomeric compound to non-target sequences under conditions in which specific binding is desired, i.e., under physiological conditions in the case of in vivo assays or therapeutic treatment, or in the case of in vitro assays, under conditions in which the assays are performed. A percent complementarity indicates the percentage of contiguous residues in a nucleic acid molecule that can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary).

In some embodiments, the double-stranded region of a double-stranded oligonucleotide is equal to or at least, 10, 11, 12, 13, 14, 15, 16, 17, 18, 19, 20, 21, 22, 23, 23, 24, 25, 26, 27, 28, 29, or 30 nucleotide pairs in length. In some embodiments, the antisense strand of a double-stranded RNAi agent is equal to or at least 14, 15, 16, 17, 18, 19, 20, 21, 22, 23, 23, 24, 25, 26, 27, 28, 29, or 30 nucleotides in length. In some embodiments, the sense strand of a double-stranded RNAi is equal to or at least 10, 11, 12, 13, 14, 15, 16, 17, 18, 19, 20, 21, 22, 23, 23, 24, 25, 26, 27, 28, 29, or 30 nucleotides in length.

The double-stranded RNAi agent can comprise a single-stranded 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand.

Double-stranded RNAi agents also include small hairpin (also called stem loop) RNAs (shRNAs). In one embodiment, these shRNAs are composed of a short (e.g., about 19 to about 25 nucleotide) antisense strand, followed by a nucleotide loop of about 5 to about 9 nucleotides, and the analogous sense strand. Alternatively, the sense strand can precede the nucleotide loop structure and the antisense strand can follow. These shRNAs can be contained in plasmids, retroviruses, and lentiviruses and expressed from, for example, the pol III U6 promoter, or another promoter (see, e.g., Stewart, et al. (2003) RNA April; 9(4):493-501, incorporated by reference herein in its entirety).

By "target sequence" is meant any nucleic acid sequence whose expression or activity is to be modulated. The target nucleic acid can be DNA or RNA, such as endogenous DNA or RNA, viral DNA or viral RNA, or other RNA encoded by a gene, virus, bacteria, fungus, mammal, or plant. In some embodiments, the target sequence is a cellular gene or genomic sequence, e.g. that of STK38, EXT1, PTPN9, EGLN3, MLH1, and ABCC12 mRNA sequence found at GENBANK™ Accession Nos.: NM_007271.2, NM_000127, NM_033123.2, NM_002833, NM_022073.3, NM_000249.3, NM_001167617.1, NM_001167618.1, NM_001167619.1, and NM_033226.2.

The RNAi agent preferably targets only one sequence. Each of the RNA interfering agents, such as siRNAs, can be screened for potential off-target effects by, for example, expression profiling. Such methods are known to one skilled in the art and are described, for example, in Jackson et al, Nature Biotechnology 2003, 6:635-637. In addition to expression profiling, one can also screen the potential target sequences for similar sequences in the sequence databases to identify potential sequences which can have off-target effects. For example, as few as 11 contiguous nucleotides of sequence identity are sufficient to direct silencing of non-targeted transcripts. Therefore, one can initially screen the proposed siRNAs to avoid potential off-target silencing using the sequence identity analysis by any known sequence comparison methods, such as BLAST.

The RNAi agents need not be limited to those molecules containing only unmodified nucleotides, but, for example, further encompass chemically modified nucleotides and/or non-nucleotides, and also include molecules wherein a ribose sugar molecule is substituted for another sugar molecule or a molecule which performs a similar function. Moreover, a non-natural linkage between nucleotide residues can be used, such as a phosphorothioate linkage. For example, siRNA containing D-arabinofuranosyl structures in place of the naturally-occurring D-ribonucleosides found in RNA can be used in RNAi agents useful for the methods described herein (U.S. Pat. No. 5,177,196). Other examples include RNA molecules containing o-linkage between the sugar and the heterocyclic base of the nucleoside, which confers nuclease resistance and tight complementary strand binding to the oligonucleotides. Other modifications to the polynucleotide include the incorporation or substitution of molecules similar to the oligonucleotides containing 2'-O-methyl ribose, arabinose and particularly D-arabinose (U.S. Pat. No. 5,177,196). These references are incorporated herein by reference in their entirety.

Oligonucleotides can be derivatized with a reactive functional group of a reporter group, such as a fluorophore. Particularly useful derivatives are modified at a terminus or termini of an oligonucleotide strand, typically the 3' terminus of the sense strand of double-stranded RNAi agents. For example, the 2'-hydroxyl at the 3' terminus can be readily and selectively derivatized with a variety of groups.

Other useful oligonucleotide modifications include incorporation of nucleotides having modified carbohydrate moieties, such as 2'O-alkylated residues or 2'-O-methyl ribosyl derivatives and 2'-O-fluoro ribosyl derivatives. The bases (nucleobases) can also be modified. Any modified base useful for inhibiting or interfering with the expression of a target sequence or that continues to permit RNA interference can be used. For example, halogenated bases, such as 5-bromouracil and 5-iodouracil can be incorporated. The bases can also be alkylated, for example, 7-methylguanosine can be incorporated in place of a guanosine residue. Non-natural bases that yield successful inhibition can also be incorporated.

The more preferred oligonucleotide modifications include 2'-deoxy-2'-fluorouridine or locked nucleic acid (LNA) nucleotides and RNA duplexes containing either phosphodiester or varying numbers of phosphorothioate linkages. Such modifications are known to one skilled in the art and are described, for example, in Braasch et al., Biochemistry, 42: 7967-7975, 2003. Most of the useful modifications to the siRNA molecules can be introduced using chemistries established for antisense oligonucleotide technology. Preferably, the modifications involve minimal 2'-O-methyl modification, preferably excluding such modification. Modifications also preferably exclude modifications of the free 5'-hydroxyl groups of the siRNA.

Locked nucleic acids (LNAs), also known as bridged nucleic acids (BNAs), were developed by Wengel and co-workers (Koshkin A. A., 1998, Tetrahedron, 54:3607-3630) and Imanishi and co-workers (Obika S., 1998, Tetrahedron Lett., 39:5401-5404). LNA bases are ribonucleotide analogs containing a methylene linkage between the 2' oxygen and the 4' carbon of the ribose ring. The constraint on the sugar moiety results in a locked 3'-endo conformation that preorganizes the base for hybridization and increases melting temperature (Tm) values as much as 10° C. per base (Wengel J., 1999, Acc. Chem. Res., 32:301-310; Braasch D. A. and Corey, D. R., 2001, Chem. Biol., 8:1-7). LNA bases can be incorporated into oligonucleotides using standard protocols for DNA synthesis. This commonality facilitates the rapid synthesis of chimeric oligonucleotides that contain both DNA and LNA bases and allows chimeric oligomers to be tailored for their binding affinity and ability to activate RNase H. Because oligomers that contain LNA bases have a native phosphate backbone they are readily soluble in water. Introduction of LNA bases also confers resistance to nucleases when incorporated at the 5' and 3' ends of oligomers (Crinelli R., et. al., 2002, Nucleic Acids Res., 30:2435-2443). The ability to use LNAs for in vivo applications is also favored by the finding that LNAs have demonstrated low toxicity when delivered intravenously to animals (Wahlestedt C., et. al., 2000, Proc. Natl. Acad. Sci. USA, 97: 5633-5638).

LNAs and LNA-DNA chimeras have been shown to be potent inhibitors of human telomerase, and a relatively short eight base LNA has been shown to be a 1000-fold more potent agent than an analogous peptide nucleic acid (PNA) oligomer (Elayadi A. N., et. al., 2002, Biochemistry, 41: 9973-9981). LNAs and LNA-DNA chimeras have also been shown to be useful agents for antisense gene inhibition. Wengel and co-workers have used LNAs to inhibit gene expression in mice (Wahlestedt C., et. al., 2000, Proc. Natl. Acad. Sci. USA, 97:5633-5638), while Erdmann and colleagues have described the design of LNA-containing oligomers that recruit RNase H and have described the rules governing RNase H activation by LNA-DNA chimeras in cell-free systems (Kurreck J., et. al., 2002, Nucleic Acids Res., 30:1911-1918).

The syntheses of LNA-containing oligomers are known in the art, for examples, as described in U.S. Pat. Nos. 6,316,198, 6,670,461, 6,794,499, 6,977,295, 6,998,484, 7,053,195, and U.S Patent Publication No. US 2004/0014959, and all of which are hereby incorporated by reference in their entirety.

Another nucleic acid derivative envisioned in the methods described herein is phosphorodiamidate morpholino oligomer (PMO). PMOs are DNA mimics that inhibit expression of specific mRNAs in eukaryotic cells (Arora, V., et. al., 2000, J. Pharmacol. Exp. Ther. 292:921-928; Qin, G., et al., 2000, Antisense Nucleic Acid Drug Dev. 10:11-16; Summerton, J., et. al., 1997, Antisense Nucleic Acid Drug Dev. 7:63-70). They are synthesized by using the four natural bases, with a base sequence that is complementary (antisense) to a region of a specific mRNA. They are different than DNA in the chemical structure that links the bases together. Ribose has been replaced with a morpholine group, and the phosphodiester is replaced with a phosphorodiamidate. These alterations make the antisense molecule resistant to nucleases (Hudziak, R., et. al., 1996 Antisense Nucleic Acid Drug Dev. 6:267-272) and free of charges at physiological pH, yet it retains the molecular architecture required for binding specifically to a complementary strand of nucleic acid (Stein, D., et. al, 1997, Antisense Nucleic Acid Drug Dev. 7:151-157; Summerton, J., et. al., 1997, Antisense Nucleic Acid Drug Dev. 7:63-70; Summerton, J., and D. Weller., 1997, Antisense Nucleic Acid Drug Dev. 7:187-195).

The synthesis, structures, and binding characteristics of morpholine oligomers are detailed in U.S. Pat. Nos. 5,698,685, 5,127,866, 5,142,047, 5,166,315, 5,521,063, and 5,506,337, and all of which are incorporated herein by reference in their entirety. PMOs can be synthesized at AVI BioPharma (Corvallis, Oreg.) in accordance with known methods, as described, for example, in Summerton, J., and D. Weller U.S. Pat. No. 5,185,444; and Summerton, J., and D. Weller. 1997, Antisense Nucleic Acid Drug Dev. 7:187-195. For example, PMO against STK38 or EXT1 transcripts containing between 12-40 nucleotide bases and having a targeting sequence of at least 12 subunits complementary to the respective transcript can be prepared. Methods of making and using PMO for the inhibition of gene expression in vivo are described in U.S. Patent Publication No. US 2003/0171335; US 2003/0224055; US 2005/0261249; US 2006/0148747; S 2007/0274957; US 2007/003776; and US 2007/0129323; and these are hereby incorporated by reference in their entirety.

"Short interfering RNA" (siRNA), also referred to herein as "small interfering RNA" is defined as an agent which functions to inhibit expression of a target gene, e.g., by RNAi. An siRNA can be chemically synthesized, can be produced by in vitro transcription, or can be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, 22, or 23 nucleotides in length, and can contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. Preferably the siRNA is capable of promoting RNA interference through degradation or specific post-transcriptional gene silencing (PTGS) of the target messenger RNA (mRNA).

siRNAs also include small hairpin (also called stem loop) RNAs (shRNAs). In one embodiment, these shRNAs are composed of a short (e.g., about 19 to about 25 nucleotide) antisense strand, followed by a nucleotide loop of about 5 to about 9 nucleotides, and the analogous sense strand. Alternatively, the sense strand can precede the nucleotide loop structure and the antisense strand can follow. These shRNAs can be contained in plasmids, retroviruses, and lentiviruses and expressed from, for example, the pol III U6 promoter, or another promoter (see, e.g., Stewart, et al. (2003) RNA April; 9(4):493-501, incorporated by reference herein in its entirety).

siRNA molecules need not be limited to those molecules containing only RNA, but, for example, further encompasses chemically modified nucleotides and non-nucleotides, and also include molecules wherein a ribose sugar molecule is substituted for another sugar molecule or a molecule which performs a similar function. Moreover, a non-natural linkage between nucleotide residues can be used, such as a phosphorothioate linkage. For example, siRNA containing D-arabinofuranosyl structures in place of the naturally-occurring D-ribonucleosides found in RNA can be used in RNAi agents according to the present invention (U.S. Pat. No. 5,177,196). Other examples include RNA molecules containing the o-linkage between the sugar and the heterocyclic base of the nucleoside, which confers nuclease resistance and tight complementary strand binding to the oligonucleotidesmolecules similar to the oligonucleotides containing 2'-O-methyl ribose, arabinose and particularly D-arabinose (U.S. Pat. No. 5,177,196). These references are incorporated herein by reference in their entirety.

siRNA and miRNA molecules having various "tails" covalently attached to either their 3'- or to their 5'-ends, or to both, are also known in the art and can be used to stabilize the siRNA and miRNA molecules delivered using the methods of the present invention. Generally speaking, intercalating groups, various kinds of reporter groups and lipophilic groups attached to the 3' or 5' ends of the RNA molecules are well known to one skilled in the art and are useful according to the methods of the present invention. Descriptions of syntheses of 3'-cholesterol or 3'-acridine modified oligonucleotides applicable to preparation of modified RNA molecules useful according to the present invention can be found, for example, in the articles: Gamper, H. B., Reed, M. W., Cox, T., Virosco, J. S., Adams, A. D., Gall, A., Scholler, J. K., and Meyer, R. B. (1993) Facile Preparation and Exonuclease Stability of 3'-Modified Oligodeoxynucleotides. Nucleic Acids Res. 21 145-150; and Reed, M. W., Adams, A. D., Nelson, J. S., and Meyer, R. B., Jr. (1991) Acridine and Cholesterol-Derivatized Solid Supports for Improved Synthesis of 3'-Modified Oligonucleotides. Bioconjugate Chem. 2 217-225 (1993).

Other siRNAs useful for targeting the genes of STK38, EXT1, PTPN9, EGLN3, MLH1, and ABCC12 can be readily designed and tested. Accordingly, siRNAs useful for the methods described herein include siRNA molecules of about 15 to about 40 or about 15 to about 28 nucleotides in length, which are homologous to a gene sequence for STK38, EXT1, PTPN9, EGLN3, MLH1, and ABCC12. Preferably, the siRNA molecules targeting the gene of STK38, EXT1, PTPN9, EGLN3, MLH1, and ABCC12 gene sequence have a length of about 15 to about 25 nucleotides. More preferably, the siRNA molecules have a length of about 19, 20, 21, or 22 nucleotides. The siRNA molecules can also comprise a 3' hydroxyl group. The siRNA molecules can be blunt ended or comprise overhanging ends (e.g., 5', 3'). In specific embodiments, the RNA molecule is double stranded and either blunt ended or comprises overhanging ends.

In one embodiment, at least one strand of the RNA molecule has a 3' overhang from about 0 to about 6 nucleotides (e.g., pyrimidine nucleotides, purine nucleotides) in length. In other embodiments, the 3' overhang is from about 1 to about 5 nucleotides, from about 1 to about 3 nucleotides and from about 2 to about 4 nucleotides in length. In one embodiment, the RNA molecule that targets the gene of STK38, EXT1, PTPN9, EGLN3, MLH1, and ABCC12 is double stranded wherein one strand has a 3' overhang and the other strand can be blunt-ended or have an overhang. In the embodiment in which the gene targeting RNA molecule is double stranded and both strands comprise an overhang, the length of the overhangs can be the same or different for each strand. In one embodiment, the RNA comprises at least 6, 7, 8, 9, 10, 11, 12, 13, 14, 15, 16, 17, 18, 19, 20, 21, or 22 nucleotides which are paired and which have overhangs of from about 1 to about 3, particularly about 2, nucleotides on both 3' ends of the RNA. In one embodiment, the 3' overhangs can be stabilized against degradation. In a preferred embodiment, the RNA is stabilized by including purine nucleotides, such as adenosine or guanosine nucleotides. Alternatively, substitution of pyrimidine nucleotides by modified analogues, e.g., substitution of uridine 2 nucleotide 3' overhangs by 2'-deoxythymidine is tolerated and does not affect the efficiency of RNAi. The absence of a 2' hydroxyl significantly enhances the nuclease resistance of the overhang in tissue culture medium.

In some embodiments, assessment of the expression and/or knock down of gene of STK38, EXT1, PTPN9, EGLN3, MLH1, and ABCC12 using gene specific siRNAs can be determined by methods that are well known in the art, such as western blot analysis or enzyme activity assays. Other methods can be readily performed by those of skill in the art based on the known sequence of the target mRNA.

siRNA sequences are chosen to maximize the uptake of the antisense (guide) strand of the siRNA into RISC and thereby maximize the ability of RISC to target the mRNA of the gene of interest. This can be accomplished by scanning for sequences that have the lowest free energy of binding at the 5'-terminus of the antisense strand. The lower free energy leads to an enhancement of the unwinding of the 5'-end of the antisense strand of the siRNA duplex, thereby ensuring that the antisense strand will be taken up by RISC and direct the sequence-specific cleavage of the mRNA of the human genes of STK38, EXT1, PTPN9, EGLN3, MLH1, and ABCC12. The free energy can be determined by any method known in the art, e.g. as disclosed in Hong Zhou and Xiao Zeng, 2008, "Energy Profile and Secondary Structure Impact shRNA Efficacy" IEEE International Conference on Bioinformatics and Biomedicine, pages 31-36; and J. M Silva, et al., 2003, Nature Genetics 35:303.

RNAi agents useful in the methods as disclosed herein can be produced using any known techniques such as direct chemical synthesis, through processing of longer double stranded RNAs by exposure to recombinant Dicer protein or *Drosophila* embryo lysates, or through an in vitro system derived from S2 cells, using phage RNA polymerase, RNA-dependant RNA polymerase, and DNA based vectors. Use of cell lysates or in vitro processing can further involve the subsequent isolation of the short, for example, about 21-23 nucleotide, siRNAs from the lysate, etc. Chemical synthesis usually proceeds by making two single stranded RNA-oligomers followed by the annealing of the two single stranded oligomers into a double stranded RNA. Other examples include methods disclosed in WO 99/32619 and WO 01/68836 that teach chemical and enzymatic synthesis of siRNA. Moreover, numerous commercial services are available for designing and manufacturing specific siRNAs (see, e.g., QIAGEN Inc., Valencia, Calif. and AMBION Inc., Austin, Tex.)

In one embodiment, RNAi agents of the genes of STK38, EXT1, PTPN9, EGLN3, MLH1, and ABCC12 can be obtained synthetically, for example, by chemically synthesizing a nucleic acid by any method of synthesis known to the skilled artisan. The synthesized RNAi agents can then be purified by any method known in the art. Methods for chemical synthesis of nucleic acids include, but are not limited to, in vitro chemical synthesis using phosphotriester, phosphate or phosphoramidite chemistry and solid phase techniques, or via deoxynucleoside H-phosphonate intermediates (see U.S. Pat. No. 5,705,629 to Bhongle).

The siRNA molecules described herein can be generated by annealing two complementary single-stranded RNA molecules together (one of which matches a portion of the target mRNA) (Fire et al., U.S. Pat. No. 6,506,559) or through the use of a single hairpin RNA molecule that folds back on itself to produce the requisite double-stranded portion (Yu et al. (2002) Proc. Natl. Acad. Sci. USA 99:6047-52). The siRNA molecules can also be chemically synthesized (Elbashir et al. (2001) Nature 411:494-98).

Synthetic siRNA molecules, including shRNA molecules, can be obtained using a number of techniques known to those of skill in the art. For example, the siRNA molecule can be chemically synthesized or recombinantly produced using methods known in the art, such as using appropriately protected ribonucleoside phosphoramidites and a conventional DNA/RNA synthesizer (see, e.g., Elbashir, S. M. et al. (2001) Nature 411:494-498; Elbashir, S. M., W. Lendeckel and T. Tuschl (2001) Genes & Development 15:188-200; Harborth, J. et al. (2001) J. Cell Science 114:4557-4565; Masters, J. R. et al. (2001) Proc. Natl. Acad. Sci., USA 98:8012-8017; and Tuschl, T. et al. (1999) Genes & Development 13:3191-3197). Alternatively, several commercial RNA synthesis suppliers are available including, but are not limited to, Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA), and Cruachem (Glasgow, UK). As such, siRNA molecules are not overly difficult to synthesize and are readily provided in a quality suitable for RNAi.

siRNA can also be produced by in vitro transcription using single-stranded DNA templates (Yu et al., supra). Alternatively, the siRNA molecules can be produced biologically, either transiently (Yu et al., supra; Sui et al. (2002) Proc. Natl. Acad. Sci. USA 99:5515-20) or stably (Paddison et al. (2002) Proc. Natl. Acad. Sci. USA 99:1443-48), using an expression vector(s) containing the sense and antisense siRNA sequences. siRNA can be designed into short hairpin RNA (shRNA) for plasmid- or vector-based approaches for supplying siRNAs to cells. Examples of vectors for shRNA are #AM5779:—pSilencer™ 4.1-CMV neo; #AM5777:—pSilencer™ 4.1-CMV hygro; #AM5775:—pSilencer™ 4.1-CMV puro; #AM7209:—pSilencer™ 2.0-U6; #AM7210:—pSilencer™ 3.0-H1; #AM5768:—pSilencer™ 3.1-H1 puro; #AM5762:—pSilencer™ 2.1-U6 puro; #AM5770:—pSilencer™ 3.1-H1 neo; #AM5764:—pSilencer™ 2.1-U6 neo; #AM5766:—pSilencer™ 3.1-H1 hygro; #AM5760:—pSilencer™ 2.1-U6 hygro; #AM7207:—pSilencer™ 1.0-U6 (circular) from Ambion®.

Reduction of levels of target mRNA in primary human cells, in an efficient and sequence-specific manner, was demonstrated using adenoviral vectors that express hairpin RNAs, which are further processed into siRNAs (Arts et al. (2003) Genome Res. 13:2325-32). In addition, dsRNAs can be expressed as stem loop structures encoded by plasmid vectors, retroviruses and lentiviruses (Paddison, P. J. et al. (2002) Genes Dev. 16:948-958; McManus, M. T. et al. (2002) RNA 8:842-850; Paul, C. P. et al. (2002) Nat. Biotechnol. 20:505-508; Miyagishi, M. et al. (2002) Nat. Biotechnol. 20:497-500; Sui, G. et al. (2002) Proc. Natl. Acad. Sci., USA 99:5515-5520; Brummelkamp, T. et al. (2002) Cancer Cell 2:243; Lee, N. S., et al. (2002) Nat. Biotechnol. 20:500-505; Yu, J. Y., et al. (2002) Proc. Natl. Acad. Sci., USA 99:6047-6052; Zeng, Y., et al. (2002) Mol. Cell. 9:1327-1333; Rubinson, D. A., et al. (2003) Nat. Genet. 33:401-406; Stewart, S. A., et al. (2003) RNA 9:493-501). These vectors generally have a polIII promoter upstream of the dsRNA and can express sense and antisense RNA strands separately and/or as a hairpin structures. Within cells, Dicer processes the short hairpin RNA (shRNA) into effective siRNA.

The targeted region of the siRNA molecule of the present invention can be selected from a target gene sequence, e.g., the coding sequence of a gene of STK38, EXT1, PTPN9, EGLN3, MLH1, and ABCC12 beginning from about 15 to 50 nucleotides, from about 50 to 75 nucleotides, or from about 75 to 100 nucleotides downstream of the start codon. Nucleotide sequences can contain 5' or 3' UTRs and regions near the start codon. One method of designing a siRNA molecule of the present invention involves identifying the 23 nucleotide sequence motif AA(N19)TT (where N can be any nucleotide), and selecting hits with at least 25%, 30%, 35%, 40%, 45%, 50%, 55%, 60%, 65%, 70% or 75% G/C content. The "TT" portion of the sequence is optional. Alternatively, if no such sequence is found, the search can be extended using the motif NA (N21), where N can be any nucleotide. In this situation, the 3' end of the sense siRNA can be converted to TT to allow for the generation of a symmetric duplex with respect to the sequence composition of the sense and antisense 3' overhangs. The antisense siRNA molecule can then be synthesized as the complement to nucleotide positions 1 to 21 of the 23 nucleotide sequence motif. The use of symmetric 3' TT overhangs can be advantageous to ensure that the small interfering ribonucleoprotein particles (siRNPs) are formed with approximately equal ratios of sense and antisense target RNA-cleaving siRNPs (Elbashir et al. (2001) supra and Elbashir et al. 2001 supra). Analysis of sequence databases, including but are not limited to the NCBI, Derwent and GenSeq as well as commercially available oligosynthesis software such as OLIGOENGINE®, can also be used to select siRNA sequences against EST libraries to ensure that only one gene is targeted.

Methods of predicting and selecting antisense oligonucleotides and siRNA are known in the art and are also found at the internet website of various companies, e.g., Genscript, Ambion, Dharmacon, Oigoengine, the Wadsworth organization, and the Whitehead Institute, and also described in U.S. Pat. No. 6,060,248.

In some aspects, antisense nucleic acid technology can be used to inhibit the expression of gene of STK38, EXT1, PTPN9, EGLN3, MLH1, and ABCC12. It is possible to synthesize a strand of nucleic acid (DNA, RNA or a chemical analogue) that will bind to the messenger RNA (mRNA) produced by that gene and inactivate it, effectively turning that gene "off". This synthesized nucleic acid is termed an "anti-sense" oligonucleotide because its base sequence is complementary to the gene's messenger RNA (mRNA), which is called the "sense" sequence (so that a sense segment of mRNA "5'-AAGGUC-3'" would be blocked by the antisense mRNA segment "3'-UUCCAG-5'").

Oligonucleotide Modifications

Unmodified oligonucleotides may be less than optimal in some applications, e.g., unmodified oligonucleotides can be prone to degradation by e.g., cellular nucleases. Nucleases can hydrolyze nucleic acid phosphodiester bonds. However, chemical modifications to one or more of the subunits of oligonucleotide can confer improved properties, and, e.g., can render oligonucleotides more stable to nucleases.

In some circumstances, for example, where increased nuclease stability is desired, nucleic acids having nucleic acid analogs and/or modified internucleoside linkages can be preferred. Nucleic acids containing modified internucleoside linkages can be synthesized using reagents and methods that are well known in the art. For example, methods of synthesizing nucleic acids containing phosphonate phosphorothioate, phosphorodithioate, phosphoramidate methoxyethyl phosphoramidate, formacetal, thioformacetal, diisopropylsilyl, acetamidate, carbamate, dimethylene-sulfide (—CH$_2$—S—CH$_2$), dimethylene-sulfoxide (—CH$_2$—SO—CH$_2$), dimethylene-sulfone (—CH$_2$—SO$_2$—CH$_2$), 2'-O-alkyl, and 2'-deoxy-2'-fluoro'phosphorothioate internucleoside linkages are well known in the art (see Uhlmann et al., 1990, Chem. Rev. 90:543-584; Schneider et al., 1990, Tetrahedron Lett. 31:335 and references cited therein). U.S. Pat. Nos. 5,614,617 and 5,223,618 to Cook, et al., U.S. Pat. No. 5,714,606 to Acevedo, et al, U.S. Pat. No. 5,378,825 to Cook, et al., U.S. Pat. Nos. 5,672,697 and 5,466,786 to Buhr, et al., U.S. Pat. No. 5,777,092 to Cook, et al., U.S. Pat. No. 5,602,240 to De Mesmacker, et al., U.S. Pat. No. 5,610,289 to Cook, et al. and U.S. Pat. No. 5,858,988 to Wang, also describe nucleic acid analogs for enhanced nuclease stability and cellular uptake. These references are incorporated herein by reference in their entirety.

Modified nucleic acids and nucleotide surrogates can include one or more of:

(i) alteration, e.g., replacement, of one or both of the non-linking phosphate oxygens and/or of one or more of the linking phosphate oxygens in the phosphodiester backbone linkage.

(ii) alteration, e.g., replacement, of a constituent of the ribose sugar, e.g., of the 2' hydroxyl on the ribose sugar;

(iii) wholesale replacement of the phosphate moiety with "dephospho" linkers;

(iv) modification or replacement of a naturally occurring base with a non-natural base;

(v) replacement or modification of the ribose-phosphate backbone;

(vi) modification of the 3' end or 5' end of the oligonucleotide, e.g., removal, modification or replacement of a terminal phosphate group or conjugation of a moiety, e.g., a fluorescently labeled moiety, to either the 3' or 5' end of oligonucleotide; and (vii) modification of the sugar (e.g., six membered rings).

The terms replacement, modification, alteration, and the like, as used in this context, do not imply any process limitation, e.g., modification does not mean that one must start with a reference or naturally occurring ribonucleic acid and modify it to produce a modified ribonucleic acid bur rather modified simply indicates a difference from a naturally occurring molecule.

As oligonucleotides are polymers of subunits or monomers, many of the modifications described herein can occur at a position which is repeated within an oligonucleotide, e.g., a modification of a nucleobase, a sugar, a phosphate moiety, or the non-bridging oxygen of a phosphate moiety. It is not necessary for all positions in a given oligonucleotide to be uniformly modified, and in fact more than one of the aforementioned modifications may be incorporated in a single oligonucleotide or even at a single nucleoside within an oligonucleotide.

In some cases the modification will occur at all of the subject positions in the oligonucleotide but in many, and in fact in most cases it will not. By way of example, a modification may only occur at a 3' or 5' terminal position, may only occur in the internal region, may only occur in a terminal regions, e.g. at a position on a terminal nucleotide or in the last 2, 3, 4, 5, or 10 nucleotides of an oligonucleotide. A modification can occur in a double strand region, a single strand region, or in both. A modification can occur only in the double strand region of an oligonucleotide or may only occur in a single strand region of an oligonucleotide. For example., a phosphorothioate modification at a non-bridging oxygen position may only occur at one or both termini, may only occur in a terminal regions, e.g., at a position on a terminal nucleotide or in the last 2, 3, 4, 5, or 10 nucleotides of a strand, or may occur in double strand and single strand regions, particularly at termini. The 5' end or ends can be phosphorylated.

A modification described herein may be the sole modification, or the sole type of modification included on multiple nucleotides, or a modification can be combined with one or more other modifications described herein. The modifications described herein can also be combined onto an oligonucleotide, e.g. different nucleotides of an oligonucleotide have different modifications described herein.

In some embodiments it is particularly preferred, e.g., to enhance stability, to include particular nucleobases in overhangs, or to include modified nucleotides or nucleotide surrogates, in single strand overhangs, e.g., in a 5' or 3' overhang, or in both. E.g., it can be desirable to include purine nucleotides in overhangs. In some embodiments all or some of the bases in a 3' or 5' overhang will be modified, e.g., with a modification described herein. Modifications can include, e.g., the use of modifications at the 2' OH group of the ribose sugar, e.g., the use of deoxyribonucleotides, e.g., deoxythymidine, instead of ribonucleotides, and modifications in the phosphate group, e.g., phosphothioate modifications. Overhangs need not be homologous with the target sequence.

The preparation of phosphinate oligoribonucleotides is described in U.S. Pat. No. 5,508,270. The preparation of alkyl phosphonate oligoribonucleotides is described in U.S. Pat. No. 4,469,863. The preparation of phosphoramidite oligoribonucleotides is described in U.S. Pat. Nos. 5,256,775 or 5,366,878. The preparation of phosphotriester oligoribonucleotides is described in U.S. Pat. No. 5,023,243. The preparation of borano phosphate oligoribonucleotide is described in U.S. Pat. Nos. 5,130,302 and 5,177,198. The preparation of 3'-Deoxy-3'-amino phosphoramidate oligoribonucleotides is described in U.S. Pat. No. 5,476,925. 3'-Deoxy-3'-methylenephosphonate oligoribonucleotides is described in An, H, et al. J. Org. Chem. 2001, 66, 2789-2801. Preparation of sulfur bridged nucleotides is described in Sproat et al. Nucleosides Nucleotides 1988, 7,651 and Crosstick et al. Tetrahedron Lett. 1989, 30, 4693. These references are incorporated herein by reference in their entirety.

Modifications to the 2' positions can be found in Verma, S. et al. Annu. Rev. Biochem. 1998, 67, 99-134 and all references therein. Specific modifications to the ribose can be found in the following references: 2'-fluoro (Kawasaki et. al., J. Med. Chem., 1993, 36, 831-841), 2'-MOE (Martin, P. Hely. Chim. Acta 1996, 79, 1930-1938), "LNA" (Wengel, J. Acc. Chem. Res. 1999, 32, 301-310). These references are incorporated herein by reference in their entirety.

Methylenemethylimino linked oligoribonucleosides, also identified herein as MMI linked oligoribonucleosides, methylenedimethylhydrazo linked oligoribonucleosides, also identified herein as MDH linked oligoribonucleosides, and methylenecarbonylamino linked oligonucleosides, also identified herein as amide-3 linked oligoribonucleosides, and methyleneaminocarbonyl linked oligonucleosides, also identified herein as amide-4 linked oligoribonucleosides as well as mixed backbone compounds having, as for instance, alternating MMI and PO or PS linkages can be prepared as is described in U.S. Pat. Nos. 5,378,825, 5,386,023, 5,489,677 and in published PCT applications PCT/US92/04294 and PCT/US92/04305 (published as WO 92/20822 WO and 92/20823, respectively). Formacetal and thioformacetal linked oligoribonucleosides can be prepared as is described in U.S. Pat. Nos. 5,264,562 and 5,264,564. Ethylene oxide linked oligoribonucleosides can be prepared as is described in U.S. Pat. No. 5,223,618. Siloxane replacements are described in Cormier, J. F. et al. Nucleic Acids Res. 1988, 16, 4583. Carbonate replacements are described in Tittensor, J. R. J. Chem. Soc. C 1971, 1933. Carboxymethyl replacements are described in Edge, M. D. et al. J. Chem. Soc. Perkin Trans. 1 1972, 1991. Carbamate replacements are described in Stirchak, E. P. Nucleic Acids Res. 1989, 17, 6129. These references are incorporated herein by reference in their entirety.

Cyclobutyl sugar surrogate compounds can be prepared as is described in U.S. Pat. No. 5,359,044. Pyrrolidine sugar surrogate can be prepared as is described in U.S. Pat. No. 5,519,134. Morpholino sugar surrogates can be prepared as is described in U.S. Pat. Nos. 5,142,047 and 5,235,033, and other related patent disclosures. Peptide Nucleic Acids (PNAs) are known per se and can be prepared in accordance with any of the various procedures referred to in Peptide Nucleic Acids (PNA): Synthesis, Properties and Potential Applications, Bioorganic & Medicinal Chemistry, 1996, 4, 5-23. They can also be prepared in accordance with U.S. Pat. No. 5,539,083. These references are incorporated herein by reference in their entirety.

Terminal modifications are described in Manoharan, M. et al. Antisense and Nucleic Acid Drug Development 12, 103-128 (2002).

Nucleic acids with nuclebases including N-2 substitued purine nucleoside amidites can be prepared as is described in U.S. Pat. No. 5,459,255. 3-Deaza purine nucleoside amidites can be prepared as is described in U.S. Pat. No. 5,457,191. 5,6-Substituted pyrimidine nucleoside amidites can be prepared as is described in U.S. Pat. No. 5,614,617. 5-Propynyl pyrimidine nucleoside amidites can be prepared as is described in U.S. Pat. No. 5,484,908. These references are incorporated herein by reference in their entirety.

Disclosures regarding the synthesis of particular modified oligonucleotides can be found in the following U.S. patents or pending patent applications: U.S. Pat. Nos. 5,138,045 and 5,218,105, drawn to polyamine conjugated oligonucleotides; U.S. Pat. No. 5,212,295, drawn to monomers for the preparation of oligonucleotides having chiral phosphorus linkages; U.S. Pat. Nos. 5,378,825 and 5,541,307, drawn to oligonucleotides having modified backbones; U.S. Pat. No. 5,386,023, drawn to backbone-modified oligonucleotides and the preparation thereof through reductive coupling; U.S. Pat. No. 5,457,191, drawn to modified nucleobases based on the 3-deazapurine ring system and methods of synthesis thereof; U.S. Pat. No. 5,459,255, drawn to modified nucleobases based on N-2 substituted purines; U.S. Pat. No. 5,521,302, drawn to processes for preparing oligonucleotides having chiral phosphorus linkages; U.S. Pat. No. 5,539,082, drawn to peptide nucleic acids; U.S. Pat. No. 5,554,746, drawn to oligonucleotides having β-lactam backbones; U.S. Pat. No. 5,571,902, drawn to methods and materials for the synthesis of oligonucleotides; U.S. Pat. No. 5,578,718, drawn to nucleosides having alkylthio groups, wherein such groups may be used as linkers to other moieties attached at any of a variety of positions of the nucleoside; U.S. Pat. Nos. 5,587,361 and 5,599,797, drawn to oligonucleotides having phosphorothioate linkages of high chiral purity; U.S. Pat. No. 5,506,351, drawn to processes for the preparation of 2'-O-alkyl guanosine and related compounds, including 2,6-diaminopurine compounds; U.S. Pat. No. 5,587,469, drawn to oligonucleotides having N-2 substituted purines; U.S. Pat. No. 5,587,470, drawn to oligonucleotides having 3-deazapurines; U.S. Pat. Nos. 5,223,168 and 5,608,046, both drawn to conjugated 4'-desmethyl nucleoside analogs; U.S. Pat. Nos. 5,602,240, and 5,610,289, drawn to backbone-modified oligonucleotide analogs; and U.S. Pat. Nos. 6,262,241, and 5,459,255, drawn to, inter alia, methods of synthesizing 2'-fluoro-oligonucleotides. All these references are incorporated herein by reference in their entirety.

Delivery of RNAi Agents

In a preferred embodiment, the siRNA or modified siRNA is delivered in a pharmaceutically acceptable carrier. Additional carrier agents, such as liposomes, can be added to the pharmaceutically acceptable carrier.

In another embodiment, the siRNA is delivered by delivering a vector encoding small hairpin RNA (shRNA) in a pharmaceutically acceptable carrier to the cells in an organ of an individual. The shRNA is converted by the cells after transcription into a siRNA capable of targeting the gene of STK38, EXT1, PTPN9, EGLN3, MLH1, and ABCC12. In one embodiment, the vector can be a plasmid, a cosmid, a phagmid, a hybrid thereof, or a virus. In one embodiment, the vector can be a regulatable vector, such as a tetracycline inducible vector.

In one embodiment, the RNA interfering agents used in the methods described herein are taken up actively by cells in vivo following intravenous injection, e.g., hydrodynamic injection, without the use of a vector, illustrating efficient in vivo delivery of the RNA interfering agents, e.g., the siRNAs used in the methods described herein.

Other strategies for delivery of the RNA interfering agents, e.g., the siRNAs or shRNAs used in the methods described herein, can also be employed, such as, for example, delivery by a vector, e.g., a plasmid or viral vector, e.g., a lentiviral vector. Such vectors can be used as described, for example, in Xiao-Feng Qin et al. Proc. Natl. Acad. Sci. U.S.A., 100: 183-188. Other delivery methods include delivery of the RNA interfering agents, e.g., the siRNAs or shRNAs described herein, using a basic peptide by conjugating or mixing the RNA interfering agent with a basic peptide, e.g., a fragment of a TAT peptide, mixing with cationic lipids or formulating into particles.

As noted, the dsRNA, such as siRNA or shRNA can be delivered using an inducible vector, such as a tetracycline inducible vector. Methods described, for example, in Wang et al. Proc. Natl. Acad. Sci. 100: 5103-5106, using pTet-On vectors (BD Biosciences Clontech, Palo Alto, Calif.) can be used. In some embodiments, a vector can be a plasmid vector, a viral vector, or any other suitable vehicle adapted for the insertion and foreign sequence and for the introduction into eukaryotic cells. The vector can be an expression vector capable of directing the transcription of the DNA sequence of the agonist or antagonist nucleic acid molecules into RNA. Viral expression vectors can be selected from a group including, for example, retroviruses, lentiviruses, Epstein Barr virus-, bovine papilloma virus, adenovirus- and adeno-associated-based vectors or hybrid virus of any of the above. In one embodiment, the vector is episomal. The use of a suitable episomal vector provides a means of maintaining the antagonist nucleic acid molecule in the subject in high copy number extra chromosomal DNA thereby eliminating potential effects of chromosomal integration.

Methods of delivering RNA interfering agents, e.g., an siRNA, or vectors containing an RNA interfering agent, to the target cells (e.g., the HSPCs), can include, for example (i) injection of a composition containing the RNA interfering agent, e.g., an siRNA, or (ii) directly contacting the cell, e.g., a HSPC, with a composition comprising an RNAi agent, e.g., an siRNA or shRNA. In one embodiment, the RNAi agent can be targeted to the bone marrow where the lymphocytes expressing STK38, EXT1, PTPN9, EGLN3, MLH1, and ABCC12 are made. In another embodiment, RNAi agents, e.g., an siRNA can be injected directly into any blood vessel, such as vein, artery, venule or arteriole, via, e.g., hydrodynamic injection or catheterization (see U.S. Pat. No. 7,148, 205). In yet another embodiment, the RNAi agent can be injected or applied topically.

Administration can be by a single administration (e.g. injection) or by two or more administrations. The RNA interfering agent is delivered in a pharmaceutically acceptable carrier. One or more RNA interfering agents can be used simultaneously. The RNA interfering agents, e.g., the siRNAs targeting the mRNA of genes of STK38, EXT1, PTPN9, EGLN3, MLH1, and ABCC12, can be delivered singly, or in combination with other RNAi agents, e.g., siRNAs, such as, for example siRNAs directed to other cellular genes. siRNAs targeting the gene of STK38, EXT1, PTPN9, EGLN3, MLH1, and ABCC12 can also be administered in combination with other pharmaceutical agents such as those that mobilize HSPC from the bone marrow or stimulate in vivo expansion of HSPCs.

In one embodiment, specific cells are targeted with RNA interference, limiting potential side effects of RNA interference caused by non-specific targeting of RNA interference. The method can use, for example, a complex or a fusion molecule comprising a cell targeting moiety and an RNA interference binding moiety that is used to deliver RNA interference effectively into cells. For example, an antibody-protamine fusion protein when mixed with an siRNA, binds siRNA and selectively delivers the siRNA into cells expressing an antigen recognized by the antibody, resulting in silencing of gene expression only in those cells that express the antigen, e.g. CD34. The siRNA or RNA interference-mediating molecule binding moiety is a protein or a nucleic acid binding domain or fragment of a protein, and the binding moiety is fused to a portion of the targeting moiety. The location of the targeting moiety can be either in the carboxyl-terminal or amino-terminal end of the construct or in the middle of the fusion protein.

A viral-mediated delivery mechanism can also be employed to deliver siRNAs to cells in vitro and in vivo as described in Xia, H. et al. (2002) Nat Biotechnol 20(10): 1006). Plasmid- or viral-mediated delivery mechanisms of shRNA can also be employed to deliver shRNAs to cells in vitro and in vivo as described in Rubinson, D. A., et al. ((2003) Nat. Genet. 33:401-406) and Stewart, S. A., et al. ((2003) RNA 9:493-501).

RNAi agents, for e.g., an siRNA and shRNA, can also be introduced into cells via the vascular or extravascular circulation, the blood or lymph system, and the cerebrospinal fluid.

In another embodiment, the RNAi agent such as siRNA is delivered by using a fusion protein comprising a transduction domain (PTD) and a double-stranded RNA binding domain (DRBD). PTD is a short peptide that can be covalently linked to a macromolecule cargo and delivered into a cell. The PTD can be enzymatically cleaved after entering the cell, liberation the siRNA. A fusion protein of PTD-DRBD is used to coat siRNA and deliver the siRNA into the cell (Steve Dowdy, 2009, Nature Biotechnology).

In another embodiment, the RNAi agent such as siRNA is delivered by using polymers that encapsulate the RNAi agent. For example, a cationic polymer comprising a branched lysine and histidine polypeptide that acts like an siRNA condenser and protects the molecule from degradation. For example, one study reports a system to deliver DNA in vitro by covalently attaching the surfactant associated protein B (SP-B) to a 10 kDa poly-lysine. See, Baatz, J., et al., PNAS USA, 91:2547-2551 (1994). See, e.g., Longmuir, et al., 1992 ASBMB/Biophysical Society abstract; Longmuir, et al., 1993 Biophysical Society abstract. In other embodiments, polyethylene glycol (PEG) can be included in the encapsulation to improve the pharmacokinetics of the RNAi agent.

Liposomes, spherical, self-enclosed vesicles composed of amphipathic lipids, have been widely studied and are employed as vectors for in vivo administration of therapeutic agents. In particular, the so-called long circulating liposome formulations which avoid uptake by the organs of the mononuclear phagocyte system, primarily the liver and spleen, have found commercial applicability. Such long-circulating liposomes include a surface coat of flexible water soluble polymer chains, which act to prevent interaction between the liposome and the plasma components which play a role in liposome uptake. Alternatively, hyaluronan has been used as a surface coating to maintain long circulation.

In one embodiment, the liposome encapsulates the RNAi agent, nucleic acid sequences, vectors or even the viral particles. In one embodiment, the nucleic acid sequences or vectors are condensed with a cationic polymer, e.g., PEI, polyamine spermidine, and spermine, or a cationic peptide, e.g., protamine and poly-lysine, and encapsulated in the lipid particle. The liposomes can comprise multiple layers assembled in a step-wise fashion.

Lipid materials are well known and routinely utilized in the art to produce liposomes. Lipids may include relatively rigid varieties, such as sphingomyelin, or fluid types, such as phospholipids having unsaturated acyl chains. "Phospholipid" refers to any one phospholipid or combination of phospholipids capable of forming liposomes. Phosphatidylcholines (PC), including those obtained from egg, soy beans or other plant sources or those that are partially or wholly synthetic, or of variable lipid chain length and unsaturation are suitable for use in the methods and compositions described herein. Synthetic, semisynthetic and natural product phosphatidylcholines including, but not limited to, distearoylphosphatidylcholine (DSPC), hydrogenated soy phosphatidylcholine (HSPC), soy phosphatidylcholine (soy PC), egg phosphatidylcholine (egg PC), hydrogenated egg phosphatidylcholine (HEPC), dipalmitoylphosphatidylcholine (DPPC) and dimyristoylphosphatidylcholine (DMPC) are suitable phosphatidylcholines for use in the methods and compositions described herein. All of these phospholipids are commercially available. Further, phosphatidylglycerols (PG) and phosphatic acid (PA) are also suitable phospholipids for use in the present invention and include, but are not limited to, dimyristoylphosphatidylglycerol (DMPG), dilaurylphosphatidylglycerol (DLPG), dipalmitoylphosphatidylglycerol (DPPG), distearoylphosphatidylglycerol (DSPG) dimyristoylphosphatidic acid (DMPA), distearoylphosphatidic acid (DSPA), dilaurylphosphatidic acid (DLPA), and dipalmitoylphosphatidic acid (DPPA). Distearoylphosphatidylglycerol (DSPG) is the preferred negatively charged lipid when used in formulations. Other suitable phospholipids include phosphatidylethanolamines, phosphatidylinositols, sphingomyelins, and phosphatidic acids containing lauric, myristic, stearoyl, and palmitic acid chains. For the purpose of stabilizing the lipid membrane, it is preferred to add an additional lipid component, such as cholesterol. Preferred lipids for producing liposomes according the methods and compositions described herein include phosphatidylethanolamine (PE) and phosphatidylcholine (PC) in further combination with cholesterol (CH). According to one embodiment, a combination of lipids and cholesterol for producing liposomes comprise a PE:PC:Chol molar ratio of 3:1:1. Further, incorporation of polyethylene glycol (PEG) containing phospholipids is also contemplated.

In addition, in order to prevent the uptake of the liposomes into the cellular endothelial systems and enhance the uptake of the liposomes into the tissue of interest, the outer surface of the liposomes may be modified with a long-circulating agent. The modification of the liposomes with a hydrophilic polymer as the long-circulating agent is known to enable to prolong the half-life of the liposomes in the blood Liposomes encapsulating the nucleic acid sequences described herein can be obtained by any method known to the skilled artisan. For example, the liposome preparation of the methods and compositions described herein can be produced by reverse phase evaporation (REV) method (see U.S. Pat. No. 4,235,871), infusion procedures, or detergent dilution. A review of these and other methods for producing liposomes may be found in the text Liposomes, Marc Ostro, ed., Marcel Dekker, Inc., New York, 1983, Chapter 1. See also Szoka Jr. et al., (1980, Ann. Rev. Biophys. Bioeng., 9:467).

The dose of the particular RNA interfering agent will be in an amount necessary to effect RNA interference, e.g., post translational gene silencing (PTGS), of the particular target gene, thereby leading to inhibition of target gene expression or inhibition of activity or level of the protein encoded by the target gene.

It is also known that RNAi agents do not have to match perfectly to their target sequence. Preferably, however, the 5' and middle part of the antisense (guide) strand of the siRNA is perfectly complementary to the target nucleic acid sequence.

Accordingly, the RNAi agents of the genes of STK38, EXT1, PTPN9, EGLN3, MLH1, and ABCC12 disclosed herein include, for example, but are not limited to, unmodified and modified double stranded (ds) RNA molecules including short-temporal RNA (stRNA), small interfering RNA (siRNA), short-hairpin RNA (shRNA), microRNA (miRNA), double-stranded RNA (dsRNA), (see, e.g. Baulcombe, Science 297:2002-2003, 2002). The dsRNA molecules, e.g. siRNA, also can contain 3' overhangs, preferably 3'UU or 3'TT overhangs. In one embodiment, the siRNA molecules do not include RNA molecules that comprise ssRNA greater than about 30-40 bases, about 40-50 bases, about 50 bases or more. In one embodiment, the siRNA molecules are double stranded for more than about 25%, more than about 50%, more than about 60%, more than about 70%, more than about 80%, or more than about 90% of their length. In some embodiments, an RNAi agent binds to and inhibits the expression of mRNA of STK38, EXT1, PTPN9, EGLN3, MLH1, and ABCC12, wherein the mRNA is found at GENBANK™ Accession Nos.: NM_007271.2, NM_000127, NM_033123.2, NM_002833, NM_022073.3, NM_000249.3, NM_001167617.1, NM_001167618.1, NM_001167619.1, and NM_033226.2.

In another embodiment, agents inhibiting the genes of STK38, EXT1, PTPN9, EGLN3, MLH1, and ABCC12 are catalytic nucleic acid constructs, such as, for example ribozymes, which are capable of cleaving RNA transcripts and thereby preventing the production of wildtype protein. Ribozymes are targeted to and anneal with a particular sequence by virtue of two regions of sequence complementary to the target flanking the ribozyme catalytic site. After binding, the ribozyme cleaves the target in a site specific manner. The design and testing of ribozymes which specifically recognize and cleave sequences of the gene products described herein, for example, for the cleavage of the genes of STK38, EXT1, PTPN9, EGLN3, MLH1, and ABCC12 or homologues or variants thereof can be achieved by techniques well known to those skilled in the art (for example Lleber and Strauss, (1995) Mol Cell Biol 15:540.551, the disclosure of which is incorporated herein by reference in it entirety).

Isolation of Mononuclear CD34 Positive Hematopoietic Stem Progenitor Cells

Sources of CD34 positive hematopoietic stem progenitor cells (HSPCs) are the bone marrow of adults, which includes femurs, hip, ribs, sternum, other bones, umbilical cord blood, placenta, mobilized peripheral blood, fetal liver, fetal spleen, and AGM (Aorta-gonad-mesonephros) of animals. Pre-treatment with cytokines, such as G-CSF (granulocyte colony-stimulating factors), can induce cells to be released from the bone marrow compartment.

For example, growth factors GM-CSF and G-CSF can be administered to a potential donor of HSPC to mobilize the existing HSPC in the bone marrow niches to the peripheral circulating blood in vivo in order to increase the fraction of HSPCs circulating in the blood.

These HSPCs can be isolated by any methods known the art, e.g. as disclosed herein and in U.S. Pat. No. 7,510,877, U.S Patent Publication No. 20090215083 and 20090169523, and WO/WO/2009/129288 and WO/2005/030040. These references are incorporated herein by reference in their entirety.

Cells can be obtained directly by removal from the hip using a needle and syringe, or from the blood. For example, collect peripheral blood in heparinized syringes or VACU-TAINERS®. Immediately mix the samples gently to prevent clotting. Cord blood and leukapheresis product from mobilized peripheral blood should already be heparinized. Dilute the sample with Hank's Buffered Saline Solution (HBSS) before proceeding to FICOLL-PAQUE™ gradient centrifugation. For whole blood, dilute with an equal volume of HBSS. For leukapheresis product, dilute with three volumes of PBS. Add the diluted sample to 50 mL sterile centrifuge tubes. Underlay the diluted sample with 15 mL of sterile FICOLL-PAQUE™ PLUS. Centrifuge at 400×g for 20 minutes with the brake off. Carefully harvest the mononuclear HSPCs from the interface between the FICOLL-PAQUE™ PLUS and sample buffer using a sterile Pasteur pipette. Transfer the cells to sterile centrifuge tubes. Wash with an equal volume of HBSS and centrifuge for 10 minutes at 400×G to remove the FICOLL-PAQUE™ PLUS residue. If multiple tubes are used, pool the cells together and wash a second time in a large volume of HBSS. The CD34$^+$ population of HSPCs can be further enriched using standard enrichment procedures that are known in the art.

The HSPCs can be isolated from fresh and frozen mononuclear cells of peripheral blood, cord blood, and bone marrow using its pan-hematopoietic antigen CD34 or by other methods that are known to one skilled in the art. For example, antibodies against CD34 can be used for immuno-isolating the CD34$^+$ hematopoietic progenitor cells from the mononuclear cell fraction. The anti-CD34 antibodies can be conjugated with fluorophores or to magnetic beads for ease of separation by FACS or magnets respectively.

HSPCs bearing the pan-hematopoietic antigen CD34 can also be isolated by taking advantage of the cells ability to bind galactose-conjugated proteins. This lectin-positive sub-population represents approximately 0.1 to 0.5% of the total bone marrow cells, and contains 100% of the hematopoietic progenitor cells. The galactose-binding lectin on these cells is specific for this sugar. Additionally, highly proliferative hematopoietic progenitor cells with very primitive phenotypes, including a progenitor cell that produces multiple lineages, express this lectin. (Pipia and Long, Nature Biotechnology, 1997, 15:007-1011).

In some embodiments, the CD34$^+$ population of HSPCs can be enriched using surface markers such as CD38, CD45RA, CD 90 and CD133. The further enrichment of HSPCs can be made by negative selection for CD38 and CD45RA, and positive selection for CD90 and/or CD133 in addition to CD34 (see: Cell Stem Cell 2007, 1(6):635-45) e.g. using CD133 or CD38 affinity chromatography or FACS.

Hematopoietic Stem Progenitor Cell Culture Media

Culture media suitable for the ex vivo culturing of HSPCs according to the practice described herein are well known in the art, e.g. as disclosed in U.S. Pat. No. 6,030,836, and by J. Hartshorn, et al., "Ex Vivo Expansion of Hematopoietic Stem Cells Using Defined Culture Media" in Cell Technology for Cell Products, Chapter III, pages 221-224. Such culture media include but are not limited to high glucose Dulbecco's Modified Eagles Medium (DMEM) with L-Glutamine which is well known and readily commercially available. The media can be supplemented with recombinant human basic fibroblast growth factor (rhbFGF) and contain sera, such as human serum, and antibiotics. Cell cultures are maintained in a $CO_2$ atmosphere, e.g., 5% to 12%, to maintain pH of the culture fluid, and incubated at 37° C. in a humid atmosphere. Suitable chemically defined serum-free media are described in U.S. Ser. No. 08/464,599 and WO96/39487, and "complete media" are described in U.S. Pat. No. 5,486,359 and these are hereby incorporated by reference. Chemically defined medium comprises a minimum essential medium such as Iscove's Modified Dulbecco's Medium (IMDM) (Gibco), supplemented with human serum albumin, human Ex Cyte lipoprotein, transferrin, insulin, vitamins, essential and non essential amino acids, sodium pyruvate, glutamine and a mitogen. These media stimulate cell growth without differentiation. As used herein, a mitogen refers to an agent that stimulates cell division of a cell. Such an agent can be a chemical, usually some form of a protein that encourages a cell to commence cell division triggering mitosis. Other examples of culture medium include RPMI 1640, Iscove's modified Dubelcco's media (IMDM), and Opti-MEM SFM (Invitrogen Inc.). Chemically Defined Medium comprises a minimum essential medium such as Iscove's Modified Dulbecco's Medium (IMDM) (Gibco), supplemented with human serum albumin, human Ex Cyte lipoprotein, transferrin, insulin, vitamins, essential and non essential amino acids, sodium pyruvate, glutamine and a mitogen is also suitable.

Commercial culture media for hematopoietic stem progetitor cells are also available, e.g. STEMPRO®-34 SFM form INVITROGEN™ Inc., MACS® HSC-CFU Media from Miltenyl Biotech, STEMSPAN® SFEM Medium and STEMSPAN® CC110-STEMSPAN® Cytokine Cocktail from STEMCELL Technologies, Inc.

The commercial formulation can be supplemented with 3700 mg/l of sodium bicarbonate and 10 ml/l of a 100× (100 times concentrated) antibiotic-antimycotic cocktail containing 10,000 units of penicillin, 10,000 µg of streptomycin, and 25 µg of amphotericin B/ml utilizing penicillin G (sodium salt), streptomycin sulfate, and amphotericin B (FUNGI-ZONE™) in 0.85% saline. In addition, cocktails of cytokines e.g. GM-CSF, G-CSF, SCF, IL-3, IL-6, and Epo can be included (J. Hartshorn, et al., supra).

Other culture media supplements include platelet rich plasma supplemented with heparin (2 U/ml); the basic fibroblast growth factor (bFGF) recombinant human basic fibroblast growth factor (rhubFGF), granulocyte macrophage colony-stimulating factor (GM-CSF), granulocyte colony-stimulating factor (G-CSF), stem cell factor (SCF), interleukin-3 (IL-3), interleukin-6 (IL-6), interleukin-9 (IL-9), thrombopoietin (TPO) and erythropoetin (Epo).

Cryopreservation of Hematopoietic Stem Progenitor Cells

As used herein, "cryopreservation" refers to the preservation of cells by cooling to low sub-zero temperatures, such as (typically) 77 K or −196° C. (the boiling point of liquid nitrogen). Cryopreservation also refers to storing the cells at a temperature between 0-10° C. in the absence of any cryopreservative agents. At these low temperatures, any biological activity, including the biochemical reactions that would lead to cell death, is effectively stopped. Cryoprotective agents are often used at sub-zero temperatures to preserve the cells from damages due to freezing at low temperatures or warming to room temperature.

In one embodiment, described herein is a cryopreserved pharmaceutical composition comprising: (a) an isolated cell population comprising an HSPC that has been contacted with at least one RNAi agent which comprises at least 15 contiguous nucleotides differing by no more than 3 nucleotides from a sequence selected from the group consisting of SEQ ID NOS: 2, 5, 8, 9, 16, 17, and 18, and/or contacted with at least one agent which inhibits a protein selected from the group consisting of EXT1, PLCZ1, PTPN9, EGLN3, MLH1 and ABCC12 according to the method described herein; (b) an amount of cryopreservative or cryoprotective agent sufficient for the cryopreservation of HSPCs; and (c) a pharmaceutically acceptable carrier.

Freezing is destructive to most living cells. Upon cooling, as the external medium freezes, cells equilibrate by losing water, thus increasing intracellular solute concentration. Below about −10°-15° C., intracellular freezing will occur. Both intracellular freezing and solution effects are responsible for cell injury (Mazur, P., 1970, Science 168:939-949). It has been proposed that freezing destruction from extracellular ice is essentially a plasma membrane injury resulting from osmotic dehydration of the cell (Meryman, H. T., et al., 1977, Cryobiology 14:287-302).

Cryoprotective agents and optimal cooling rates can protect against cell injury. Cryoprotection by solute addition is thought to occur by two potential mechanisms: colligatively, by penetration into the cell, reducing the amount of ice formed; or kinetically, by decreasing the rate of water flow out of the cell in response to a decreased vapor pressure of external ice (Meryman, H. T., et al., 1977, Cryobiology 14:287-302). Different optimal cooling rates have been described for different cells. Various groups have looked at the effect of cooling velocity or cryopreservative upon the survival or transplantation efficiency of frozen bone marrow cells or red blood cells (Lovelock, J. E. and Bishop, M. W. H., 1959, Nature 183:1394-1395; Ashwood-Smith, M. J., 1961, Nature 190:1204-1205; Rowe, A. W. and Rinfret, A. P., 1962, Blood 20:636; Rowe, A. W. and Fellig, J., 1962, Fed. Proc. 21:157; Rowe, A. W., 1966, Cryobiology 3(1):12-18; Lewis, J. P., et al., 1967, Transfusion 7(1):17-32; Rapatz, G., et al., 1968, Cryobiology 5(1):18-25; Mazur, P., 1970, Science 168:939-949; Mazur, P., 1977, Cryobiology 14:251-272; Rowe, A. W. and Lenny, L. L., 1983, Cryobiology 20:717; Stiff, P. J., et al., 1983, Cryobiology 20:17-24; Gorin, N. C., 1986, Clinics in Haematology 15(1):19-48).

The successful recovery of human bone marrow cells after long-term storage in liquid nitrogen has been described (1983, American Type Culture Collection, Quarterly Newsletter 3(4):1). In addition, stem cells in bone marrow were shown capable of withstanding cryopreservation and thawing without significant cell death, as demonstrated by the ability to form equal numbers of mixed myeloid-erythroid colonies in vitro both before and after freezing (Fabian, I., et al., 1982, Exp. Hematol. 10:119-122). The cryopreservation and thawing of human fetal liver cells (Zuckerman, A. J., et al., 1968, J. Clin. Pathol. (London) 21(1):109-110), fetal myocardial cells (Robinson, D. M. and Simpson, J. F., 1971, In Vitro 6(5):378), neonatal rat heart cells (Alink, G. M., et al., 1976, Cryobiology 13:295-304), and fetal rat pancreases (Kemp, J. A., et al., 1978, Transplantation 26(4):260-264) have also been reported.

The injurious effects associated with freezing can be circumvented by (a) use of a cryoprotective agent, (b) control of the freezing rate, and (c) storage at a temperature sufficiently low to minimize degradative reactions.

Cryoprotective agents which can be used include but are not limited to dimethyl sulfoxide (DMSO) (Lovelock, J. E. and Bishop, M. W. H., 1959, Nature 183:1394-1395; Ashwood-Smith, M. J., 1961, Nature 190:1204-1205), glycerol, polyvinylpyrrolidine (Rinfret, A. P., 1960, Ann. N.Y. Acad. Sci. 85:576), polyethylene glycol (Sloviter, H. A. and Ravdin, R. G., 1962, Nature 196:548), albumin, dextran, sucrose, ethylene glycol, i-erythritol, D-Sorbitol, D-mannitol (Rowe, A. W., et al., 1962, Fed. Proc. 21:157), D-sorbitol, i-inositol, D-lactose, choline chloride (Bender, M. A., et al., 1960, J. Appl. Physiol. 15:520), amino acids (Phan The Tran and Bender, M. A., 1960, Exp. Cell Res. 20:651), methanol, acetamide, glycerol monoacetate (Lovelock, J. E., 1954, Biochem. J. 56:265), and inorganic salts (Phan The Tran and Bender, M. A., 1960, Proc. Soc. Exp. Biol. Med. 104:388; Phan The Tran and Bender, M. A., 1961, in Radiobiology, Proceedings of the Third Australian Conference on Radiobiology, Ilbery, P. L. T., ed., Butterworth, London, p. 59). In a preferred embodiment, DMSO is used, a liquid which is non-toxic to cells in low concentration. Being a small molecule, DMSO freely permeates the cell and protects intracellular organelles by combining with water to modify its freezability and prevent damage from ice formation. Addition of plasma (e.g., to a concentration of 20-25%) can augment the protective effect of DMSO. After addition of DMSO, cells should be kept at 0-4° C. until freezing, since DMSO concentrations of about 1% are toxic at temperatures above 4° C.

A controlled slow cooling rate is critical. Different cryoprotective agents (Rapatz, G., et al., 1968, Cryobiology 5(1):18-25) and different cell types have different optimal cooling rates (see e.g., Rowe, A. W. and Rinfret, A. P., 1962, Blood 20:636; Rowe, A. W., 1966, Cryobiology 3(1):12-18; Lewis, J. P., et al., 1967, Transfusion 7(1):17-32; and Mazur, P., 1970, Science 168:939-949 for effects of cooling velocity on survival of marrow-stem cells and on their transplantation potential). The heat of fusion phase where water turns to ice should be minimal. The cooling procedure can be carried out by use of, e.g., a programmable freezing device or a methanol bath procedure.

Programmable freezing apparatuses allow determination of optimal cooling rates and facilitate standard reproducible cooling. Programmable controlled-rate freezers such as Cryomed or Planar permit tuning of the freezing regimen to the desired cooling rate curve. For example, for marrow cells in 10% DMSO and 20% plasma, the optimal rate is 1 to 3° C./minute from 0° C. to −80° C. In one embodiment, this cooling rate can be used for the HSPCs described herein. The container holding the cells must be stable at cryogenic temperatures and allow for rapid heat transfer for effective control of both freezing and thawing. Sealed plastic vials (e.g., Nunc, Wheaton CRYULES®) or glass ampules can be used for multiple small amounts (1-2 ml), while larger volumes (100-200 ml) can be frozen in polyolefin bags (e.g., Delmed) held between metal plates for better heat transfer during cooling. (Bags of bone marrow cells have been successfully frozen by placing them in −80° C. freezers which, fortuitously, gives a cooling rate of approximately 3° C./minute).

In an alternative embodiment, the methanol bath method of cooling can be used. The methanol bath method is well-suited to routine cryopreservation of multiple small items on a large scale. The method does not require manual control of the freezing rate nor a recorder to monitor the rate. In a preferred aspect, DMSO-treated cells are pre-cooled on ice and transferred to a tray containing chilled methanol which is placed, in turn, in a mechanical refrigerator (e.g., Harris or Revco) at −80° C. Thermocouple measurements of the methanol bath and the samples indicate the desired cooling rate of 1° to 3° C./minute. After at least two hours, the specimens have reached a temperature of −80° C. and can be placed directly into liquid nitrogen (−196° C.) for permanent storage.

After thorough freezing, cells can be rapidly transferred to a long-term cryogenic storage vessel. In a preferred embodiment, HSPC samples can be cryogenically stored in liquid nitrogen (−196° C.) or its vapor (−165° C.).

In a particular embodiment, the cryopreservation procedure described in Current Protocols in Stem Cell Biology, 2007, (Mick Bhatia, et. al., ed., John Wiley and Sons, Inc.) is used in the methods described herein and is hereby incorporated by reference. Mainly when the HSPCs on a 10-cm tissue culture plate have reached approximately 50% confluency, the media within the plate is aspirated and the HSPCs are rinsed with phosphate buffered saline. The adherent HSPCs are then detached by 3 ml of 0.025% trypsin/0.04% EDTA treatment. The trypsin/EDTA is neutralized by 7 ml of media and the detached HSPC are collected by centrifugation at 200×g for 2 min. The supernatant is aspirated off and the pellet of HSPCs is resuspended in 1.5 ml of media. An aliquot of 1 ml of 100% DMSO is added to the suspension of HSPCs and gently mixed. Then 1 ml aliquot of this suspension of HSPCs in DMSO is dispensed into cryules in preparation for cryopreservation. The sterilized storage cryules preferably have their caps threaded inside, allowing easy handling without contamination. Suitable racking systems are commercially available and can be used for cataloguing, storage, and retrieval of individual specimens.

Considerations and procedures for the manipulation, cryopreservation, and long-term storage of hematopoietic stem progenitor cells, particularly from bone marrow or peripheral blood, can be found, for example, in the following references, incorporated by reference herein: Gorin, N.C., 1986, Clinics In Haematology 15(1):19-48; Bone-Marrow Conservation, Culture and Transplantation, Proceedings of a Panel, Moscow, Jul. 22-26, 1968, International Atomic Energy Agency, Vienna, pp. 107-186.

Other methods of cryopreservation of viable cells, or modifications thereof, are available and contemplated for use (e.g., cold metal-minor techniques; Livesey, S. A. and Linner, J. G., 1987, Nature 327:255; Linner, J. G., et al., 1986, J. Histochem. Cytochem. 34(9):1123-1135; U.S. Pat. Nos. 4,199,022, 3,753,357, 4,559,298 and are incorporated hereby reference.

Recovering Hematopoietic Stem Progenitor Cells from the Frozen State

Frozen HSPCs are preferably thawed quickly (e.g., in a water bath maintained at 37°-41° C.) and chilled on ice immediately upon thawing. In particular, the cryogenic vial containing the frozen HSPCs can be immersed up to its neck in a warm water bath; gentle rotation will ensure mixing of the cell suspension as it thaws and increase heat transfer from the warm water to the internal ice mass. As soon as the ice has completely melted, the vial can be immediately placed in ice.

In a particular embodiment, the thawing procedure after cryopreservation is that described in Current Protocols in Stem Cell Biology 2007 (Mick Bhatia, et. al., ed., John Wiley and Sons, Inc.) which is incorporated herein by reference. Immediately after removing the cryogenic vial from the cryofreezer, the vial is rolled between the hands for 10 to 30 sec until the outside of the vial is frost free. The vial is then held upright in a 37° C. water-bath until the contents are visibly thawed. The vial is immersed in 95% ethanol or sprayed with 70% ethanol to kill microorganisms from the water-bath and air dry in a sterile hood. The contents of the vial are then transferred to a 10-cm sterile culture containing 9 ml of media using sterile techniques. The HSPCs can then be cultured and further expanded in a incubator at 37° C. with 5% humidified $CO_2$.

In some embodiments, the HSPCs are treated in order to prevent cellular clumping upon thawing. To prevent clumping, various procedures can be used, including but not limited to, the addition before and/or after freezing of DNase (Spitzer, G., et al., 1980, Cancer 45:3075-3085), low molecular weight dextran and citrate, hydroxyethyl starch (Stiff, P. J., et al., 1983, Cryobiology 20:17-24).

The cryoprotective agent, if toxic in humans, should be removed prior to therapeutic use of the thawed HSPCs. In an embodiment employing DMSO as the cryopreservative, it is preferable to omit this step in order to avoid cell loss, since DMSO has no serious toxicity. However, where removal of the cryoprotective agent is desired, the removal is preferably accomplished upon thawing.

One way in which to remove the cryoprotective agent is by dilution to an insignificant concentration. This can be accomplished by addition of medium, followed by, if necessary, one or more cycles of centrifugation to pellet the cells, removal of the supernatant, and resuspension of the cells. For example, the intracellular DMSO in the thawed cells can be reduced to a level (less than 1%) that will not adversely affect the recovered cells. This is preferably done slowly to minimize potentially damaging osmotic gradients that occur during DMSO removal.

After removal of the cryoprotective agent, cell count (e.g., by use of a hemocytometer) and viability testing (e.g., by trypan blue exclusion; Kuchler, R. J. 1977, Biochemical Methods in Cell Culture and Virology, Dowden, Hutchinson & Ross, Stroudsburg, Pa., pp. 18-19; 1964, Methods in Medical Research, Eisen, H. N., et al., eds., Vol. 10, Year Book Medical Publishers, Inc., Chicago, pp. 39-47) can be done to confirm cell survival.

Other procedures which can be used, relating to processing of the thawed cells, include enrichment for adherent HSPCs and expansion by in vitro culture as described supra.

In a preferred, but not required, in some embodiments, thawed cells are tested by standard assays for viability (e.g., trypan blue exclusion) and for microbial sterility by any methods known in the art, and tested to confirm and/or determine their identity relative to the recipient.

Methods for identity testing which can be used include but are not limited to HLA typing (Bodmer, W., 1973, in Manual of Tissue Typing Techniques, Ray, J. G., et al., eds., DHEW Publication No. (NIH) 74-545, pp. 24-27), and DNA fingerprinting, which can be used to establish the genetic identity of the cells. DNA fingerprinting (Jeffreys, A. J., et al., 1985, Nature 314:67-73) exploits the extensive restriction fragment length polymorphism associated with hypervariable minisatellite regions of human DNA, to enable identification of the origin of a DNA sample, specific to each individual (Jeffreys, A. J., et al., 1985, Nature 316:76; Gill, P., et al., 1985, Nature 318:577; Vassart, G., et al., 1987, Science 235:683), and is thus preferred for use.

In a specific embodiment in which the HSPCs recovered for implantation are to be used in an autologous system, the HSPCs should match exactly the recipient patient from whom the HSPCs are originally derived. In another embodiment, the HSPCs are not used in an autologous system but are HLA typed match to the recipient. For example, the HLA type matched for HLA-A, B, C, and D.

Colony Forming Cell (CFC) Assay Using Methylcellulose-Based Media

The colony forming cell (CFC) assay, also referred to as the methylcellulose assay, is an in vitro assay used in the study of hematopoietic stem progenitor cells (HSPCs). The assay is based on the ability of HSPCs to proliferate and differentiate into colonies in a semi-solid media in response to specific cytokine stimulation. The colonies formed can be enumerated and characterized according to their unique morphology.

CFC assays are well known to those skilled in the art and are also described herein. The following is a general description of the method. Aliquots of methylcellulose-based media and cell resuspension solution (Catalog # HSC002, HSC003, HSC004, and HSC005 form STEMCELL Technologies) are thawed at room temperature for approximately 30 minutes without disturbance. The mononuclear CD34$^+$ HSPCs cells are resuspended in 10 mL (or other appropriate volume) of Iscoves Modified Dulbeccos Medium (IMDM) and counted. The total number of cells is calculated in order to determine the final cell number for each 35 mm culture plate. For example, the approximate cell number needed for each 35 mm culture plate $5.0 \times 10^2$-$2.0 \times 10^3$ for enriched CD34$^+$ cells in approximately 1.1 ml media. After the number of cells per 35 mm plate has been determined, the appropriate volume of cells (plus a slight excess) is then transferred into a new 15 mL centrifuge tube and centrifuged for 10 minutes at 300×G. The supernatant is removed and the pelleted cells are resuspended in cell resuspension solution (or an appropriate media) to the desired stock cell number. The stock cell number ideally is approximately 10× the final number needed for the assay.

Prior to plating, the suspension of cells should be vigorously vortexed to thoroughly mix cells with the media, and the tube is allowed to sit without agitation for approximately 20 minutes to allow air bubbles to escape. An aliquot of 1.1 mL of the final cell mixture is added to a 35 mm culture plate using a 3 mL syringe fitted with a 16 gauge needle. The cell mixture is spread evenly over the surface of the plate by gently rotating the plate.

Two 35 mm sample plates and a 35 mm uncovered plate containing 3-4 mL sterile water are placed in a 100 mm culture plate and the 100 mm plate is covered. The sterile water plate serves to maintain the humidity necessary for colony development. The cells are incubated for 14-16 days at 37° C. and 5% $CO_2$. Care should be exercised to avoid disturbing the plate during the incubation period to prevent shifting of the colonies. After approximately two weeks, the colonies are ready for identification by morphology and counted, otherwise known as "scoring". Identification and counting of the individual colonies can be carried out using an inverted microscope and a scoring grid.

To be counted as a "colony" in this assay, a colony will comprise at least 40 cells are counted (or the minimum cell count set by each laboratory).

The following are the morphologies of the various colony types.

CFU-E (Colony forming unit-erythroid): clonogenic progenitors that produce only one or two clusters with each cluster containing from 8 to approximately 100 hemoglobinized erythroblasts. It represents the more mature erythroid progenitors that have less proliferative capacity.

CFU-G (Colony forming unit-granulocyte): Clonogenic progenitors of granulocytes that give rise to a homogeneous population of eosinophils, basophils or neutrophils.

CFU-GM (Colony forming unit-granulocyte, macrophage): Progenitors that give rise to colonies containing a heterogeneous population of macrophages and granulocytes. The morphology is similar to the CFU-M and CFU-G descriptions.

BFU-E (Burst forming unit-erythroid): The size of the colony can be described as small (3 to 8 clusters), intermediate (9 to 16 clusters), or large (more than 16 clusters) according to the number of clusters present. These are primitive erythroid progenitors that have high proliferative capacity.

CFU-M (Colony forming unit-macrophage): Clonogenic progenitors of macrophages that give rise to a homogenous population of macrophages.

CFU-GEMM (Colony forming unit-granulocyte, erythrocyte, macrophage, megakaryocyte): Multi-lineage progenitors that give rise to erythroid, granulo-cyte, macrophage and megakaryocyte lineages, as the name indicates.

In addition, the progeny cells of the various colony types can be differentiated by the expression or non-expression of surface marker proteins: early progenitor HSPCs (CD34$^+$), mature myeloid (CD14$^+$, CD33$^+$), B lymphoid (CD19$^+$) and megakaryocytic (CD61$^+$).

Long-Term Culture-Initiating Cell Assays (LTC-IC)

In normal adults, the majority of primitive hematopoietic stem progenitor cells are concentrated in the bone marrow, where they are in contact with a variety of molecules that influence their cell-cycle status, viability, motility, and differentiation. These include components of the extracellular matrix, soluble and bound growth-promoting factors and inhibitors, and adhesion molecules that mediate direct interactions between cells. The long-term culture (LTC) system initially developed to support the continued production of myeloid cells, and subsequently for the production of lymphoid cells has provided a unique approach for the investigation of the regulation and maintenance of early HSPCs under conditions that reproduce many aspects of the marrow microenvironment. The LTC system has also provided a basis for the development of powerful assay procedures for quantitating and distinguishing cells at discrete stages of early hematopoietic cell differentiation.

LTC-IC assay quantitates the number of stem progenitor cells that can continue to proliferate for several weeks in culture. The assay can be performed by any methods known in the art, e.g. as disclosed by herein and by C. L. Miller and C, J. Eaves, in "Long-Term Culture-Initiating Cell Assays for Human and Murine Cells" 2001, Methods in Molecular Medicine, 63: 123-141; M. R. Koller, 1998, Blood, 91:4056-4064; Koller M R, et al., Blood 82:378, 1993; Sutherland H J, et al., Proc. Natl. Acad. Sci. USA, 87:3584, 1990; de St Groth S F, J Immunol Methods 49:R11, 1982; and A. Petzer et al., Proc. Natl. Acad. Sci. USA, 1996; 93:1470-1474. These references are incorporated herein by reference in their entirety.

The following is a brief description of an LTC-IC assay by limited dilution assay (LDA). Generally, LTC-IC assay determined by LDA is carried out for cell cultures on irradiated preformed stroma. The stromal cells are grown to confluency in flat-bottom 96-well plates, e.g. 96-well plates at 10$^4$ per well in 100 µL LTC-IC medium, and irradiated at 30 Gy. Test cells are then added to these irradiated stromal layers at four concentrations in 100 µL LTC-IC medium per well (20 replicates each). The plates are then placed at 33° C. in a fully humidified atmosphere of 5% $CO_2$ in air, and cell cultures are fed weekly by replacing 100 µL LTC-IC medium per well. At week 5, adherent and non adherent cells were harvested from each well. Cells from each well are added directly to 0.25 mL of colony assay medium in non-tissue culture-treated 24-well plates (Falcon, Lincoln Park, N.J.). After 14 days, wells were scored for colonies as before. For each sample, the number of LTC-IC was determined through an iterative calculation procedure based on the maximum likelihood solution method.

Formulation and Administration

Depending on the specific embodiment, pharmaceutical compositions described herein can include agents that stimulate or promote HSPC expansion/self renewal/long-term culture initiating colony formation capability, etc, or cells generated from such expansions. Accordingly, formulations for administration of such compositions will depend upon specific embodiments. Agents that promote expansion, etc, can be administered by any suitable route for that agent. Routes of administration include, but are not limited to, intradermal, intramuscular, intraperitoneal, intravenous and subcutaneous routes. The pharmaceutical composition comprising the agent or RNAi agent disclosed herein can be administered by any convenient route, for example by infusion or bolus injection, by absorption through epithelial or mucocutaneous linings (e.g., oral mucosa, rectal and intestinal mucosa, etc.) and can be administered together with other biologically active agents. Administration can be systemic or local.

Compositions comprising cells resulting from HSPC expansion can be administered by any suitable route, but will generally be administered intravenously.

The following describes formulations for compositions as described herein. The applicability of a given formulation in their description to a specific embodiment (e.g to an RNAi agent or to a preparation comprising HSPCs) will be clear to the skilled artisan.

The pharmaceutical compositions disclosed herein should preferably include but are not limited to a composition of the agent, RNAi agent, nucleic acid segments or HSCPs in lactated Ringer's solution and the composition is sterile. Lactated Ringer's solution is a solution that is isotonic with blood and intended for intravenous administration. Include are antioxidants, buffers, antibiotics and solutes that render the compositions substantially isotonic with the blood of an intended recipient. In another embodiment, the composition comprises gene delivery vectors such as shRNA described herein. In another embodiment, the composition also includes water, polyols, glycerine and vegetable oils, and nutrients for cells, for example. Compositions adapted for parenteral administration can be presented in unit-dose or multi-dose containers, in a pharmaceutically acceptable dosage form. Such dosage forms, along with methods for their preparation, are known in the pharmaceutical and cosmetic art. Harry's Cosmeticology (Chemical Publishing, 7th ed. 1982); Remington's Pharmaceutical Sciences (Mack Publishing Co., 18th ed. 1990).

In one embodiment, dosage forms include pharmaceutically acceptable carriers that are inherently nontoxic and nontherapeutic. Examples of such carriers include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, and polyethylene glycol.

In one embodiment, other ingredients can be added, including antioxidants, e.g., ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; and sugar alcohols such as mannitol or sorbitol.

The precise dose to be employed in the formulation of the agent or RNAi agent disclosed herein will also depend on the route of administration and should be decided according to the judgment of the practitioner and each patient's circumstances. Effective doses may be extrapolated from dose-response curves derived from in vitro or animal model test systems.

In one embodiment, effective expansion of HSPCs in a subject produces at least a 10% increase in circulating HSPCs and/or total blood cells within at least about two weeks of administering a pharmaceutical composition as disclosed herein. Sample of peripheral circulating blood can be obtained from the subject after administration with the composition and the CD34+ mononuclear cells isolated and counted. In other embodiments, a complete blood count is performed.

Alternatively, the expansion efficacy can be determined by measuring the population of HSPCs in the subject prior to and after the start of treatment. The population of HSPCs can be determined by FACS analysis using the markers characteristic of HSPCs as disclosed herein or known in the art from a sample of peripheral blood.

The skilled artisan will appreciate that certain factors may influence the dosage and timing required to effectively treat a subject, including but not limited to, the general health and/or age of the subject, and other diseases present. Moreover, treatment of a subject with a therapeutically effective dose can include a single administration or a series of administrations. Estimates of effective dosages and in vivo half-lives for an agent or RNAi agent disclosed herein can be made using conventional methodologies or on the basis of in vivo testing using an appropriate animal model, as known in the art, or as described herein. Preferred dosages for the agent or RNAi agent disclosed herein are readily determinable by those of skill in the art by a variety of means.

The present invention can be defined in any of the following alphabetized paragraphs:

[A] A method for expanding ex vivo a population of hematopoietic stem progenitor cells (HSPCs), the method comprising contacting an isolated cell population comprising an HSPC with an RNAi agent which comprises at least 15 contiguous nucleotides differing by no more than 3 nucleotides from SEQ ID NO: 9.

[B] The method of paragraph 1, wherein the RNAi agent comprises a double-stranded ribonucleic acid (dsRNA) wherein the dsRNA comprises a sense strand and an antisense strand, the antisense strand comprising a region of complementarity to and have at least 15 contiguous nucleotides differing by no more than 3 nucleotides from SEQ ID NO: 9.

[C] The method of paragraph [A] or [B], wherein the RNAi agent comprises SEQ ID NO: 9.

[D] The method of paragraph [A], [B], or [C], wherein the isolated cell population comprising an HSPC exhibits at least a 2 fold increase in colony formation capacity when compared to an isolated HSPC that is not contacted with the RNAi agent.

[E] The method of any of paragraphs [A] to [D], wherein the isolated cell population comprising an HSPC exhibits at least a 5 fold increase in long-term culture colony formation capacity when compared to an isolated HSPC that is not contacted with the RNAi agent.

[F] A method for expanding ex vivo a population of hematopoietic stem progenitor cells (HSPCs), the method comprising contacting an isolated cell population comprising an HSPC with an agent which inhibits serine threonine kinase 38 (STK38).

[G] The method of paragraph [F], wherein the agent is an RNAi agent that inhibits gene expression of STK38.

[H] The method of paragraph [G], wherein the RNAi agent comprises at least 15 contiguous nucleotides differing by no more than 3 nucleotides from SEQ ID NO: 9.

[I] The method of paragraph [G] or [H], the RNAi agent comprises a double-stranded ribonucleic acid (dsRNA) wherein the dsRNA comprises a sense strand and an antisense strand, the antisense strand comprising a region of complementarity to and have at least 15 contiguous nucleotides differing by no more than 3 nucleotides from SEQ ID NO: 9.

[J] The method of paragraph [G], [H], or [I], wherein the RNAi agent comprises SEQ ID NO: 9.

[K] The method of any of paragraphs [F] to [J], wherein the isolated cell population comprising an HSPC exhibits at least a 2 fold increase in colony formation capacity when compared to an isolated HSPC that is not contacted with the agent.

[L] The method of any of paragraphs [F] to [K], wherein the isolated cell population comprising an HSPC exhibits at least a 5 fold increase in long-term culture colony formation capacity when compared to an isolated HSPC that is not contacted with the agent.

[M] A method for promoting hematopoietic stem progenitor cell (HSPC) self renewal ex vivo, the method comprising contacting an isolated cell population comprising an HSPC with an RNAi agent which comprises at least 15 contiguous nucleotides differing by no more than 3 nucleotides from SEQ ID NO: 9.

[N] The method of paragraph [M], wherein the RNAi agent comprises a double-stranded ribonucleic acid (dsRNA) wherein the dsRNA comprises a sense strand and an antisense strand, the antisense strand comprising a region of complementarity to and have at least 15 contiguous nucleotides differing by no more than 3 nucleotides from SEQ ID NO: 9.

[O] The method of paragraph [M] or [N], wherein the RNAi agent comprises SEQ ID NO: 9.

[P] The method of any of paragraphs [M] to [O], wherein the isolated cell population comprising an HSPC exhibits at least a 2 fold increase in colony formation capacity when compared to an isolated HSPC that is not contacted with the RNAi agent.

[Q] The method of any of paragraphs [M] to [P], wherein the isolated cell population comprising an HSPC exhibits at least a 5 fold increase in long-term culture colony formation capacity when compared to an isolated HSPC that is not contacted with the RNAi agent.

[R] A method for promoting hematopoietic stem progenitor cell (HSPC) self renewal ex vivo, the method comprising contacting an isolated cell population comprising an HSPC with an agent which inhibits serine threonine kinase 38 (STK38).

[S] The method of paragraph [R], wherein the agent is an RNAi agent that inhibits gene expression of STK38.

[T] The method of paragraph [S], wherein the RNAi agent comprises at least 15 contiguous nucleotides differing by no more than 3 nucleotides from SEQ ID NO: 9.

[U] The method of paragraph [S] or [T], the RNAi agent comprises a double-stranded ribonucleic acid (dsRNA) wherein the dsRNA comprises a sense strand and an antisense strand, the antisense strand comprising a region of complementarity to and have at least 15 contiguous nucleotides differing by no more than 3 nucleotides from SEQ ID NO: 9.

[V] The method of any of paragraphs [S] to [U], wherein the RNAi agent comprises SEQ ID NO: 9.

[W] The method of any of paragraphs [R] to [V], wherein the isolated cell population comprising an HSPC exhibits at least a 2 fold increase in colony formation capacity when compared to an isolated HSPC that is not contacted with the agent.

[X] The method of any of paragraphs [R] to [W], wherein the isolated cell population comprising an HSPC exhibits at least a 5 fold increase in long-term culture colony formation capacity when compared to an isolated HSPC that is not contacted with the agent.

[Y] A method for promoting hematopoietic stem progenitor cell (HSPC) expansion in a subject, comprising administering a therapeutically effective amount of a pharmaceutical composition comprising at least one RNAi agent and a pharmaceutically acceptable carrier, wherein the RNAi agent comprises at least 15 contiguous nucleotides differing by no more than 3 nucleotides from SEQ ID NO: 9.

[Z] The method of paragraph [Y], wherein the RNAi agent comprises a double-stranded ribonucleic acid (dsRNA) wherein the dsRNA comprises a sense strand and an antisense strand, the antisense strand comprising a region of complementarity to and have at least 15 contiguous nucleotides differing by no more than 3 nucleotides from SEQ ID NO: 9.

[AA] The method of paragraph [Y] or [Z], wherein the RNAi agent comprises SEQ ID NO: 9.

[BB] The method of any of paragraph [Y] to [AA], wherein the RNAi agent when transduced into an isolated cell population comprising an HSPC produces HSPCs that exhibit at least a 2 fold increase in colony formation capacity when compared to a control isolated HSPC that is not contacted with the RNAi agent.

[CC] The method of any of paragraphs [Y] to [BB], wherein the RNAi agent when transduced into an isolated cell population comprising an HSPC produces HSPCs that exhibit at least a 10 fold increase in long term culture colony formation capacity when compared to an isolated HSPC that is not contacted with the RNAi agent.

[DD] A method for promoting hematopoietic stem progenitor cell (HSPC) expansion in a subject, comprising administering a therapeutically effective amount of a pharmaceutical composition comprising an agent that inhibits serine threonine kinase 38 (STK38).

[EE] The method of paragraph [DD], wherein the agent is an RNAi agent that inhibits gene expression of STK38.

[FF] The method of paragraph [EE], wherein the RNAi agent comprises at least 15 contiguous nucleotides differing by no more than 3 nucleotides from SEQ ID NO: 9.

[GG] The method of paragraph [EE] or [FF], the RNAi agent comprises a double-stranded ribonucleic acid (dsRNA) wherein the dsRNA comprises a sense strand and an antisense strand, the antisense strand comprising a region of complementarity to and have at least 15 contiguous nucleotides differing by no more than 3 nucleotides from SEQ ID NO: 9.

[HH] The method of any of paragraphs [EE] to [GG], wherein the RNAi agent comprises SEQ ID NO: 9.

[II] The method of any of paragraphs [DD] to [HH], wherein the RNAi agent when transduced into an isolated cell population comprising an HSPC produces HSPCs that exhibit at least a 2 fold increase in colony formation capacity when compared to an isolated HSPC that is not contacted with the agent.

[JJ] The method of any of paragraphs [DD] to [II], wherein the RNAi agent when transduced into an isolated cell population comprising an HSPC produces HSPCs that exhibit at least a 10 fold increase in long-term culture colony formation capacity when compared to an isolated HSPC that is not contacted with the agent.

[KK] A method for transplanting a population of hematopoietic stem progenitor cells (HSPCs), the method comprising:
(a) contacting an isolated cell population comprising an HSPC with a RNAi agent which comprises at least 15 contiguous nucleotides differing by no more than 3 nucleotides from SEQ ID NO: 9;
(b) culturing ex vivo the HSPC from step (a); and
(c) implanting the cultured HSPC from step (b) into a subject.

[LL] The method of paragraph [KK], wherein the HSPC from step (b) is cultured for at least 20 days.

[MM] The method of paragraph [KK] or [LL], wherein the RNAi agent comprises a double-stranded ribonucleic acid (dsRNA) wherein the dsRNA comprises a sense strand and an antisense strand, the antisense strand comprising a region of complementarity to and have at least 15 contiguous nucleotides differing by no more than 3 nucleotides from SEQ ID NO: 9.

[NN] The method of any of paragraphs [KK] to [MM], wherein the RNAi agent comprise SEQ ID NO: 9.

[OO] The method of any of paragraphs [KK] to [NN], wherein the isolated cell population comprising an HSPC exhibits at least a 2 fold increase in colony formation capacity when compared to an isolated HSPC that is not contacted with the RNAi agent.

[PP] The method of any of paragraphs [KK] to [OO], wherein the isolated cell population comprising an HSPC exhibits at least a 5 fold increase in long-term culture colony formation capacity when compared to an isolated HSPC that is not contacted with the RNAi agent.

[QQ] A method for transplanting a population of hematopoietic stem progenitor cells (HSPCs), the method comprising:
(a) contacting an isolated cell population comprising an HSPC with an agent which inhibits serine threonine kinase 38 (STK38).
(b) culturing ex vivo the HSPC from step (a); and
(c) implanting the cultured HSPC from step (b) into a subject.

[RR] The method of paragraph [QQ], wherein the isolated HSPC from step (b) is cultured for at least 20 days.

[SS] The method of paragraph [QQ] or [RR], wherein the agent is an RNAi agent that inhibits gene expression of STK38.

[TT] The method of paragraph [SS], wherein the RNAi agent comprises at least 15 contiguous nucleotides differing by no more than 3 nucleotides from SEQ ID NO: 9.

[UU] The method of paragraph [SS] or [TT], the RNAi agent comprises a double-stranded ribonucleic acid (dsRNA) wherein the dsRNA comprises a sense strand and an antisense strand, the antisense strand comprising a region of complementarity to and have at least 15 contiguous nucleotides differing by no more than 3 nucleotides from SEQ ID NO:9.

[VV] The method of any of paragraphs [SS] to [UU], wherein the RNAi agent comprises SEQ ID NO: 9.

[WW] The method of any of paragraphs [QQ] to [VV], wherein the isolated cell population comprising an HSPC exhibits at least a 5 fold increase in colony formation capacity when compared to an isolated HSPC that is not contacted with the agent.

[XX] The method of any of paragraphs [QQ] to [WW], wherein the isolated cell population comprising an HSPC exhibits at least a 5 fold increase in long-term culture colony formation capacity when compared to an isolated HSPC that is not contacted with the agent.

[YY] Use of a RNAi agent for transplanting a population of hematopoietic stem progenitor cells (HSPCs), the use comprising:
(a) contacting an isolated cell population comprising an HSPC with a RNAi agent which comprises at least 15 contiguous nucleotides differing by no more than 3 nucleotides from SEQ ID NO: 9;
(b) culturing ex vivo the HSPC from step (a); and
(c) implanting the cultured HSPCs from step (b) into a subject.

[ZZ] The use of paragraph [YY], wherein the isolated cell population comprising an HSPC from step (b) is cultured for at least 20 days.

[AAA] The use of paragraph [YY] or [ZZ], wherein the RNAi agent comprises a double-stranded ribonucleic acid (dsRNA) wherein the dsRNA comprises a sense strand and an antisense strand, the antisense strand comprising a region of complementarity to and have at least 15 contiguous nucleotides differing by no more than 3 nucleotides from SEQ ID NO:9.

[BBB] The use of paragraph [YY], [ZZ], or [AAA], wherein the RNAi agent comprise SEQ ID NO: 9.

[CCC] The use of any of paragraphs [YY] to [BBB], wherein the isolated cell population comprising an HSPC exhibits at least a 2 fold increase in colony formation capacity when compared to an isolated HSPC that is not contacted with the RNAi agent.

[DDD] The use of any of paragraphs [YY] to [CCC], wherein the isolated cell population comprising an HSPC exhibits at least a 5 fold increase in long term culture colony formation capacity when compared to an isolated HSPC that is not contacted with the RNAi agent.

[EEE] Use of an agent which inhibits serine threonine kinase 38 (STK38) for transplanting a population of hematopoietic stem progenitor cells (HSPCs), the use comprising:
(a) contacting an isolated cell population comprising an HSPC with an agent which inhibits serine threonine kinase 38 (STK38).
(b) culturing ex vivo the HSPC from step (a); and
(c) implanting the cultured HSPC from step (b) into a subject.

[FFF] The use of paragraph [EEE], wherein the isolated cell population comprising an HSPC from step (b) is cultured for at least 20 days.

[GGG] The use of paragraph [EEE] or [FFF], wherein the agent is an RNAi agent that inhibits gene expression of STK38.

[HHH] The use of paragraph [GGG], wherein the RNAi agent comprises at least 15 contiguous nucleotides differing by no more than 3 nucleotides from SEQ ID NO: 9.

[III] The use of paragraph [GGG] or [HHH], the RNAi agent comprises a double-stranded ribonucleic acid (dsRNA) wherein the dsRNA comprises a sense strand and an antisense strand, the antisense strand comprising a region of complementarity to and have at least 15 contiguous nucleotides differing by no more than 3 nucleotides from SEQ ID NO: 9.
[JJJ] The use of paragraph [GGG], [HHH] or [III], wherein the RNAi agent comprises SEQ ID NO: 9.
[KKK] The use of any of paragraphs [EEE] to [JJJ], wherein the isolated cell population comprising an HSPC exhibits at least a 2 fold increase in colony formation capacity when compared to an isolated HSPC that is not contacted with the agent.
[LLL] The use of any of paragraphs [EEE] to [KKK], wherein the isolated cell population comprising an HSPC exhibits at least a 5 fold increase in long-term culture colony formation capacity when compared to an isolated HSPC that is not contacted with the agent.

This invention is further illustrated by the following example which should not be construed as limiting. The contents of all references cited throughout this application, as well as the figures and table therein are incorporated herein by reference.

EXAMPLE

Modifying HSPC function to achieve specific differentiation events or to expand the number of engrafting repopulating cells is of considerable importance for the field of hematopoiesis. Unbiased candidate modifiers screened against a functional outcome of interest has been extremely powerful in other systems and here the feasibility of such an approach is tested in primary human stem/progenitor cells.

Materials and Methods

Vector and virus production—The shRNA library used in this study was a pooled version of the Broad Institute RNAi Consortium (TRC) lentiviral library with approximately 7000 shRNA vectors targeting around 1300 human genes. The pLKO self-inactivating lentiviral vector drives shRNA expression from a human U6 promoter and carries the puromycin-resistance gene under control of a PGK promoter[4]. Lentiviruses were produced by transient transfection of the vector plasmids in human 293T cells along with packaging plasmid (pCMVΔ8.9), and envelope plasmid (vsv-g pHCMV-G) provided by The RNAi Consortium. All shRNA sequences that were individually assessed in the study are listed in Table 1.

Isolation, culture and transduction of cells—CD34+ cells were isolated from umbilical cord blood on Ficoll gradient and CD34+ cells were further separated from the mononuclear cells by double MACS columns (Miltenyi Biotec) as previously described[8]. Cells were cultured in STEMSPAN® Serum-Free Expansion Medium (SFEM) (STEMCELL Technologies), with recombinant human thrombopoietin, stem cell factor and Flt-3 ligand (all from R&D SYSTEMS®), at 100 ng/ml each. Cells (200,000 cells per well) were cultured for one day and then transduced overnight in 24-well plates coated with RETRONECTIN® (TAKARA BIO Inc.) at a multiplicity of infection (MOI) of 2, rendering 20-30% tranduction efficiency of the CD34+ cells[7]. Following transduction, cells were re-plated in fresh STEMSPAN® medium and maintained with bi-weekly half-media changes and wells were split as needed.

CFC and LTC-IC assays—Colony forming cell (CFC) assays were established by plating cells in methylcellulose medium H4445 (STEMCELL Technologies) with or without 2.5 ug/ml puromycin. Cells were plated according to Day 0 cell counts. Two weeks after plating, cultures were evaluated for the presence of the following colony-forming units: CFU-granulocyte-macrophage (CFU-GM), CFU-erythroid (CFU-E) and burst-forming units erythroid (BFU-E). For Long-term culture initiating cell (LTC-IC) assays AFT024 stromal cells (Dr. K. Moore) were grown to confluence in 96-well plates, and irradiated at 1500 rads 24 hours prior to establishing LTC-IC cultures at limit dilution as previously described[8]. LTC-IC cultures were maintained for 5 weeks and medium was then replaced with clonogenic methylcellulose medium. After two weeks, wells were evaluated for the presence of hematopoietic colonies.

Transplantation assays—Cells were intravenously injected into 8-12 weeks old sublethally irradiated (350 rad) NOD/SCID mice. Contribution of human cells in bone marrow (BM) was measured by FACS after 7 weeks using human specific CD45 antibodies. For secondary transplantations a half femur equivalent of BM cells from primary transplanted mice was injected into new mice.

FACS analysis—Cells were stained with anti-human CD34, CD38, CD33, CD45, CD19, and CD15, all APC, PE, or FITC (Becton Dickinson) and analyzed using a FACS-CALIBUR™ (Becton Dickinson).

PCR, cloning and sequencing—To sequence proviral shRNA inserts, methylcellulose colonies from each screening pool were harvested for DNA extraction. PCR amplification of proviral shRNAs was performed using the primers pair 5'-GGATGAATACTGCCATTTGTCTCG-3' (SEQ. ID. NO. 19) and 5'-AGGCCGAAGGAATAGAAGA-3' (SEQ. ID. NO. 20). PCR products were cloned using TOPO TA kit (Invitrogen) and sequenced (10-12 clones per pool). Quantitative RT-PCR was performed using Applied Biosystems Taqman kits.

Results

RNAi screen in human CB CD34+ cells—Based on the limited ability of hematopoietic stem/progenitor cells (HSPCs) to sustain primitive potential under ex vivo culture conditions, a strategy was designed for pooled screens where perturbations conferring enhanced self-renewal/proliferation potential of HSPCs could be detected by positive selection (FIG. 1A). A pooled version of a lentiviral shRNA library from the Broad RNAi Consortium (TRC) targeting 1300 human genes (mainly kinases, phosphatases, and proteases), with on average 5 shRNA vectors per gene, was used in this study[4]. The library vector confers puromycin resistance. Twelve pools of umbilical cord blood derived CD34+ cells (200 000 cells per pool) were each transduced with an aliquot of the complete pooled shRNA library and subsequently passaged in long-term liquid cultures (10 weeks) followed by colony forming cell (CFC) assays to positively select for clones that had acquired enhanced proliferation ability combined with a sustained primitive potential. It should be noted that under the conditions used persistence of cells with this phenotype of enhanced proliferation ability combined with a sustained primitive potential is extremely rare. This rarity provides an attractive baseline for the screening method used. The transduction efficiency was kept relatively low (20-30%) to avoid doubly transduced cells. After 10 weeks in culture, seven of the 12 library-transduced pools exhibited a two- to five-fold increase in the number of CFCs compared to control-transduced pools (FIG. 1B). All of these seven pools now contained close to 100% puromycin resistant cells showing that the long-term culture had mediated a selection for library-transduced cells (FIG. 1B). Of note, one pool (#7) exhibited high levels of burst-forming-unit/colony-forming unit erythroid (BFU/CFU-E) colonies in contrast to the predominantly myeloid-type colonies seen in the other pools. The colonies from each screening pool were harvested in bulk for DNA extraction and subsequent PCR amplification of the proviral inserts. The PCR products were cloned in bacteria and 10-12 clones per pool were sequenced to determine the distribution of shRNAs. FIG. 1C shows the distribution of shRNAs between the different pools. The most prominent hits were shEXT1 (Exostoses 1) which dominated pool 7, shPLCZ1 (Phospholipase C zeta 1) which dominated pools 9 and 12 and was present in pools 8 and 11, and shSTK38 (Serine threonine kinase 38) which dominated pool 4. For functional validation experiments with individual shRNAs, these three hits were selected along with four additional shRNAs which either showed a frequency of more than 30% in a given pool or could be detected in more than one screening pool. The additional shRNA are shPTPN9, shEGLN3, shMLH1 and shABCC12. The shPTPN9 vector did not however produce sufficient virus titers for the validation assays.

Figure 2:
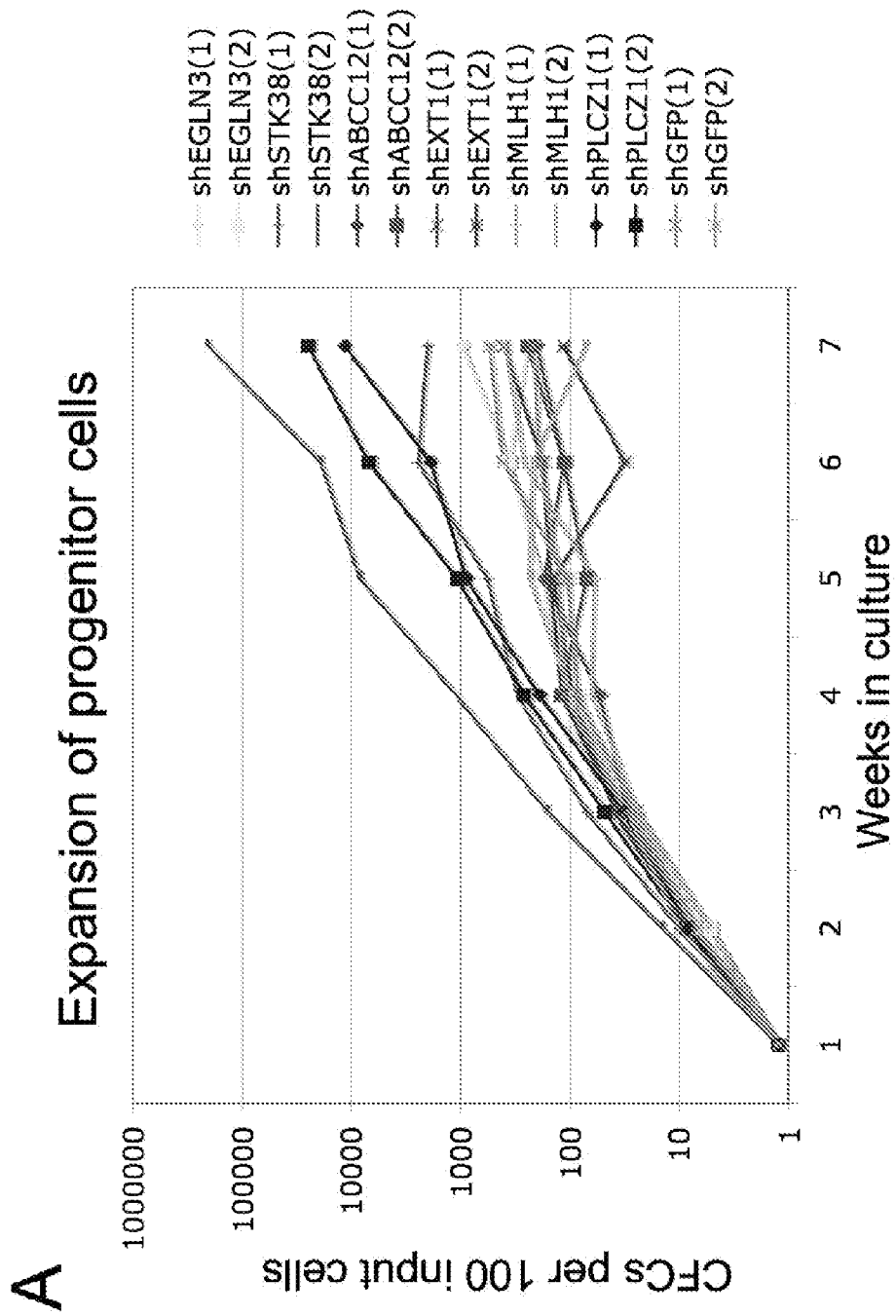
FIG. 2A shows the total CFC numbers of cells transduced with individual shRNA vectors and cultured for several weeks. Results from two experiments are shown.
FIG. 2B shows the frequency of CFU-erythroid/burst-forming unit erythroid (CFU-E/BFU-E) colonies formation in cells transduced with individual shRNA vectors and cultured for several weeks. Results from two experiments are shown.
Figure 2:
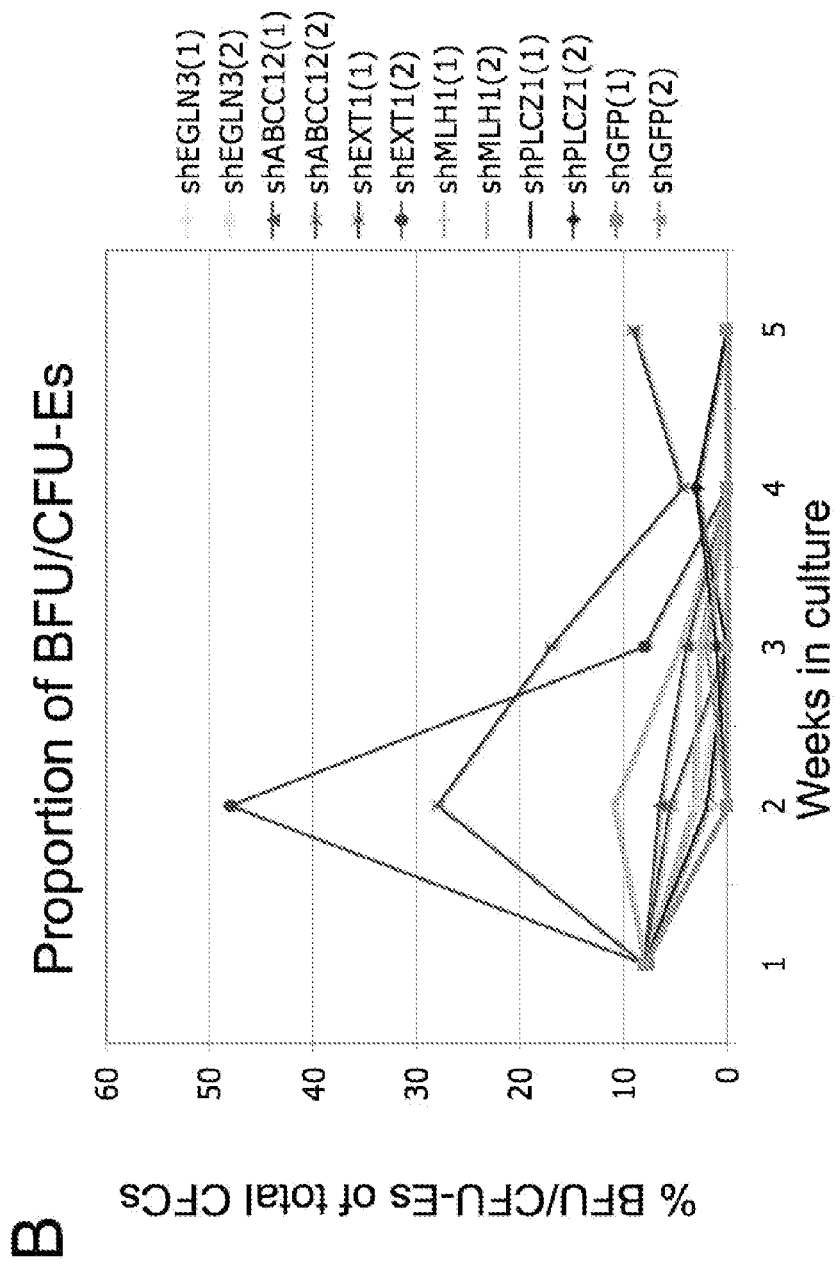

Validation of candidate shRNAs—FIG. 2 summarizes the outcome of the validation assays. Cells transduced with either shPLCZ1 (Phospholipase C zeta 1) or shSTK38 (Serine threonine kinase 38) exhibited a more than a 1000-fold increased expansion of progenitors during culture (FIG. 2A). Despite an exponential growth rate for several weeks, these progenitor cells had not become immortalized and the cells subsequently stopped growing after 12-15 weeks. Cells transduced with shEXT1 (Exostoses 1) did not show the same overall expansion but produced dramatically higher frequencies of BFU/CFU-Es (FIG. 2B), similar to the observation in the primary screen. Interestingly, the marked effect of shEXT1 on BFU/CFU-E formation was only seen after 1-2 weeks, whereas in the initial screen this was observed after 10 weeks of culture. Although it was occasionally noted that there is an increased BFU/CFU-E frequency at later time points, the only consistent effect was at 1-2 weeks. It is possible that the effect at later time points required an optimal integration site of the vector or an initial target cell with certain rare qualities. Nevertheless, the three most prominent hits from the screen, shSTK38, shPLCZ1 and shEXT1 represented strong and reproducible perturbations specifically mediated by shRNAs.

Knockdown of EXT1 leads to increased BFU/CFU-E production—The investigators next asked whether the higher levels of BFU/CFU-E colonies triggered by shEXT1 could be reproduced with additional non-overlapping shRNAs targeting EXT1. The library contained five additional shRNAs against EXT1 that were tested functionally in the BFU/CFU-E assays as well as for knockdown of the EXT1 transcript. It should be noted that the aim when assessing knockdown is to test relative efficiency of the different shRNAs, and that the level of transcript suppression must be interpreted with caution when testing heterogenous populations of primary cells. The level of knockdown in each cell will vary depending on differentiation stage, vector copy number and integration site. The knockdown values from the transduced populations can mainly be used as a guide for relative potency of shRNAs rather than as an indicator of absolute levels.

Figure 3:
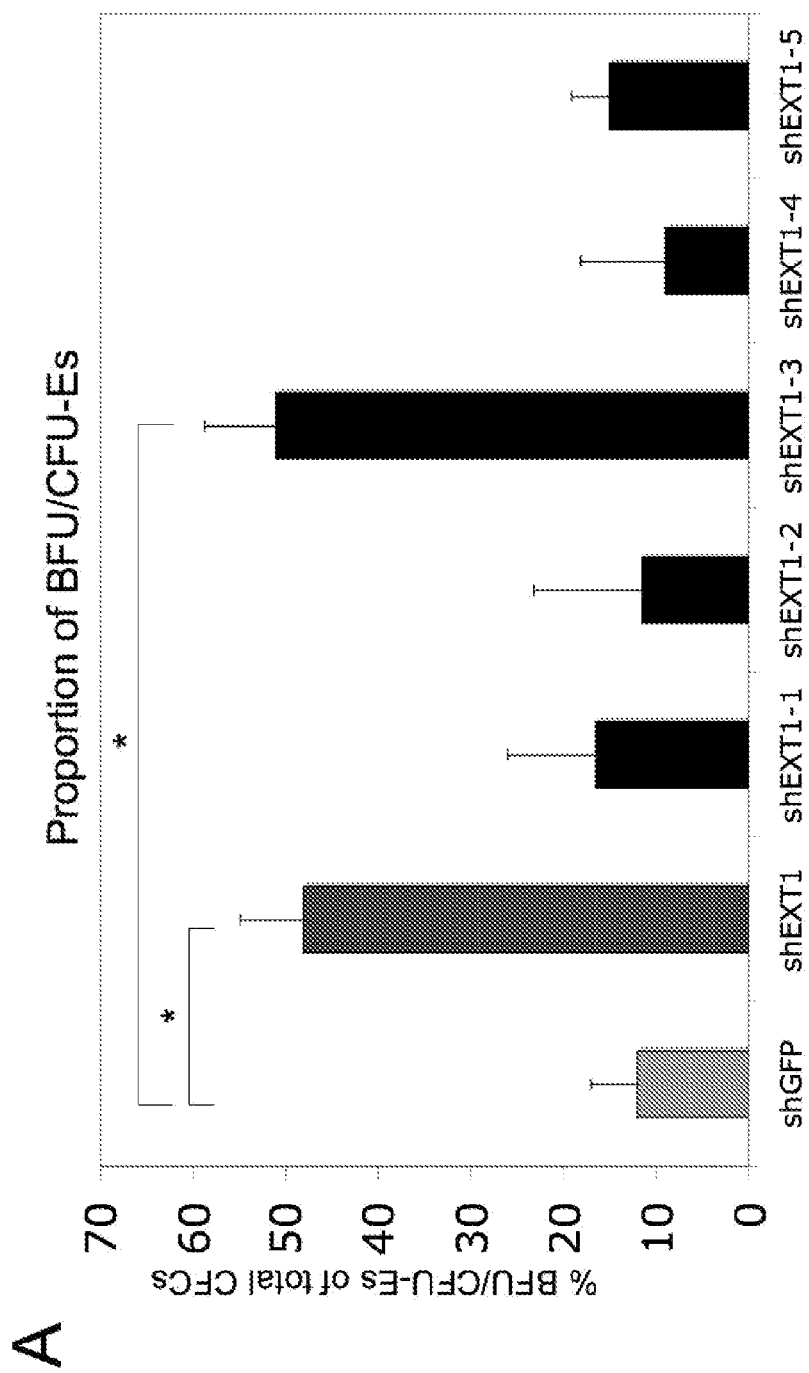
FIG. 3A shows the effects of various shRNA vectors that target different regions of the Exostoses 1 (EXT1) transcript on the erythroid progenitor activity of respectively transduced cells as measured by frequency of erythroid progenitors one week after transduction. Results are given as mean values±SEM; *$p<0.05$ (Student t-test).
FIG. 3B shows the effects of the shRNA constructs of FIG. 3A on the expression of the EXT1 transcript as measured by qPCR. Results from three independent experiments are shown.
Figure 3:
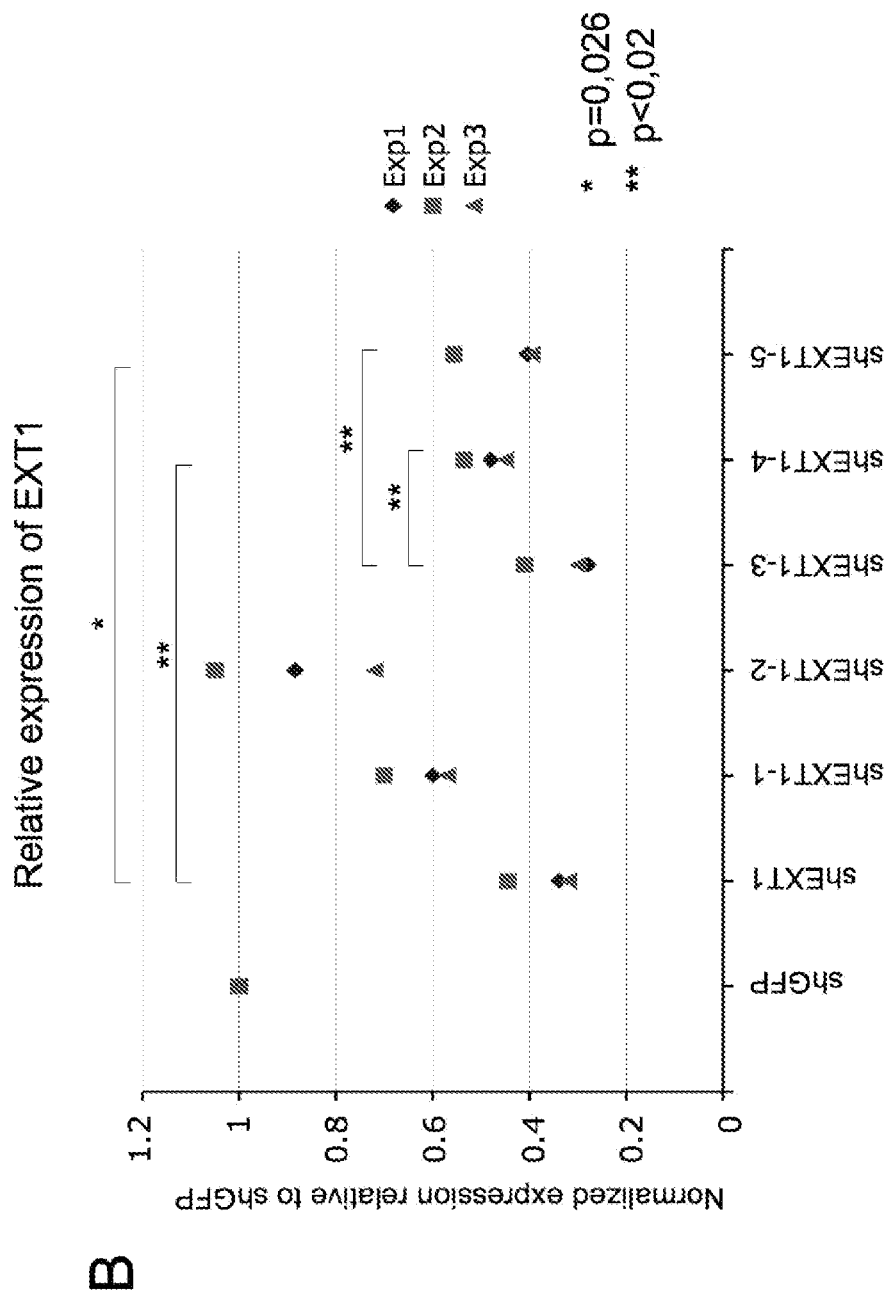

One additional shRNA that conferred the erythroid phenotype and also knocked down the EXT1 transcript with similar efficiency as the original construct was found (FIGS. 3 A and B). The other four constructs did not render a phenotype and showed significantly less efficient knockdown (FIG. 3B). To assess differences in relative knockdown efficiency a paired t-test was used to test significance when comparing shEXT1 and shEXT1-3 with any of the other shRNAs. P-values are indicated for the comparisons with shEXT1-4 and shEXT1-5. For comparisons with the other shRNAs, the p-values were below 0.02.

Figure 4:
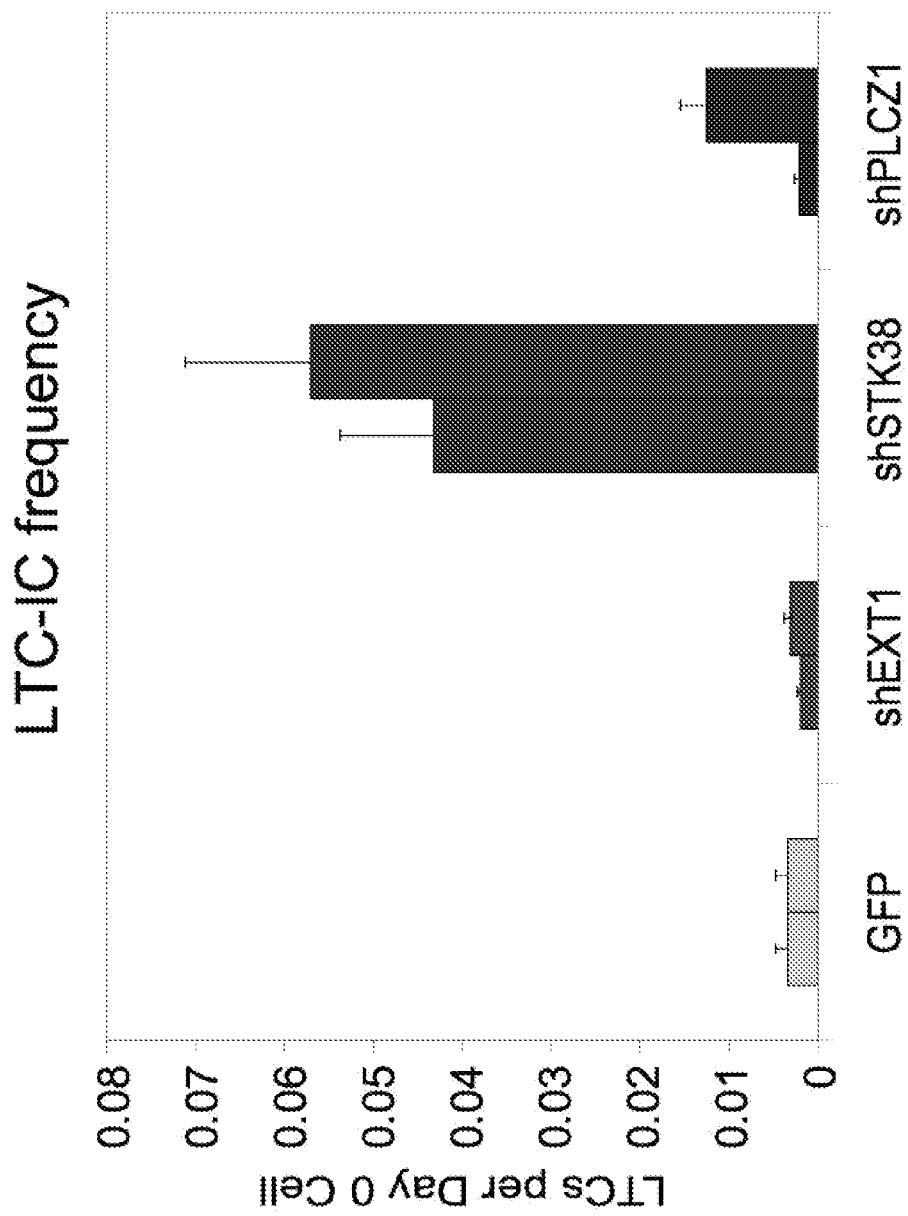
FIG. 4 shows the markedly increased numbers of long term culture initiating cells (LTC-ICs) induced by shSTK38. The frequency of LTC-ICs one week after transduction is shown for two independent experiments. The error bars give the 95% confidence interval from the limiting-dilution LTC-IC calculations.
Figure 5:
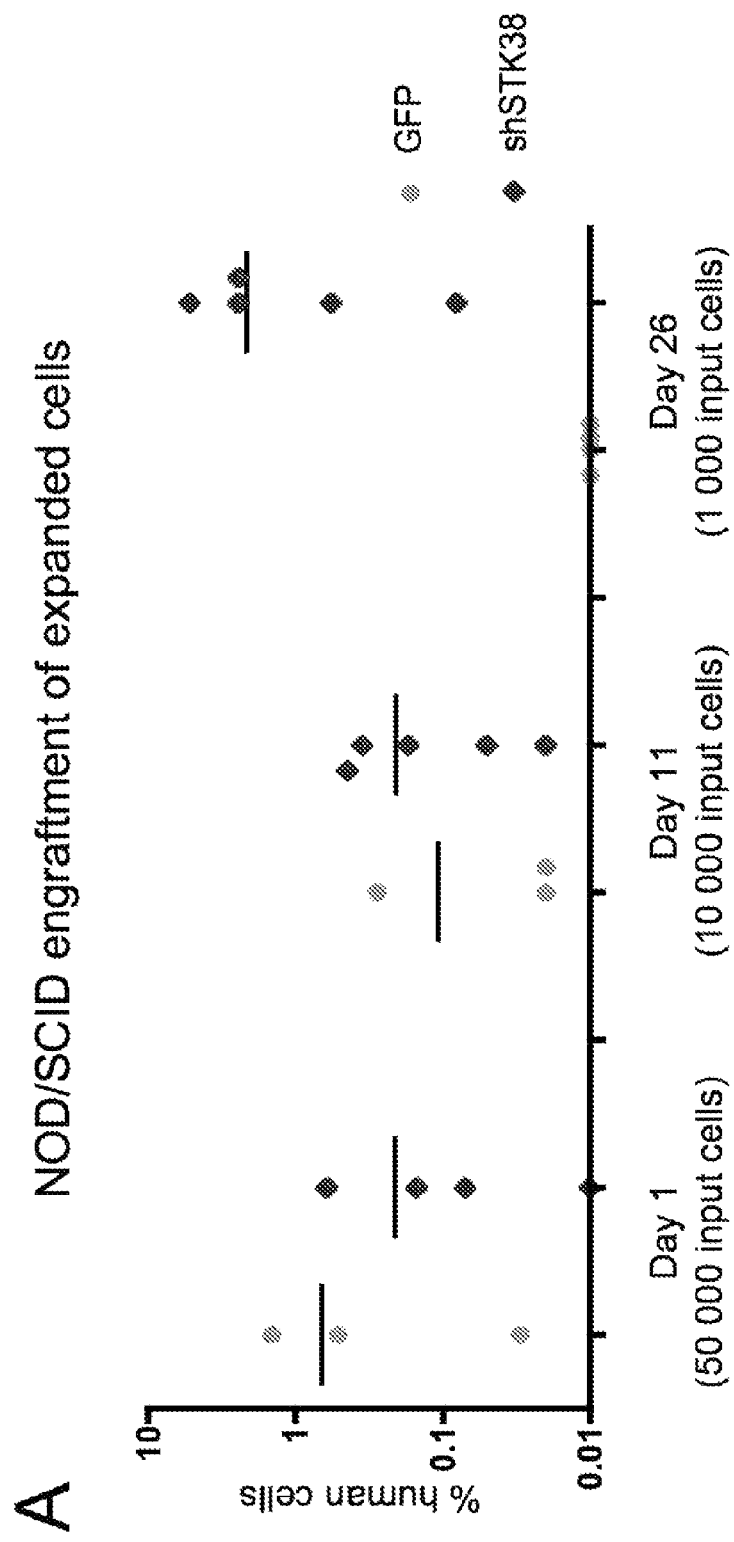
FIG. 5A shows the increased ability/success of engraftment of expanded cells transduced by shSTK38N.
FIG. 5B shows the FACS plots from a representative mouse with which Day 26 shSTK38 expanded cells were transplanted and these cells demonstrate lymphoid and myeloid engraftment in the NOD/SCID mouse.
FIG. 5C are the FACS plots showing engrafted human cells in one of two secondary recipients NOD/SCID mice wherein the human CD45$^+$ cells were the Day 26 shSTK38 expanded cells prior to transplant into the primary recipient mouse.
Figure 5:
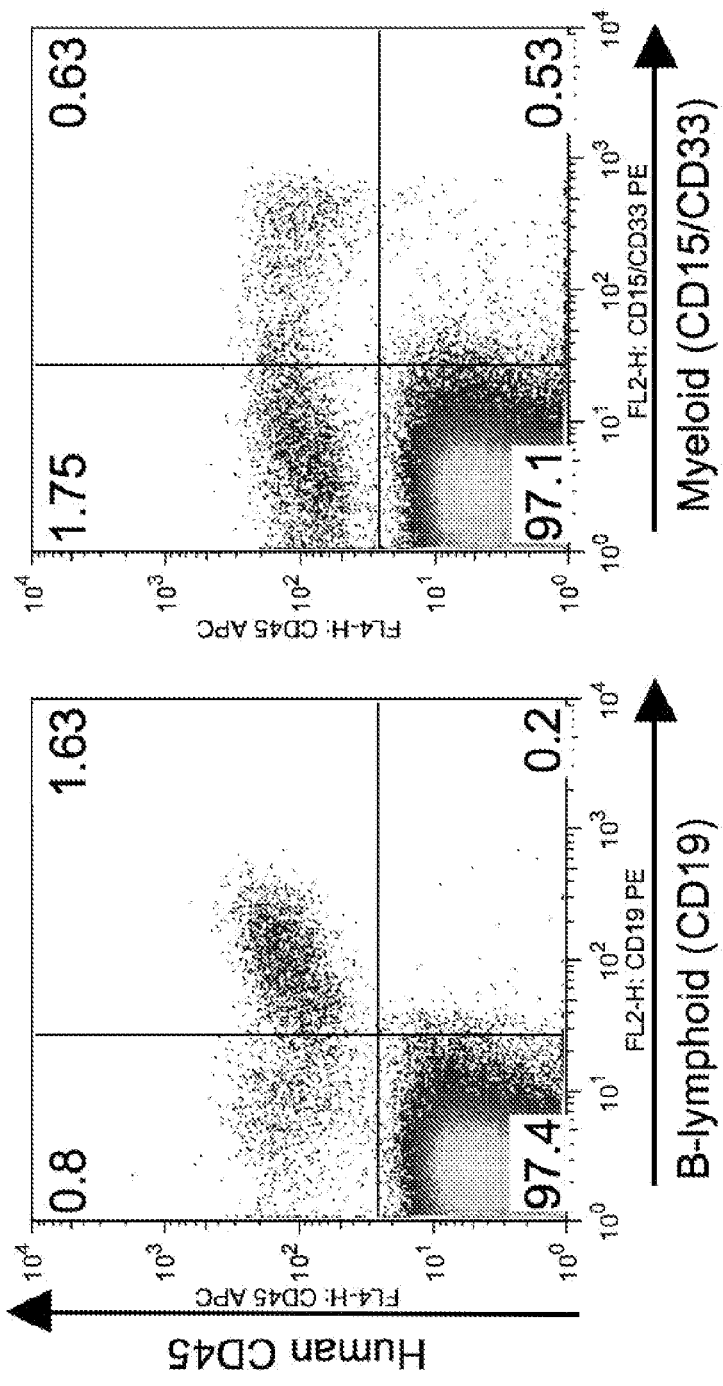
Figure 5:
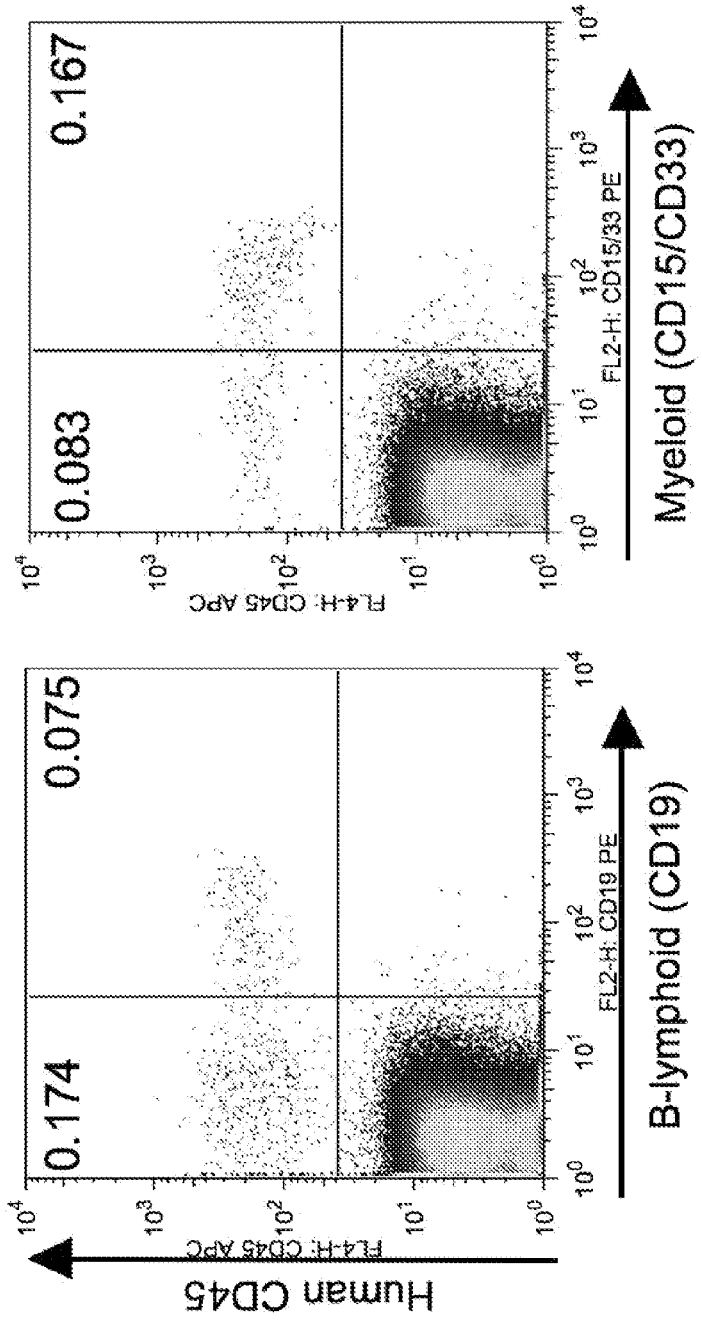
Figure 6:
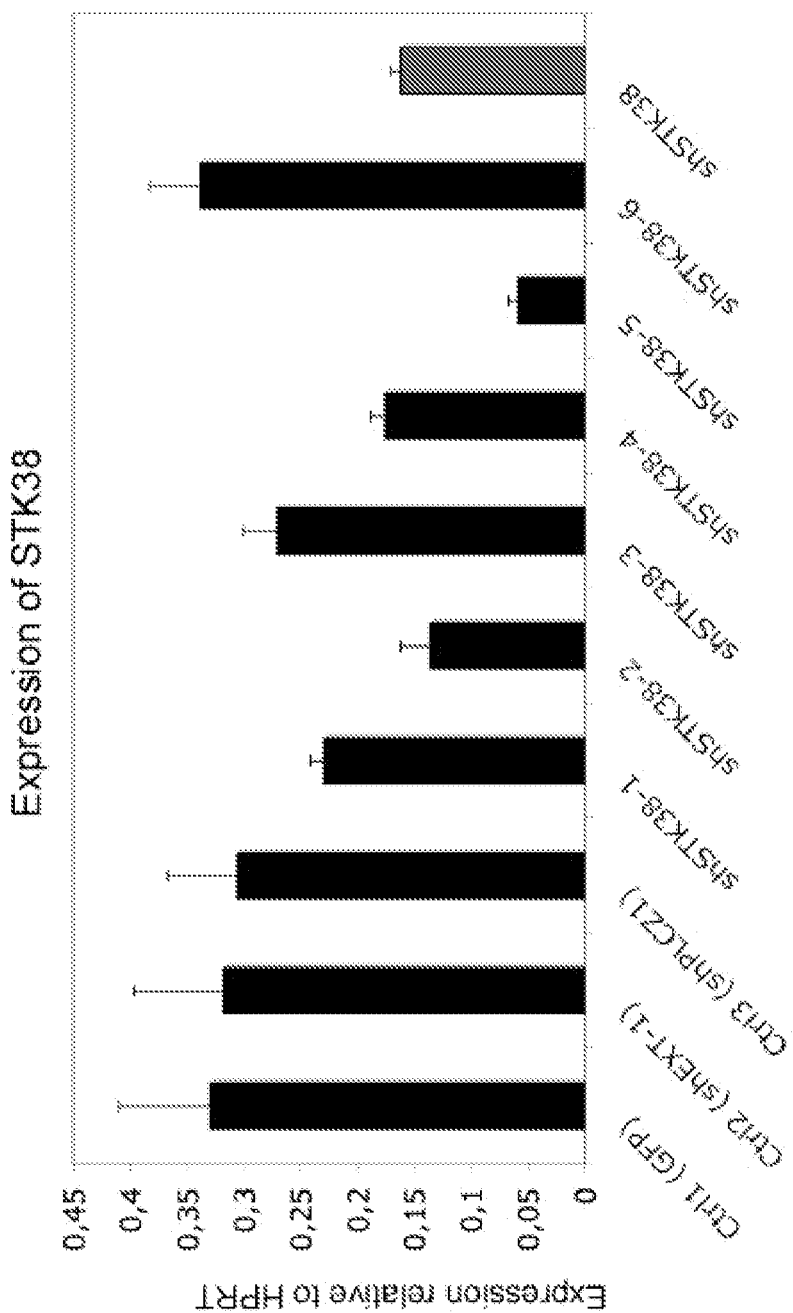
FIG. 6 shows the effects of six additional shRNA vectors that target different regions of the STK38 transcript on the level of knockdown expression of STK38 in CB CD34+ cells as determined by qPCR.

This strongly suggests that the effect on BFU/CFU-E production is specifically mediated by the loss of EXT1. EXT proteins are required for the biosynthesis of heparan sulfate proteoglycans and studies in *Drosophila* have shown that they thereby regulate the presentation of certain secreted growth factors such as Wnt and TGF-beta at the cell surface[9,10].

shSTK38 expands candidate human hematopoietic stem cells—To further characterize the dramatic expansion effects from shPLCZ1 and shSTK38 and assess whether self-renewal of stem cells was affected, the long-term culture initiating cell (LTC-IC) assays were performed. This assay can detect cells in a quantitative manner, detect cells that are primitive and thus reflect repopulating HSPCs[11]. Cells transduced with shSTK38, but not shPLCZ1 or shEXT1, displayed significantly higher numbers of LTC-ICs, as measured by limiting dilution assays (LDAs), after one week in culture, indicative of an immediate effect on HSPC self-renewal (FIG. 4). The investigators focused on shSTK38 and first attempted to validate the target identity using six additional shRNA vectors against STK38. While several constructs knocked down the STK38 transcript to similar levels or even better than the original vector (FIG. 6), they did not trigger a similar expansion effect indicating that the phenotype is mediated, at least partly, through an "off target effect" on another gene. The investigators proceeded to study the effect from shSTK38 on modifying HSPC self-renewal. To more stringently assess the potential for stem cell expansion, shSTK38 transduced CD34$^+$ cells were transplanted into NOD/SCID mice either immediately after transduction or following 11 and 26 days of ex vivo culture. The transplanted cell doses were expansion equivalents of the indicated numbers of input Day 0 CD34$^+$ cells prior to transduction. The level of human engraftment in bone marrow seven weeks post transplantation is shown in FIG. 5A. The level of human engraftment seven weeks post transplantation for 50,000 input cells transplanted one day after transduction did not differ between control and test cells (FIG. 5A). However, when transplanting the progeny of only 1000 input cells after 26 days of culture, higher engraftment of shSTK38 transduced cells as compared to the 50-fold higher input dose transplanted at day 1 was observed (FIG. 5A). These data indicate a dramatic (>50-fold) expansion of NOD/SCID repopulating activity over 26 days of culture. The cells expanded by shSTK38 were fully functional NOD/SCID repopulating cells as defined by both B-lymphoid (CD19$^+$) and myeloid engraftment (CD33$^+$ and CD15$^+$) (FIG. 5B) and also showed low but clearly detectable engraftment in secondary recipients (FIG. 5C). In FIG. 5C, half a femur equivalent of bone marrow from primary recipient mice was transplanted to a total of ten secondary recipients. Engraftment levels were analyzed in bone marrow after seven weeks. consistent with stem cell self-renewal. Thus, these data show by assays stringently assessing for stem cell rather than progenitor cell function that shSTK38 induces substantial ex vivo expansion of human hematopoietic stem cells.

Here the investigators have identified three types of outcomes associated with three specific shRNAs that are informative about such screens. First, shRNAs targeting EXT1 induce an EXT1 specific effect and is an example of an unpredicted candidate gene target that alters at least ex vivo hematopoietic activity. Second, shPLCZ1 modified a population of progenitor cells in vitro that did not score in subsequent more stem cell specific assays. Third, shSTK38 revealed a consistent and potent effector of human hematopoietic stem cells resulting in dramatic expansion of the cells. Yet, its specific molecular targets remain ill-defined and do not appear to be the sequence against which the shRNA was engineered. This outcome is of greatest interest by virtue of its functional effect, despite leaving the question of the actual gene target open.

Two general aspects about the screening strategy are important to consider. First, while this first screen most likely had coverage of the entire library (7000 shRNAs) in progenitor cells (CFCs), it did not saturate the library with respect to the targeting of the most primitive populations such as LTC-ICs and SCID repopulating cells (SRCs). Based on the current experience from assaying these populations from fresh CB CD34+ cells and given a 30% transduction efficiency of the shRNA library, it is estimated that this screen had a 5-fold coverage of the library in CFCs, 50% coverage in LTC-ICs and 10% coverage in SRCs. Thus, additional screens with higher cell numbers will be necessary for a deep assessment of the library in the most primitive populations. Second, considering the use of integrating viral vectors and the selective pressure in the screening assays, functional outcomes could be associated with insertional mutagenesis events, for example from activation of proto-onocogenes[14]. The cells were therefore transduced at a relatively low multiplicity of infection (MOI) to avoid multiple integrations of the library vectors. It is still a possibility that the candidate shRNAs not showing a clear phenotype in the validation experiments initially scored due to insertional mutagenesis. However, the most prominent outcomes from the primary screen were not associated with such mechanisms but specifically mediated by shRNA. It should also be noted that all phenotypes reported here for individual shRNAs were consistently reproduced in multiple experiments arguing against any involvement of lentiviral integration effects at that level.

The references cited herein and throughout the specification are incorporated herein by reference.

References

1. Sorrentino B P. Clinical strategies for expansion of haematopoietic stem cells. Nat. Rev. Immunol. 2004, 4:878-888.
2. Berns K, et al. A large-scale RNAi screen in human cells identifies new components of the p53 pathway. Nature, 2004, 428:431-437.
3. Kolfschoten I G, et al. A genetic screen identifies PITX1 as a suppressor of RAS activity and tumorigenicity. Cel 2005, 121:849-858.
4. Moffat J, et al. A lentiviral RNAi library for human and mouse genes applied to an arrayed viral high-content screen. Cell 2006, 124:1283-1298.
5. Paddison P J, et al. A resource for large-scale RNA-interference-based screens in mammals. Nature 2004, 428:427-431.
6. Westbrook T F, et al. A genetic screen for candidate tumor suppressors identifies REST. Cell 2005, 121:837-848.
7. Woods N B, et al. Lentiviral gene transfer into primary and secondary NOD/SCID repopulating cells. Blood 2000, 96:3725-3733.
8. Lewis I D, et al. Umbilical cord blood cells capable of engrafting in primary, secondary, and tertiary xenogeneic hosts are preserved after ex vivo culture in a noncontact system. Blood 2001, 97:3441-3449.
9. Lind T, et al. The putative tumor suppressors EXT1 and EXT2 are glycosyltransferases required for the biosynthesis of heparan sulfate. J Biol. Chem. 1998, 273:26265-26268.
10. Han C, et al. Distinct and collaborative roles of *Drosophila* EXT family proteins in morphogen signalling and gradient formation. Development 2004, 131:1563-1575.
11. Cho R H, Muller-Sieburg C E. High frequency of long-term culture-initiating cells retain in vivo repopulation and self-renewal capacity. Exp Hematol. 2000, 28:1080-1086.
12. Fan X, et al. Efficient adenoviral vector transduction of human hematopoietic SCID-repopulating and long-term culture-initiating cells. Hum Gene Ther. 2000, 11:1313-1327.
13. Zhang J, et al. Silencing p21 (Waf1/Cip1/Sdi1) expression increases gene transduction efficiency in primitive human hematopoietic cells. Gene Ther. 2005, 12:1444-1452.
14. Woods N B, et al. Lentiviral vector transduction of NOD/SCID repopulating cells results in multiple vector integrations per transduced cell: risk of insertional mutagenesis. Blood 2003, 101:1284-1289.

TABLE 1

List of all shRNAs used in this study.

| Name | Target sequence (sense strand) |
|---|---|
| shGFP | GGTGCGCTCCTGGACGTAGCC (SEQ ID NO. 1) |
| shEXT1 | GAAGAACACAGCGGTAGGAAT (SEQ ID NO. 2) |
| shEXT1-1 | AGAGCCAGATTGTGCCAACTA (SEQ ID NO. 3) |
| shEXT1-2 | CCTGCTTCGATTTCACCCTTT (SEQ ID NO. 4) |
| shEXT1-3 | CCCAACTTTGATGTTTCTATT (SEQ ID NO. 5) |
| shEXT1-4 | GCACTTAGACAGCAGACACAA (SEQ ID NO. 6) |
| shEXT1-5 | CCTTCGTTCCTTGGGATCAAT (SEQ ID NO. 7) |
| shPLCZ1 | CGTGAATGTCTACTGTTTAAA (SEQ ID NO. 8) |
| shSTK38 | CAGCAAGGGCCATGTGAAACT (SEQ ID NO. 9) |
| shSTK38-1 | GCTCGGAAGGAAACAGAGTTT (SEQ ID NO. 10) |
| shSTK38-2 | GCAGAAACAGTATTAGCCATA (SEQ ID NO. 11) |
| shSTK38-3 | CCCACCAATATGTCATAGTAA (SEQ ID NO. 12) |
| shSTK38-4 | CCCACCAAGTATTTCCTTTAT (SEQ ID NO. 13) |
| shSTK38-5 | CAGAGACATCAAACCAGACAA (SEQ ID NO. 14) |
| shSTK38-6 | CATGTGAAACTTTCTGACTTT (SEQ ID NO. 15) |
| shEGLN3 | CTACGTCAAGGAGAGGTCTAA (SEQ ID NO. 16) |
| shMLH1 | TATTCCATCCGGAAGCAGTAC (SEQ ID NO. 17) |
| shABCC12 | GCGATGTTACTAGCAGCAGAA (SEQ ID NO. 18) |

What is claimed:

1. A method for expanding ex vivo a population of hematopoietic stem progenitor cells (HSPCs), the method comprising contacting an isolated cell population comprising an HSPC with an RNAi agent which comprises at least 15 contiguous nucleotides differing by no more than 3 nucleotides from SEQ ID NO: 9.

2. The method of claim 1, wherein the RNAi agent comprises a double-stranded ribonucleic acid (dsRNA) wherein the dsRNA comprises a sense strand and an antisense strand, the antisense strand comprising a region of complementarity to and having at least 15 contiguous nucleotides differing by no more than 3 nucleotides from SEQ ID NO: 9.

3. The method of claim 1, wherein the RNAi agent comprises the nucleotide sequence of SEQ ID NO: 9.

4. A method for expanding ex vivo a population of hematopoietic stem progenitor cells (HSPCs), the method comprising contacting an isolated HSPC with an agent which inhibits serine threonine kinase 38 (STK38), wherein the agent is an RNAi agent that inhibits gene expression of STK38.

5. A method for promoting hematopoietic stem progenitor cell (HSPC) expansion in a subject, comprising administering a therapeutically effective amount of a pharmaceutical composition comprising at least one RNAi agent and a pharmaceutically acceptable carrier, wherein the RNAi agent comprises at least 15 contiguous nucleotides differing by no more than 3 nucleotides from SEQ ID NO: 9.

6. A method for promoting hematopoietic stem progenitor cell (HSPC) expansion in a subject, comprising administering a therapeutically effective amount of a pharmaceutical composition comprising an agent that inhibits serine threonine kinase 38 (STK38), wherein the agent is an RNAi agent that inhibits gene expression of STK38.

7. The method of claim 6, wherein the RNAi agent comprises the nucleotide sequence of SEQ ID NO: 9.

8. A method for transplanting a population of hematopoietic stem progenitor cells (HSPCs), the method comprising:
   a. contacting an isolated cell population comprising an HSPC with a RNAi agent which comprises at least 15 contiguous nucleotides differing by no more than 3 nucleotides from SEQ ID NO: 9;
   b. culturing ex vivo the HSPC from step (a); and
   c. implanting the cultured HSPC from step (b) into a subject.

9. The method of claim 8, wherein the isolated cell population comprising an HSPC from step (b) is cultured for at least 20 days.

10. A method for transplanting a population of hematopoietic stem progenitor cells (HSPCs), the method comprising:
    a. contacting an isolated cell population comprising an HSPC with an agent which inhibits serine threonine kinase 38 (STK38).
    b. cultuling ex vivo the HSPC from step (a); and
    c. implanting the cultured HSPC from step (b) into a subject, wherein the agent is an RNAi agent that inhibits gene expression of STK38.

11. The method of claim 10, wherein the isolated cell population comprising an HSPC from step (b) is cultured for at least 20 days.

12. The method of claim 10, wherein the RNAi agent comprises a double-stranded ribonucleic acid (dsRNA) wherein the dsRNA comprises a sense strand and an antisense strand, the antisense strand comprising a region of complementarity to and having at least 15 contiguous nucleotides differing by no more than 3 nucleotides from SEQ ID NO:9.

* * * * *

UNITED STATES PATENT AND TRADEMARK OFFICE
CERTIFICATE OF CORRECTION

PATENT NO. : 8,642,569 B2  
APPLICATION NO. : 13/145706  
DATED : February 4, 2014  
INVENTOR(S) : Scadden et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 86 days.

Signed and Sealed this

Twenty-ninth Day of September, 2015

Michelle K. Lee
*Director of the United States Patent and Trademark Office*